(12) United States Patent
Boitano et al.

(10) Patent No.: US 12,006,370 B2
(45) Date of Patent: Jun. 11, 2024

(54) USE OF ANTI-CD5 ANTIBODY DRUG CONJUGATE (ADC) IN ALLOGENEIC CELL THERAPY

(71) Applicant: Heidelberg Pharma Research GmbH, Ladenburg (DE)

(72) Inventors: Anthony Boitano, Newton, MA (US); Michael Cooke, Boston, MA (US)

(73) Assignee: Heidelberg Pharma Research GmbH, Ladenburg (DE)

( * ) Notice: Subject to any disclaimer, the term of this patent is extended or adjusted under 35 U.S.C. 154(b) by 426 days.

(21) Appl. No.: 17/155,832

(22) Filed: Jan. 22, 2021

(65) Prior Publication Data

US 2021/0355230 A1 Nov. 18, 2021

Related U.S. Application Data

(63) Continuation of application No. PCT/US2019/043125, filed on Jul. 23, 2019.

(60) Provisional application No. 62/773,047, filed on Nov. 29, 2018, provisional application No. 62/702,296, filed on Jul. 23, 2018.

(51) Int. Cl.
| | |
|---|---|
| *C07K 16/28* | (2006.01) |
| *A61K 31/40* | (2006.01) |
| *A61K 31/535* | (2006.01) |
| *A61K 31/5517* | (2006.01) |
| *A61K 31/704* | (2006.01) |
| *A61K 35/17* | (2015.01) |
| *A61K 47/68* | (2017.01) |
| *C07K 14/705* | (2006.01) |
| *C07K 14/725* | (2006.01) |

(52) U.S. Cl.
CPC .......... *C07K 16/2896* (2013.01); *A61K 31/40* (2013.01); *A61K 31/535* (2013.01); *A61K 31/5517* (2013.01); *A61K 31/704* (2013.01); *A61K 35/17* (2013.01); *A61K 47/6809* (2017.08); *A61K 47/6831* (2017.08); *A61K 47/6849* (2017.08); *C07K 14/7051* (2013.01); *C07K 14/70521* (2013.01); *C07K 14/70578* (2013.01); *C07K 16/2806* (2013.01); *C07K 2317/622* (2013.01); *C07K 2319/02* (2013.01)

(58) Field of Classification Search
CPC .................................. C07K 16/2896
See application file for complete search history.

(56) References Cited

U.S. PATENT DOCUMENTS

| | | | |
|---|---|---|---|
| 3,896,111 A | 7/1975 | Kupchan et al. | |
| 4,137,230 A | 1/1979 | Hashimoto et al. | |
| 4,151,042 A | 4/1979 | Higashide et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,424,219 A | 1/1984 | Hashimoto et al. | |
| 4,450,254 A | 5/1984 | Isley et al. | |
| 4,671,958 A | 6/1987 | Rodwell et al. | |
| 4,816,397 A | 3/1989 | Boss et al. | |
| 4,816,567 A | 3/1989 | Cabilly et al. | |
| 4,880,935 A | 11/1989 | Thorpe | |
| 4,970,198 A | 11/1990 | Lee et al. | |
| 5,037,651 A | 8/1991 | Lee | |
| 5,053,394 A | 10/1991 | Ellestad et al. | |
| 5,079,233 A | 1/1992 | Lee | |

(Continued)

FOREIGN PATENT DOCUMENTS

| | | |
|---|---|---|
| EP | 0 239 400 | 8/1994 |
| EP | 0 425 235 | 9/1996 |

(Continued)

OTHER PUBLICATIONS

Wayback machine found at: https://archive.org/web/ (Year: 2018).*

(Continued)

*Primary Examiner* — Gregory S Emch
*Assistant Examiner* — Ashley H. Gao
(74) *Attorney, Agent, or Firm* — Grüneberg and Myers PLLC

(57) ABSTRACT

The invention provides methods of depleting CD5+ cells in human patients undergoing chimeric antigen receptor (CAR) immunotherapy in order to promote acceptance of CAR expressing immune cells. Anti-CD5 antibody drug conjugates (ADCs) are administered as a conditioning regimen to a human patient receiving autologous or allogeneic CAR expressing immune cells such that the CAR expressing immune cells are accepted by the human patient. Compositions and methods of the invention can be used in combination with CAR therapy to treat a variety of pathologies, including autoimmune diseases and cancer.

30 Claims, 9 Drawing Sheets
Specification includes a Sequence Listing.

(56) References Cited

U.S. PATENT DOCUMENTS

| | | |
|---|---|---|
| 5,122,368 A | 6/1992 | Greenfield et al. |
| 5,208,020 A | 5/1993 | Chari et al. |
| 5,225,539 A | 7/1993 | Winter |
| 5,359,046 A | 10/1994 | Capon et al. |
| 5,416,064 A | 5/1995 | Chari et al. |
| 5,475,092 A | 12/1995 | Chari et al. |
| 5,530,101 A | 6/1996 | Queen et al. |
| 5,565,332 A | 10/1996 | Hoogenboom et al. |
| 5,585,089 A | 12/1996 | Queen et al. |
| 5,585,499 A | 12/1996 | Chari et al. |
| 5,621,002 A | 4/1997 | Bosslet et al. |
| 5,622,929 A | 4/1997 | Willner et al. |
| 5,635,483 A | 6/1997 | Pettit et al. |
| 5,648,237 A | 7/1997 | Carter |
| 5,663,149 A | 9/1997 | Pettit et al. |
| 5,686,281 A | 11/1997 | Roberts |
| 5,693,761 A | 12/1997 | Queen et al. |
| 5,693,762 A | 12/1997 | Queen et al. |
| 5,712,374 A | 1/1998 | Kuntsmann et al. |
| 5,714,586 A | 2/1998 | Kuntsmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,807,715 A | 9/1998 | Morrison et al. |
| 5,824,805 A | 10/1998 | King et al. |
| 5,840,523 A | 11/1998 | Simmons et al. |
| 5,846,545 A | 12/1998 | Chari et al. |
| 5,877,296 A | 3/1999 | Hamann et al. |
| 5,994,619 A | 11/1999 | Stice et al. |
| 6,103,521 A | 8/2000 | Capon et al. |
| 6,180,370 B1 | 1/2001 | Queen et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,333,410 B1 | 12/2001 | Chari et al. |
| 6,441,163 B1 | 8/2002 | Chari et al. |
| 6,677,435 B2 | 1/2004 | Barbas, III et al. |
| 6,716,821 B2 | 4/2004 | Zhao et al. |
| 6,759,509 B1 | 7/2004 | King et al. |
| 6,835,807 B1 | 12/2004 | Susaki et al. |
| 7,223,837 B2 | 5/2007 | De Groot et al. |
| 7,276,497 B2 | 10/2007 | Chari et al. |
| 7,276,697 B2 | 10/2007 | Devine |
| 7,368,565 B2 | 5/2008 | Chari et al. |
| 7,473,796 B2 | 1/2009 | Chari et al. |
| 7,521,541 B2 | 4/2009 | Eigenbrot et al. |
| 7,754,681 B2 | 7/2010 | Feng |
| 8,236,319 B2 | 8/2012 | Chari et al. |
| 9,233,173 B2 | 1/2016 | Faulstich et al. |
| 9,328,156 B2 | 5/2016 | June et al. |
| 9,399,681 B2 | 7/2016 | Anderl et al. |
| 9,504,756 B2 | 11/2016 | Lyon et al. |
| 9,573,988 B2 | 2/2017 | Brogdon et al. |
| 9,636,421 B2 | 5/2017 | Verkade et al. |
| 9,676,702 B2 | 6/2017 | Lutz et al. |
| 9,714,278 B2 | 7/2017 | June et al. |
| 9,765,156 B2 | 9/2017 | June et al. |
| 9,783,591 B2 | 10/2017 | June et al. |
| 10,040,865 B2 | 8/2018 | Scheinberg et al. |
| 10,117,896 B2 | 11/2018 | Powell, Jr. et al. |
| 10,221,245 B2 | 3/2019 | Brogdon et al. |
| 10,308,717 B2 | 6/2019 | Brogdon et al. |
| 2003/0096743 A1 | 5/2003 | Senter et al. |
| 2003/0130189 A1 | 7/2003 | Senter et al. |
| 2004/0018194 A1 | 1/2004 | Francisco et al. |
| 2004/0052793 A1 | 3/2004 | Carter et al. |
| 2004/0121940 A1 | 6/2004 | De Groot et al. |
| 2005/0169933 A1 | 8/2005 | Steeves et al. |
| 2005/0238649 A1 | 10/2005 | Doronina et al. |
| 2005/0256030 A1 | 11/2005 | Feng |
| 2008/0254027 A1* | 10/2008 | Bernett ............... A61P 35/02 435/375 |
| 2013/0288373 A1 | 10/2013 | Verstraete et al. |
| 2014/0294865 A1 | 10/2014 | Simon et al. |
| 2014/0369974 A1* | 12/2014 | Reisner ............... A61P 7/00 424/93.7 |
| 2015/0079114 A1 | 3/2015 | Ohtsuka et al. |
| 2015/0218220 A1 | 8/2015 | Mendelsohn et al. |
| 2016/0002298 A1 | 1/2016 | Müller et al. |
| 2016/0046724 A1 | 2/2016 | Bragdon et al. |
| 2016/0303166 A1* | 10/2016 | Katz ............... A61P 1/16 |
| 2016/0303254 A1 | 10/2016 | Kolakowski et al. |
| 2017/0298145 A1 | 10/2017 | Verkade et al. |
| 2017/0368101 A1* | 12/2017 | Bot ............... A61K 38/2013 |
| 2018/0044424 A1 | 2/2018 | June et al. |
| 2018/0256712 A1 | 9/2018 | June et al. |
| 2018/0258149 A1 | 9/2018 | Motz et al. |
| 2018/0271907 A1* | 9/2018 | June ............... A61K 35/12 |
| 2018/0273601 A1 | 9/2018 | Adusumilli et al. |
| 2019/0144504 A1 | 5/2019 | Burger et al. |
| 2019/0151363 A1 | 5/2019 | Brentjens et al. |

FOREIGN PATENT DOCUMENTS

| | | | |
|---|---|---|---|
| EP | 0 349 578 | 10/1998 | |
| EP | 0 527 839 | 12/1998 | |
| EP | 0 592 106 | 11/2004 | |
| EP | 0 519 596 | 2/2005 | |
| EP | 0 589 877 | 10/2005 | |
| WO | 91/09967 | 7/1991 | |
| WO | 98/13059 | 4/1998 | |
| WO | 02/088172 | 11/2002 | |
| WO | 2004/032828 | 4/2004 | |
| WO | 2005/037992 | 4/2005 | |
| WO | 2005/081711 | 9/2005 | |
| WO | 2006/034488 | 3/2006 | |
| WO | WO-2008121160 A2 * | 10/2008 | ............ A61P 35/02 |
| WO | 2010/009124 | 1/2010 | |
| WO | WO-2016090034 A2 * | 6/2016 | ............ A61K 31/436 |
| WO | 2016/191756 | 12/2016 | |
| WO | WO-2016191756 A1 * | 12/2016 | ............ A61K 31/664 |
| WO | 2017/149077 | 9/2017 | |
| WO | WO-2018115466 A1 * | 6/2018 | ......... A61K 47/6831 |
| WO | 2019/108863 | 6/2019 | |

OTHER PUBLICATIONS

Hoffmann, RM, et al, Antibody structure and engineering considerations for the design and function of Antibody Drug Conjugates (ADCs). Oncoimmunology. Nov. 20, 2017;7(3):e1395127. doi: 10.1080/2162402X.2017.1395127. (Year: 2015).*

Su W, Yeong KF, Spencer JImmunohistochemical analysis of human CD5 positive B cells: mantle cells and mantle cell lymphoma are not equivalent in terms of CD5 expressionJournal of Clinical Pathology 2000;53:395-397. (Year: 2000).*

Kingma, DW, et al., CD2 is expressed by a subpopulation of normal B cells and is frequently present in mature B-cell neoplasms. Cytometry. Oct. 15, 2002;50(5):243-8. doi: 10.1002/cyto. 10131. PMID: 12360573 (Year: 2002).*

Frequently Asked Questions About CAR T-Cell Therapy, Dana-Farber Cancer Institue (Year: 2018).*

Brudno, Allogeneic T Cells That Express an Anti-CD19 Chimeric Antigen Receptor Induce Remissions of B-Cell Malignancies That Progress After Allogeneic Hematopoietic Stem-Cell Transplantation Without Causing Graft-Versus-Host Disease. Apr. 1, 2016;34(10):1112-21.doi: 0.1200/JCO.2015.64.5929. (Year: 2016).*

Hermanson, DL, et al, Utilizing chimeric antigen receptors to direct natural killer cell activity, Front. Immunol., Apr. 28, 2015 Sec. NK and Innate Lymphoid Cell Biology vol. 6—2015 | https://doi.org/10.3389/fimmu.2015.00195 (Year: 2015).*

Chen H, Lin Z, Arnst KE, Miller DD, Li W. Tubulin Inhibitor-Based Antibody-Drug Conjugates for Cancer Therapy. Molecules. Aug. 1, 2017;22(8):1281. doi: 10.3390/molecules22081281. PMID: 28763044; PMCID: PMC6152078. (Year: 2017).*

(56) References Cited

OTHER PUBLICATIONS

Kaveh Matinkhoo, Alla Pryyma, Mihajlo Todorovic, Brian O. Patrick, and David M. Perrin Journal of the American Chemical Society 2018 140 (21), 6513-6517 DOI: 10.1021/jacs.7b12698 (Year: 2018).*
Hudecek, M., et al, The Nonsignaling Extracellular Spacer Domain of Chimeric Antigen Receptors is Decisive for In Vivo Antitumor Activity, Cancer Immunol Res (2015) 3 (2): 125-135. https://doi.org/10.1158/2326-6066.CIR-14-0127 (Year: 2015).*
Thrive Cancer Blog, "Colorectal Cancer That Has Spread to the Liver: What You Should know", Fox Chase Cancer Center, Temple University Health System, Inc., Nov. 20, 2020, 5 pages.
Geyer et al., "Review: Current Clinical Applications of chimeric antigen receptor (CAR) modified T cells", Cytotherapy, vol. 18, Issue 11, Nov. 2016, pp. 1393-1409.
Bird et al., "Single-Chain Antigen-Bind Proteins", Science, vol. 242, Oct. 21, 1988, pp. 423-426.
Huston et al., "Protein engineering of antibody binding sites: Recovery of specific activity in an anti-digoxin single-chain Fv analogue produced in *Escherichia coli*" Proc. Natl. Acad. Sci. USA, vol. 85, Aug. 1988, pp. 5879-5883.
Morrison, "Transfectomas Provide Novel Chimeric Antibodies", Science, vol. 229, Issue 4719, Sep. 20, 1985, pp. 1202-1207.
Gillies et al., "High level expression of chimeric antibodies using adapted cDNA variable region cassettes" J. Immunol. Methods, vol. 125, Aug. 30, 1989, pp. 191-202.
Riechmann et al., "Reshaping human antibodies for therapy" Nature vol. 332, Mar. 24, 1988, pp. 323-327.
Eduardo A. Padlan, "A possible procedure for Reducing the Immunogenicity of Antibody Variable Domains while Preserving their Ligand-Binding properties" Molecular Immunology, vol. 28, No. 4/5, Apr.-May 1991, pp. 489-498.
Studnicka et al., "Human-engineered monoclonal antibodies retain full specific binding activity by preserving non-CDR complementary-modulating residues", Protein Engineering, vol. 7, No. 6, Jun. 1994, pp. 805-814.
Roguska et al., "Humanization of murine monoclonal antibodies through variable domain resurfacing", Proc. Natl. Acad. Sci., vol. 91, Feb. 1994, pp. 969-973.
Leriche et al., "Cleavable Linkers in chemical biology", Bioorganic & Medicinal Chemistry, vol. 20, Jan. 2012, pp. 571-582.
Theodor Wieland, "The toxic peptides from Amanita mushrooms", Int. J. Pept. Protein Res., vol. 22, No. 3, Jan. 15, 1983, pp. 257-276.
Matinkhoo et al., "Synthesis of the Death-Cap Mushroom Toxin α-Amanitin", J. Am. Chem. Soc., vol. 140, Mar. 21, 2018, pp. 6513-6517.
Guedan et al., "Engineering and Design of Chimeric Antigen Receptors", Molecular Therapy-Methods & Clinical Development, vol. 12, Mar. 2019, pp. 145-156.
Sadelain et al., "The Basic Principles of Chimeric Antigen Receptor Design" Cancer Discovery, Apr. 2013, pp. 388-398.
Nicholson et al., "Construction and Characterization of a Functional CD19 Specific Single Chain Fv Fragment for Immunotherapy of B Lineage Leukemia and Lymphoma", Molecular Immunology, vol. 34, No. 16-17, Nov.-Dec. 1997, pp. 1157-1165.
Gladkikh et al., "Comparison of the mRNA expression profile of B-cell receptor components in normal CD5-high B-lymphocytes and chronic lymphocytic leukemia: a key role of ZAP70", Cancer Medicine, vol. 6, No. 12, Dec. 2017, pp. 2984-2997.
Jones et al., "Isolation of complementary DNA clones encoding the human lymphocyte glycoprotein T1/Leu-1", Nature, vol. 323, No. 25, Sep. 1986, pp. 346-349.
Felici et al., "Peptide and protein display on the surface of filamentous bacteriophage", Biotechnology Annual Review, vol. 1, 1995, pp. 149-183.
Bardley A. Katz, "Structural and mechanistic determinants of affinity", Annu Rev. Biophys. Biomol. Struct., vol 26, Jun. 1997, pp. 27-45.
Hoogenboom et al., "Antibody phage display technology and its applications", Immunotechnology, vol. 4, Jun. 1998, pp. 1-20.
Brian K. Kay, "Biologically displayed random peptides as reagents in mapping protein-protein interactions", Perspectives Drug Discovery Design, vol. 2, Apr. 1995, pp. 251-268.
Kay et al., "High-throughput screening strategies to identify inhibitors of protein-protein-protein interactions", Molecular Diversity, vol. 1, Feb. 1996, pp. 139-140.
Chiswell et al., "Phage antibodies: will new 'coliclonal' antibodies replace monoclonal antibodies?", TIBTECH, vol. 10, Mar. 1992, pp. 80-84.
McCafferty et al., "Phage antibodies: filamentous phage displaying antibody variable domains", Nature, vol. 348, Dec. 6, 1990, pp. 552-554.
Barbas III et al., "Assembly of combinatorial antibody libraries on phage surfaces: The gene III site", Proc. Natl. Acad. Sci. USA, vol. 88, Sep. 1991, pp. 7978-7982.
Clackson et al., "Making antibody fragments using phage display libraries", Nature, vol. 352, Aug. 15, 1991, pp. 624-628.
Williams et al., "Cell-based selectin of internalizing fully human antagonistic antibodies directed against FLT3 for suppression of leukemia cell growth", Leukemia, vol. 19, Jun. 2, 2005, pp. 1432-1438.
Keith A. Charlton, "Expression and Isolation of recombinant Antibody Fragments in *E. coli*", Methods in Molecular Biology, vol. 248, Antibody Engineering: Methods and Protocols, vol. 248, Edited by B.K.C. Lo, Humana Press, 2004, pp. 245-254.
F.L. Graham et al., "Characteristics of Human Cell line Transformed by DNA from Human Adenovirus Type 5", J. Gen Virol., vol. 36, Issue 1, Jul. 1, 1977, pp. 59-74.
Jennie P. Mather, "Establishment and Characterization of two Distinct mouse Testicular Epithelial Cell Lines", Biology of Reproductions, vol. 23, Aug. 1980, pp. 243-251.
Mather et al., "Culture of Testicular Cells in Hormone-Supplemented Serum-Free Medium", Annals N.Y. Acad. Sci., vol. 383, Jun. 1982, pp. 44-68.
Urlaub et al., "Isolation of Chinese hamster cell mutants deficient in dihydrofolate reductase activity", Proc. Natl. Acad. Sci. USA, vol. 77, No. 7, Jul. 1980, pp. 4216-4220.
Paul J. Yazaki-et-al., "Expression of Recombinant Antibodies in Mammalian Cell Lines", Methods in Molecular Biology, vol. 248: Antibody Engineering: Methods and Protocols, Edited by B.K.L, Humana Press, 2004, pp. 255-268.
Zanotti et al., "Synthesis of analogues of amaninamide, an amatoxin from the white Amanita virosa mushroom", Int J. Peptide and Protein Res., vol. 30, Jan. 30, 1987, pp. 450-459.
Woyke et al, "In Vitro Activities and Postantifungal Effects of the Potent Dolastatin 10 Derivative Auristation PHE", Antimicrobial Agents Chemotherapy vol. 45, No. 12, Dec. 2001, pp. 3580-3584.
Pettit et al., "Specific Activities of Dolastatin 10 and Peptide Derivates against Cryptococcus neoformans", Antimicrobial Agents Chemotherapy, vol. 42, Nov. 1998, pp. 2961-2965.
Pettit et al., "The Absolute Configuration and Synthesis of Natural (−)-Dolastatin 10[1]", J. Am. Chem. Soc., vol. 111, Jul. 1, 1989, pp. 5463-5465.
Pettit et al., "Antineoplastic agents 365, Dolastatin 10 SAR probes", Anti-Cancer Drug Design, vol. 13, Jun. 1, 1998, pp. 243-277.
Pettit, et al., "The Dolastatins; 18: Stereospecific Synthesis of Dolaproine[1]", Synthesis, Jun. 1996, pp. 719-725.
Pettit, et al., "Dolastatins 24. Synthesis of (−)-dolastatin 10. [1] X-Ray molecular structure of N,N-dimethylvalyl-valyl-dolaisoleuine *tert*-butyl ester", J. Chem. Soc., Perkin 1, 1996, pp. 859-863.
Doronina, et al., "Development of potent monoclonal antibody auristatin conjugates for cancer therapy", Nature Biotechnology, vol. 21, No. 7, Jul. 2003, pp. 778-784.
Chari, et al., "Immunoconjugates Containing Novel Maytansinoids: Promising Anticancer Drugs", Cancer Research, 52, Jan. 1, 1992, pages 127-131.
N.R.Bachur, Free Radical Damage, Anthracycline Antibiotics in Cancer Therapy, Proceedings of the International Symposium on Anthracycline Antibiotics in Cancer Therapy, Sep. 16-18, 1981, pp. 97-102, (26 pages).
C. Peterson, et al. "Transport and Storage of Anthracyclines in Experimental Systems and Human Leukemia", Anthracycline Anti-

(56) References Cited

OTHER PUBLICATIONS biotics in Cancer Therapy, Proceedings of the International Symposium on Anthracycline Antibiotics in Cancer Therapy, Sep. 16-18, 1981, pp. 132-146, (35 pages).
Sessa, et al., "Ongoing phase I and II studies of novel anthracyclines", Cardiovasc. Toxicolo. May 22, 2007, pp. 75-79.
Quintieri, et al., "Formation and Antitumor Activity of PNU-159682, A Major Metabolite of Nemorubicin in Human Liver Microsomes", Clinical Cancer Research, vol. 11, Feb. 15, 2005, pp. 1608-1617.
John A Hartley, "The development of pyrrolobenzodiazepines as antitumour agents", Expert Opinion on Investigational Drugs, 20, 6, Apr. 4, 2011, pp. 733-744.
Antonow, et al., "Synthesis of DNA-Interactive Pyrrolo[2,1-c][1,4]benzodiazepines (PBDs)", Chemical Reviews, Dec. 17, 2010, pp. 2815-2864.
Sutherland, et al., "SGN-CD33A: a novel CD33-targeting antibody-drug conjugate using a pyrrolobenzodiazepine dimer is active in models of drug-resistant AML", Blood, The American Society of Hematology, Aug. 22, 2013, vol. 122, No. 8, pp. 1455-1463.
Tiberghien, et al., "Design and Synthesis of Tesirine, a Clinical Antibody-Drug Conjugate Pyrrolobenzodiazepine Dimer Payload", ACS Medical Chemistry Letters, May 24, 2016, pp. 983-987.
Mantaj, et al., "From Anthramycin to Pyrrolobenzodiazepine (PBD)-Containing Antibody-Drug Conjugates (ADCs)", Angewandte Chemie, International Editon, Pyrrolobenzodiazepines, Jan. 9, 2017, vol. 56, pp. 462-488.
Hinman, et al., "Preparation and Characterization of Monoclonal Antibody Conjugates of the Calicheamicins: A Novel and Potent Family of Antitumor Antibiotics", Cancer Research, 53, Jul. 15, 1993, pp. 3336-3342.
Lode, et al., "Targeted Therapy with a Novel Enediyene Antibiotic Calicheamicin $\Theta^1_1$, Effectively Suppresses Growth and Dissemination of Liver Metastases in a Syngeneic Model of Murine Neuroblastoma[1]", Cancer Research, 58, Jul. 15, 1998, pp. 2925-2928.
Greg T. Hermanson, "Bioconjugate Techniques", Second Edition, Jul. 26, 2010, 1233 pages.
Dubowchik, et al., "Receptor-mediated and enzyme-dependent targeting of cytotoxic anticancer drugs", Pharmacology & Therapeutics, 83, Aug. 1, 1999, pp. 67-123.
Neville, et al., "Enhancement of Immunotoxin Efficacy by Acid-cleavable Crosslinking Agents Utilizing Diphtheria Toxin and Toxin Mutants*", The Journal of Biological Chemistry, vol. 264, No. 25, Issue of Sep. 5, 1989, pp. 14653-14661.

Thorpe, et al., "New Coupling Agents for the Synthesis of Immunotoxins Containing a Hindered Disulfide Bond with Improved Stability in Vivo", Cancer Research, 47, Nov. 15, 1987, pp. 5924-5931.
Jain, et al., "Current ADC Linker Chemistry", Pharm. Res., Mar. 11, 2015, pp. 3526-3540.
Carl et-al., Journal of Medicinal Chemistry, vol. 24, No. 5, May 1981, Communication to the Editor, 2 pages.
Chakravarty, et al., "Plasmin-Activated Prodrugs for Cancer Chemotherapy. 2. Synthesis and Biological Activity of Peptidyl Derivatives of Doxorubicin", Journal of Medicinal Chemistry, May 1983, vol. 26, No. 5, pp. 638-644.
Hay, et al., "A 2-nitroimidazole carbamate prodrug of 5-amino-1-(chloromethyl)-3-[(5,6,7-trimethoxyindol-2-yl)carbonyl]-1,2-dihydro-3H-benz[e]indole (amino-*seco*-CBI-TMI) for use with ADEPT and GDEPT", Bioorganic & Medicinal Chemistry Letters, vol. 9, Aug. 2, 1999, pp. 2237-2242.
De Groot, et al., "Elongated Multiple Electronic Cascade and Cyclization Spacer Systems in Activatible Anticancer Prodrugs for Enhanced Drug Release", J.Org. Chem., 66, 26, Dec. 28, 2001, pp. 8815-8830.
Liu, et al., "New Procedures for Preparation and Isolation of Conjugates of Proteins and a Synthetic Copolymer of D-Amino Acids and Immunochemical Characterization of Such Conjugates", Biochemistry, 18, 4, Feb. 20, 1979, pp. 690-697.
Doronina, et al., "Enhanced Activity of Monomethylauristatin F through Monoclonal Antibody Delivery: Effects of Linker Technology on Efficacy and Toxicity", Bioconjugate Chem., 17, 1, Jan.-Feb. 2006, pp. 114-124.
Laguzza, et al., "New Antitumor Monoclonal Antibody-Vinca Conjugates LY203725 and Related Compounds: Design, Preparation, and Representative in Vivo Activity[1]", J. Med. Chem., 32, Mar. 1989, pp. 548-555.
Turtle, et al., "CD19 CAR-T cells of defined $CD4^+$:$CD8^+$ composition in adult B cell ALL patients", The Journal of Clinical Investigation, vol. 126, No. 6, Jun. 1, 2016, pp. 2123-2138.
Hay, et al., "Chimeric Antigen Receptor (CAR) T Cells: Lessons Learned from Targeting of CD19 in B-Cell Malignancies", Drugs, Jan. 21, 2017, pp. 237-245.
Hill, et al., "Infectious complications of CD19-targeted chimeric antigen receptor-modified T-cell immunotherapy", Immunobiology and Immunotherapy, vol. 131, No. 1, Jan. 4, 2018, pp. 121-130.
Wei, et al., "Advances of CD19-directed chimeric antigen receptor-modified T cells in refractory/relapsed acute lymphoblastic leukemia", Experimental Hematology & Oncology, Apr. 14, 2017, pp. 1-7.
Extended European Search Report dated Jul. 21, 2022, in Patent Application No. 19842155.4, 9 pages.

* cited by examiner

USE OF ANTI-CD5 ANTIBODY DRUG CONJUGATE (ADC) IN ALLOGENEIC CELL THERAPY

RELATED APPLICATIONS

This application is a continuation of PCT Application No. PCT/US2019/043125, filed on Jul. 23, 2019, which claims priority to U.S. Provisional Patent Application No. 62/702,296, filed on Jul. 23, 2018, and U.S. Provisional Patent Application No. 62/773,047, filed on Nov. 29, 2018. The entire contents of the foregoing applications are hereby incorporated by reference.

SEQUENCE LISTING

The instant application contains a Sequence Listing which has been submitted electronically in ASCII format and is hereby incorporated by reference in its entirety. Said ASCII copy, created on Jan. 21, 2021, is named M103034_2060US.C1_SL.txt and is 85,167 bytes in size.

FIELD OF THE INVENTION

The present invention generally relates to methods for promoting acceptance of an immune cell expressing a chimeric antigen receptor (CAR) in a human subject through the use of an anti-CD5 antibody-drug conjugate (ADC).

BACKGROUND OF THE INVENTION

Chimeric antigen receptor (CAR) therapy is an immunological treatment that uses the body's own immune system to destroy cells expressing a specific antigen associated with a certain disease, such as cancer. In cancer, for example, CAR therapy enlists and strengthens the power of a patient's immune system to attack tumors. Over the past several years, this immunotherapy has emerged as a promising and revolutionary therapy. CAR therapy is based on an immune cell, such as a T cell, expressing a CAR which is generally a transmembrane fusion protein that combines an extracellular antigen binding domain, such as scFv, with cytoplasmic activity signaling and "co-stimulatory" domains that signal the cell from the surface receptor. Thus, when immune cells, such as T-cells, express CARs, the immune cells are able to recognize and kill cells that express the antigen targeted by the antigen binding domain of the CAR (e.g., a tumor associated antigen) (Geyer and Brentjens (2016) *Cytotherapy* 18(11): 1393-1409).

While CAR therapy is an incredibly powerful technology, it does come with serious risks and adverse side effects (Kay and Turtle (2017) *Drugs* 77(3):237-245; Hill et al. (2018) *Blood* 131:121-130). Lymphodepleting chemotherapy is commonly used as a conditioning treatment in combination with CAR therapy in order to minimize the rejection of the CAR expressing cells by the patient receiving treatment (Wei et al. (2017) *Exp Hematol Oncol.* 6: 10). For example, the combination of lymphodepleting agents fludarabine and cyclophosphamide improved duration of CAR-T cells in recipient patients (Turtle et al. (2016) *J Clinic Invest* 126 (6):2123; see also US 20170368101). While conditioning therapy has improved the efficacy of CAR-T cells, lymphodepleting chemotherapy often has serious negative side effects.

SUMMARY OF THE INVENTION

The present invention provides a conditioning regimen which can be used with CAR therapy to promote acceptance of CAR expressing immune cells. The methods described herein can be used to promote acceptance of either autologous CAR expressing immune cells or allogeneic CAR expressing immune cells. Traditionally acceptance of such cells has been achieved using lymphodepleting chemotherapeutic treatment. Described herein are improved methods of promoting acceptance of CAR expressing cells in a recipient patient.

Included in the invention is a method of promoting acceptance of an immune cell expressing a chimeric antigen receptor (CAR) in a human subject having cancer or an autoimmune disease, the method comprising administering an anti-CD5 antibody drug conjugate (ADC) to a human subject having cancer or an autoimmune disease, wherein the anti-CD5 ADC comprises an anti-CD5 antibody, or antigen-binding fragment thereof, conjugated to a cytotoxin via a linker; and administering a therapeutically effective amount of an immune cell expressing a CAR to the human subject, wherein the CAR comprises an extracellular domain that binds to a tumor antigen or an antigen associated with an autoimmune disease, a transmembrane domain, and a cytoplasmic domain.

In one embodiment, the human subject is not administered alemtuzumab prior to, concomitantly with, or following administration of the immune cell expressing a CAR. In another embodiment, the human subject is not administered a lymphodepleting chemotherapeutic agent prior to, concomitantly with, or following administration of the immune cell expressing a CAR. In one embodiment, the lymphodepleting chemotherapeutic agent is fludarabine, cyclophosphamide, bendamustine, and/or pentostatin.

In one embodiment, the method further comprises administering an anti-CD5 ADC to the human subject prior to administration of the immune cell expressing a CAR.

In one embodiment, the method further comprises administering the anti-CD5 ADC to the human subject about 12 hours to about 21 days before administration of the immune cell expressing a CAR.

In one embodiment, the immune cell is an allogeneic cell or an autologous cell. In one embodiment, the allogeneic cell is an allogeneic T cell or an allogeneic NK cell.

In certain embodiments, the therapeutically effective amount of the allogeneic cell expressing the CAR is about $1 \times 10^4$ to about $1.0 \times 10^8$ cells/kg.

The invention further features a method of treating a patient having a tumor comprising administering an anti-CD5 ADC to a patient in need thereof, wherein the anti-CD5 ADC comprises an anti-CD5 antibody, or antigen-binding fragment thereof, conjugated to a cytotoxin via a linker, and administering to the patient a therapeutically effective amount of from about $1 \times 10^6$ to about $1 \times 10^8$ engineered CAR T cells/kg. In one embodiment, the therapeutically effective amount of the engineered CAR T cells is about $1 \times 10^6$ or about $2 \times 10^6$ cells/kg.

In certain embodiments of the invention, the anti-CD5 ADC is administered to the patient as a single dose or as multiple doses.

In one embodiment, the anti-CD5 antibody, or antigen-binding fragment thereof, comprises a heavy chain variable region comprising a CDR1, a CDR2, and a CDR3 having an amino acid sequence as set forth in SEQ ID NOs: 3, 4, and 5, respectively, and comprises a light chain variable region comprising a CDR1, a CDR2, and a CDR3 having an amino acid sequence as set forth in SEQ ID NOs: 6, 7, and 8, respectively.

In one embodiment, the anti-CD5 antibody, or antigen-binding fragment thereof, is chimeric or humanized.

In another embodiment, the anti-CD5 antibody, or antigen-binding fragment thereof, is an IgG1 isotype or an IgG4 isotype.

In yet another embodiment, the cytotoxin is an antimitotic agent or an RNA polymerase inhibitor.

In other embodiments, the cytotoxin is a maytansine, a calicheamicin, a pyrrolobenzodiazepine, an indolinobenzodiazepine, or an auristatin. In one embodiment, the auristatin is monomethyl auristatin F (MMAF) or monomethyl auristatin E (MMAE). In one embodiment, the cytotoxin is a maytansine. In one embodiment, the cytotoxin is a pyrrolobenzodiazepine (PBD). For example, in some embodiments, the PBD may selected from tesirine or talirine. In some embodiments, the cytotoxin may be a calicheamicin. For example, in some embodiments, the calicheamicin may be ozogamicin.

In one embodiment, the RNA polymerase inhibitor is an amatoxin. In another embodiment, the RNA polymerase inhibitor is an amanitin (e.g., α-amanitin, β-amanitin, γ-amanitin, ε-amanitin, amanin, amaninamide, amanullin, amanullinic acid, or proamanullin).

In one embodiment, the antibody-drug conjugate (ADC) is represented by the formula Ab-Z-L-Am, wherein Ab is an antibody or antigen-binding fragment thereof that binds CD5, L is a linker, Z is a chemical moiety, and Am is an amatoxin. In certain embodiments, the linker-amatoxin conjugate Am-L-Z is represented by formula (III)

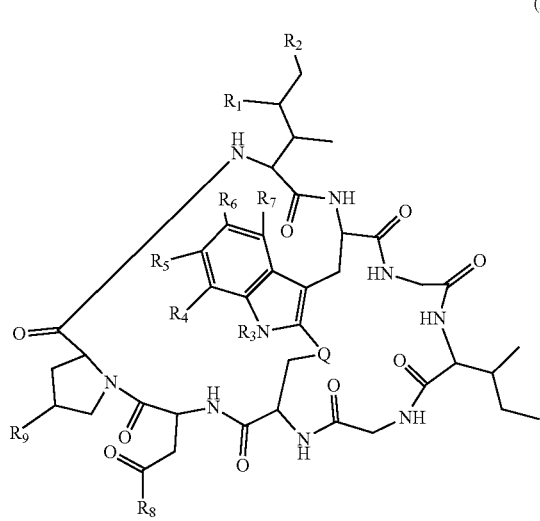

(III)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
Q is —S—, —S(O)—, or —SO$_2$—
$R_C$ is -L-Z;
$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;
L is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl; or comprises a dipeptide; or —(($CH_2$)$_m$O)$_n$($CH_2$)$_m$—, where m and n are each independently selected from 1, 2, 3, 4, 5, 6, 7, 8, 9, and 10; and
Z is a chemical moiety formed from a coupling reaction between a reactive substituent present on L and a reactive substituent present within the anti-CD5 antibody or antigen-binding fragment thereof.

In this embodiment, the linker-amatoxin conjugate Am-L-Z is represented by formula (III)

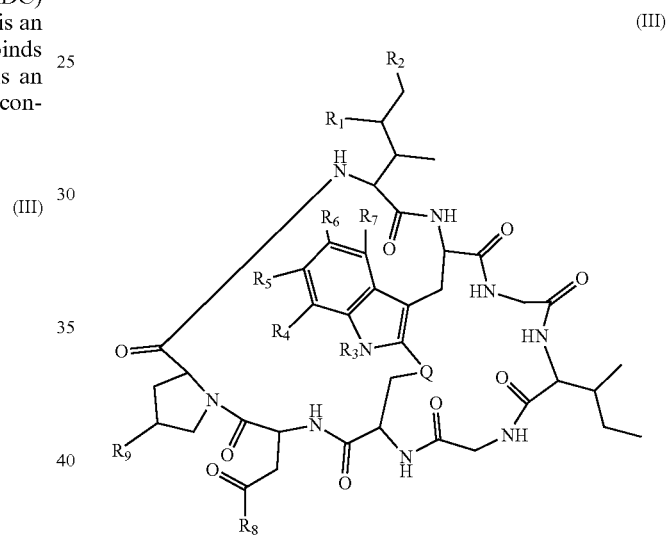

(III)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
Q is —S—, —S(O)—, or —SO$_2$—
$R_C$ is -L-Z;
$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;
L is a linker; and
Z is a chemical moiety formed from a coupling reaction between a reactive substituent present on L and a reactive substituent present within the anti-CD5 antibody or antigen-binding fragment thereof.

In one embodiment of Formula (III), L is a peptide containing linker.

In some embodiments, the linker comprises one or more of a dipeptide, a p-aminobenzyl (PAB) group, an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted $C_2$-$C_6$ alkynyl, an optionally substituted $C_2$-$C_6$ heteroalkynyl, an optionally substituted $C_3$-$C_6$ cycloalkyl, an optionally substituted heterocycloalkyl, an optionally substituted aryl, an optionally substituted heteroaryl, a solubility enhancing group, —(C=O)—, a —($CH_2CH_2O$)$_p$— group, wherein p is an integer from 1-6, (($CH_2$)$_m$O)$_n$ ($CH_2$)$_m$—, where n and each m are each independently selected from 1, 2, 3, 4, 5, 6, 7, 8, 9, and 10; or a combination thereof.

In some embodiments, the linker comprises a (($CH_2$)$_m$O)$_n$($CH_2$)$_m$ group and a heteroaryl group, wherein the heteroaryl group is a triazole. In some embodiments, the (($CH_2$)$_m$O)$_n$($CH_2$)$_m$ group and triazole together comprise

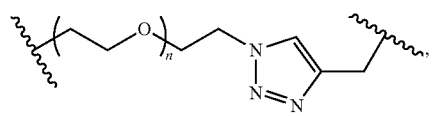

where n is from 1 to 10, and the wavy lines indicate attachment points to additional linker components, the chemical moiety Z, or the amatoxin.

In some embodiments, Am contains exactly one $R_C$ substituent.

In one embodiment, the linker of the ADC is N-beta-maleimidopropionyl-Val-Ala-para-aminobenzyl (BMP-Val-Ala-PAB). In some embodiments, the linker L and the chemical moiety Z, taken together as L-Z, is

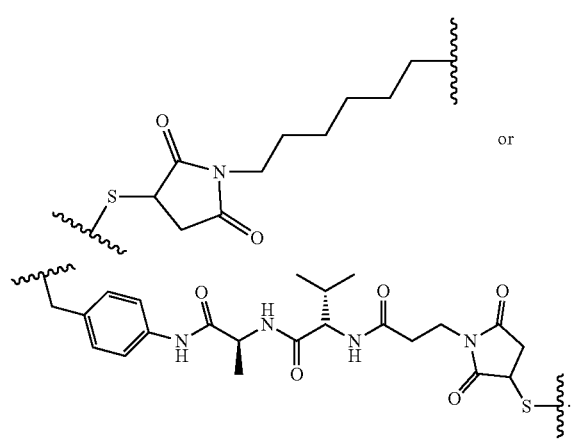

where S is a sulfur atom which represents the reactive substituent present within an antibody, or antigen-binding fragment thereof, that binds CD5 (e.g., from the —SH group of a cysteine residue).

In some embodiments, L-Z is

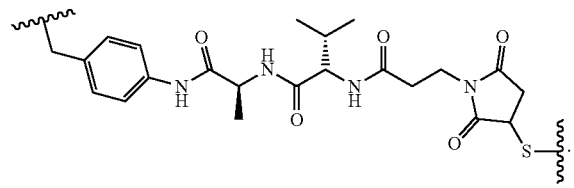

In one embodiment, the ADC is represented by any one of the following structures:

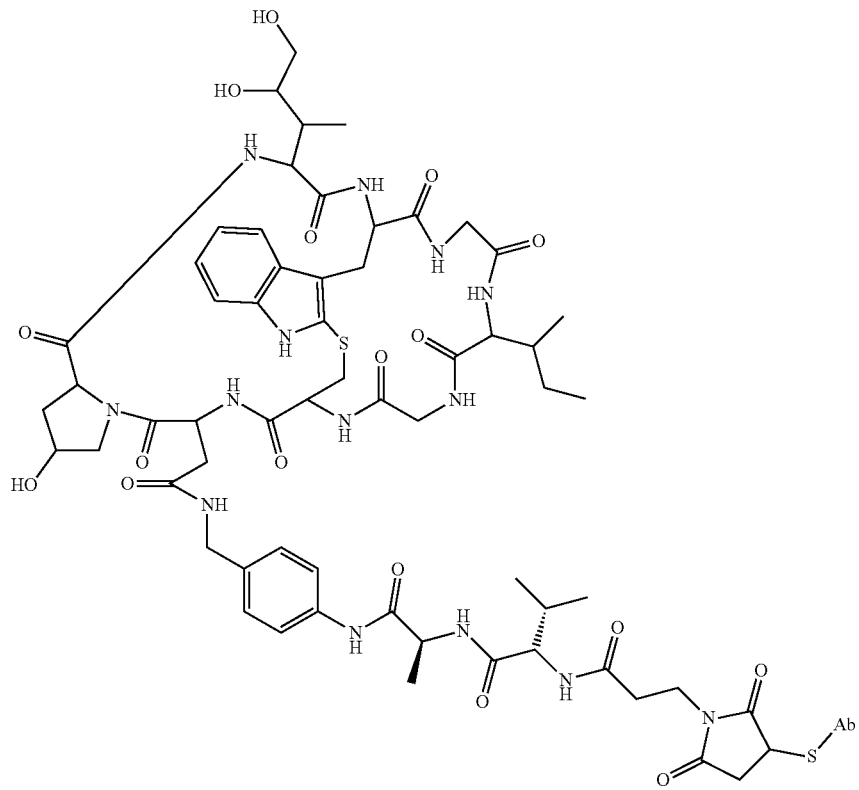

-continued
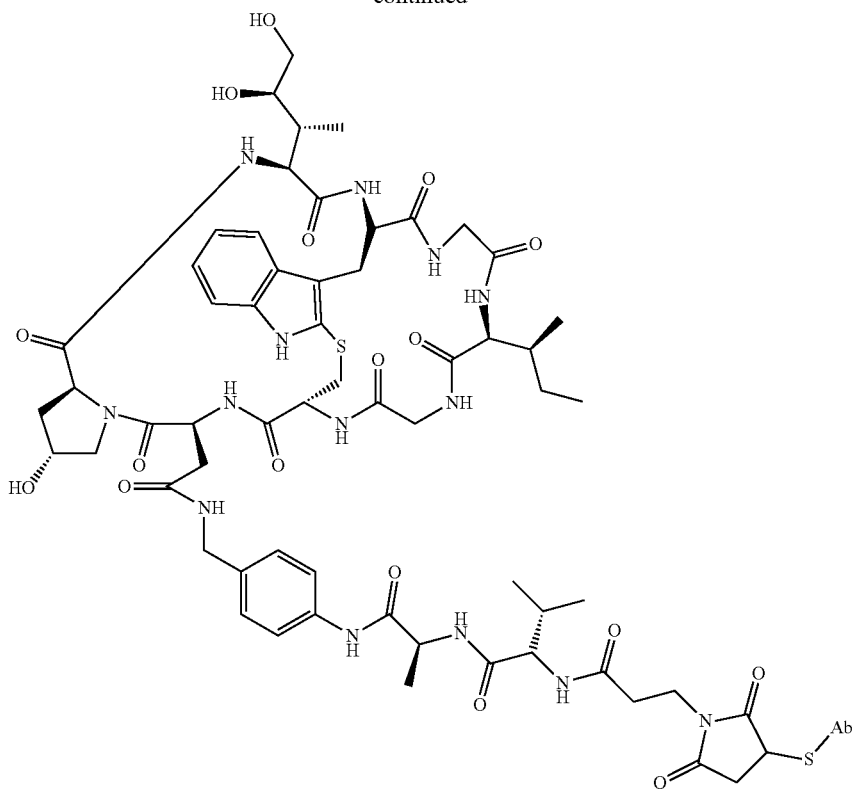
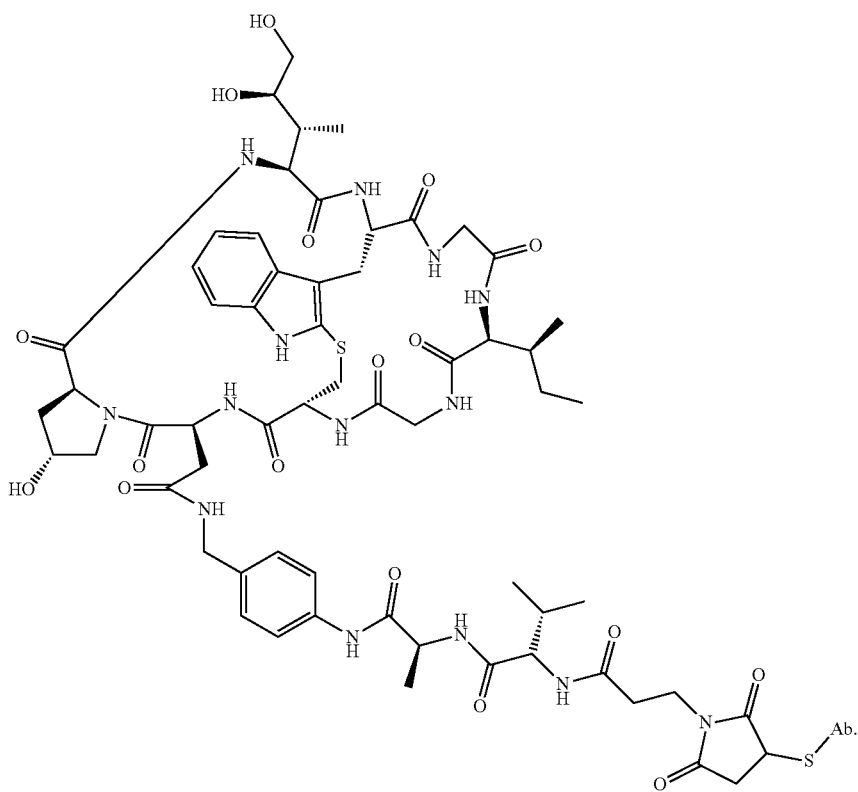

In one embodiment, the ADC is represented by one of the following structures:

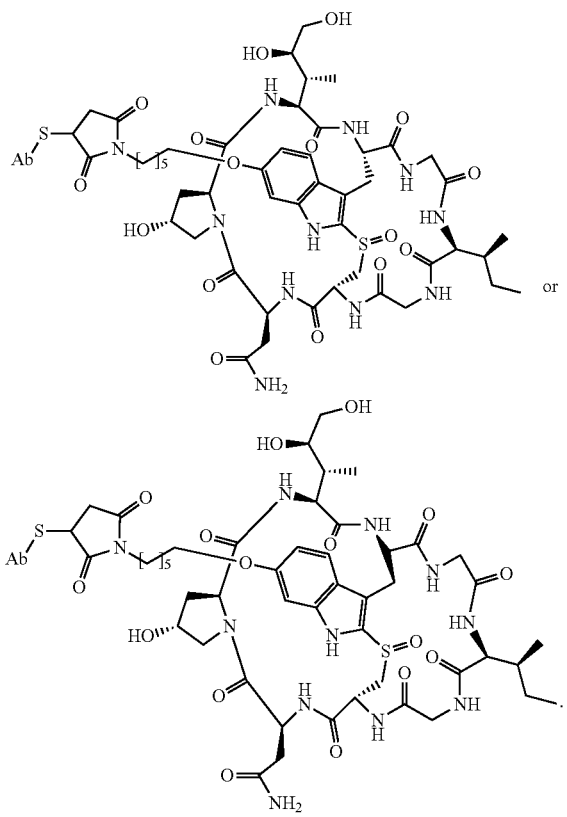

In one embodiment, the ADC has a serum half-life of 3 days or less.

In one embodiment, the extracellular domain of the CAR is an scFv antibody. In one embodiment, the extracellular domain of the CAR is a single chain T cell receptor (scTCR). In one embodiment, the extracellular domain of the CAR comprises a non-immunoglobulin scaffold protein.

In one embodiment, the extracellular domain of the CAR binds to a tumor antigen that is CD19, CD22, CD30, CD7, BCMA, CD137, CD22, CD20, AFP, GPC3, MUC1, mesothelin, CD38, PD1, EGFR (e.g., EGFRvIII), MG7, BCMA, TACI, CEA, PSCA, CEA, HER2, MUC1, CD33, ROR2, NKR-2, PSCA, CD28, TAA, NKG2D, or CD123.

In certain embodiments, the cytoplasmic domain of the CAR comprises a CD28 cytoplasmic signaling domain, a CD3 zeta cytoplasmic signaling domain, an OX40 cytoplasmic signaling domain, and/or a CD137 (4-1BB) cytoplasmic signaling domain. In one embodiment, the cytoplasmic domain of the CAR comprises a CD3 zeta cytoplasmic signaling domain.

The methods and compositions disclosed herein can be used to treat a human subject having cancer, including, but not limited to, leukemia, adult advanced cancer, pancreatic cancer, non-resectable pancreatic cancer, colorectal cancer, metastatic colorectal cancer, ovarian cancer, triple-negative breast cancer, hematopoietic/lymphoid cancer, colon cancer liver metastasis, small cell lung cancer, non-small cell lung cancer, B-cell lymphoma, relapsed or refractory B-cell lymphoma, follicular lymphoma, mantle cell lymphoma, diffuse large cell lymphoma, relapsed or refractory diffuse large cell lymphoma, anaplastic large cell lymphoma, primary mediastinal B-cell lymphoma, recurrent mediastinal, refractory mediastinal large B-cell lymphoma, large B-cell lymphoma, Hodgkin lymphoma, non-Hodgkin lymphoma, relapsed or refractory non-Hodgkin lymphoma, refractory aggressive non-Hodgkin lymphoma, B-cell non-Hodgkin lymphoma, refractory non-Hodgkin lymphoma, colorectal carcinoma, gastric carcinoma, pancreatic carcinoma, triple-negative invasive breast carcinoma, renal cell carcinoma, lung squamous cell carcinoma, hepatocellularcarcinoma, urothelial carcinoma, leukemia, B-cell leukemia, B-cell acute lymphocytic leukemia, B-cell acute lymphoblastic leukemia, adult acute lymphoblastic leukemia, B-cell prolymphocytic leukemia, childhood acute lymphoblastic leukemia, refractory childhood acute lymphoblastic leukemia, acute leukemia, acute lymphoblastic leukemia, acute lymphocytic leukemia, prolymphocytic leukemia, chronic lymphocytic leukemia, acute myeloid leukemia, recurrent plasma cell myeloma, refractory plasma cell myeloma, multiple myeloma, relapsed or refractory multiple myeloma, multiple myeloma of bone, malignant glioma of brain, myelodysplastic syndrome, EGFR-positive colorectal cancer, glioblastoma multiforme, neoplasms, blastic plasmacytoid dendritic cell neoplasms, liver metastases, solid tumors, advanced solid tumors, mesothelin positive tumors, hematological malignancies, and other advanced malignancies.

In certain embodiments of any of the above aspects, the anti-CD5 antibody, or antigen-binding fragment thereof contains a combination of CDRs (i.e., CDR-H1, CDR-H2, CDR-H3, CDR-L1, CDR-L2, and CDR-L3 regions) as set forth in Tables 1A and 1B, below. In certain embodiments, the anti-CD5 antibody, or antigen-binding fragment thereof contains a combination of a heavy chain variable region and a light chain variable region as set forth in Tables 1A and 1B.

BRIEF DESCRIPTION OF THE FIGURES

In FIG. 3A, the anti-CD5-ADC T-cell killing analysis is shown in comparison to an unconjugated anti-CD5 5D7 antibody (i.e., "CD5 5D7 NAKED"). In FIG. 3B, the anti-CD5-ADC T-cell killing analysis is shown in comparison to an anti-CD5 5D7 antibody having a H435A mutation (i.e., CD5 5D7 D265C.H435A AM) that decreases the half-life of the antibody (i.e., "CD5 Fast ½ Life AM"). The results show the number of viable T-cells (y-axis) as a function of ADC (CD5 5D7 AM, CD5 5D7

D265C.H435A AM) or unconjugated antibody (CD5 5D7 NAKED) concentration (x-axis), as assessed using flow cytometry.

Figure 4A:
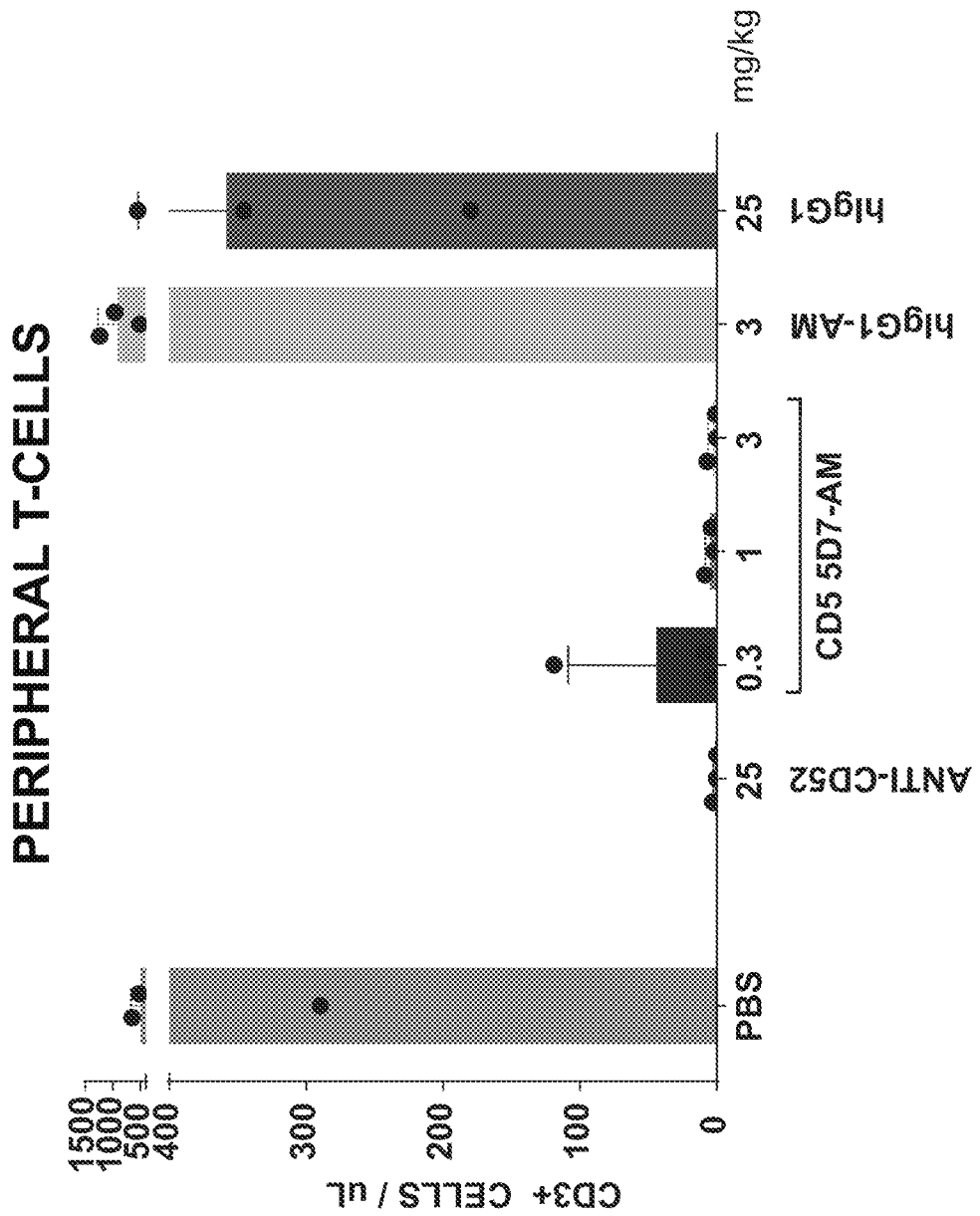
Figure 4B:
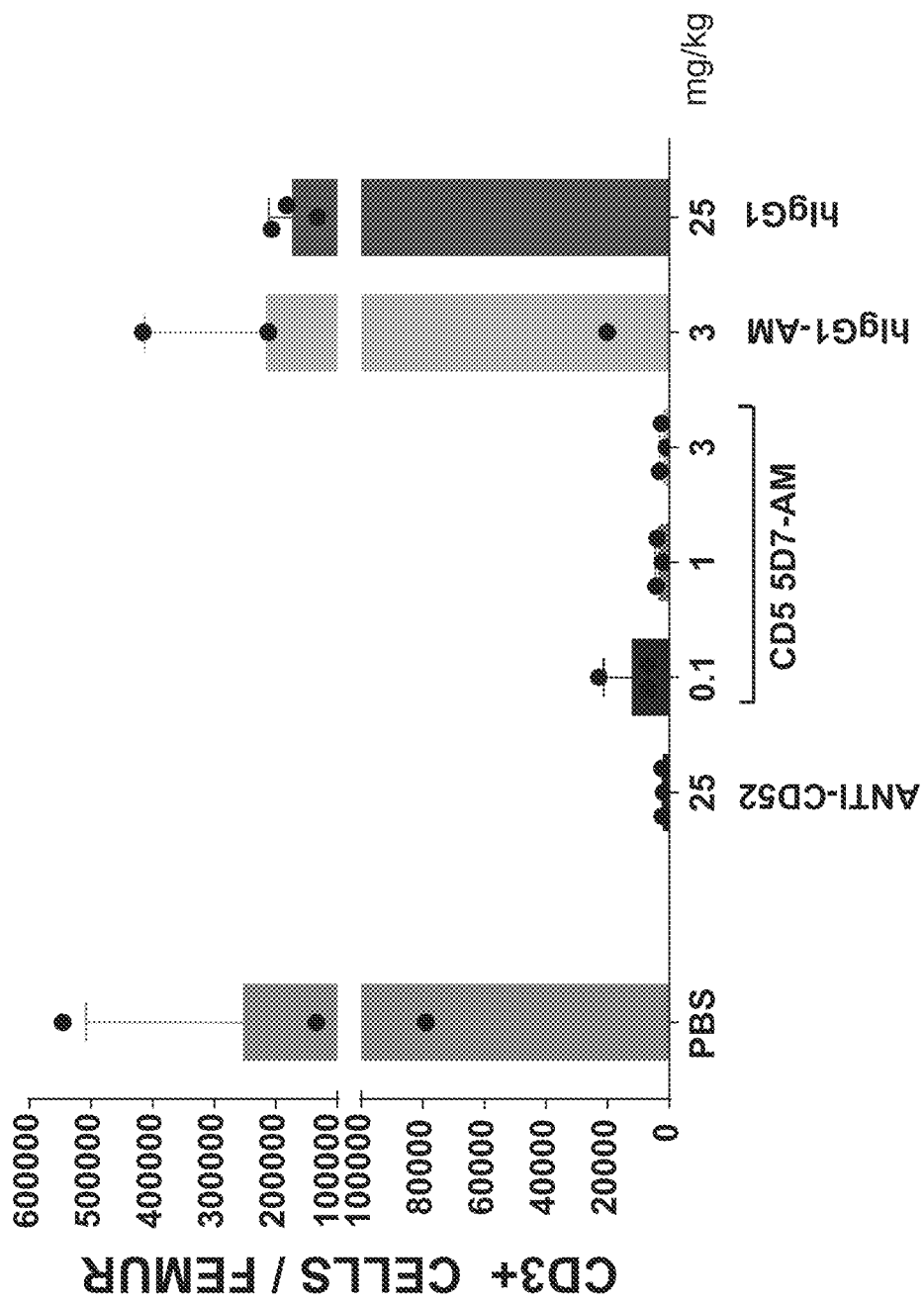

FIGS. 4A-4B graphically depict the results of an in vivo T-cell depletion assay showing the absolute levels of T-cells (CD3+ cells; y-axis) in the peripheral blood (FIG. 4A) and bone marrow (FIG. 4B) of humanized NSG mice 7 days after a single administration of 0.3 mg/kg, 1 mg/kg, or 3 mg/kg of an anti-CD5 5D7 amanitin ADC (i.e., CD5 5D7-AM) having an interchain DAR of 6. For comparison, FIGS. 4A-4B also show the level of T-cell depletion following treatment of humanized NSG mice with the indicated controls (i.e., 25 mg/kg anti-CD5 antibody; 3 mg/kg hIgG1-amanitin ADC (i.e., hIgG1-AM), 25 mg/kg hIgG1, or PBS).

Figure 5A:
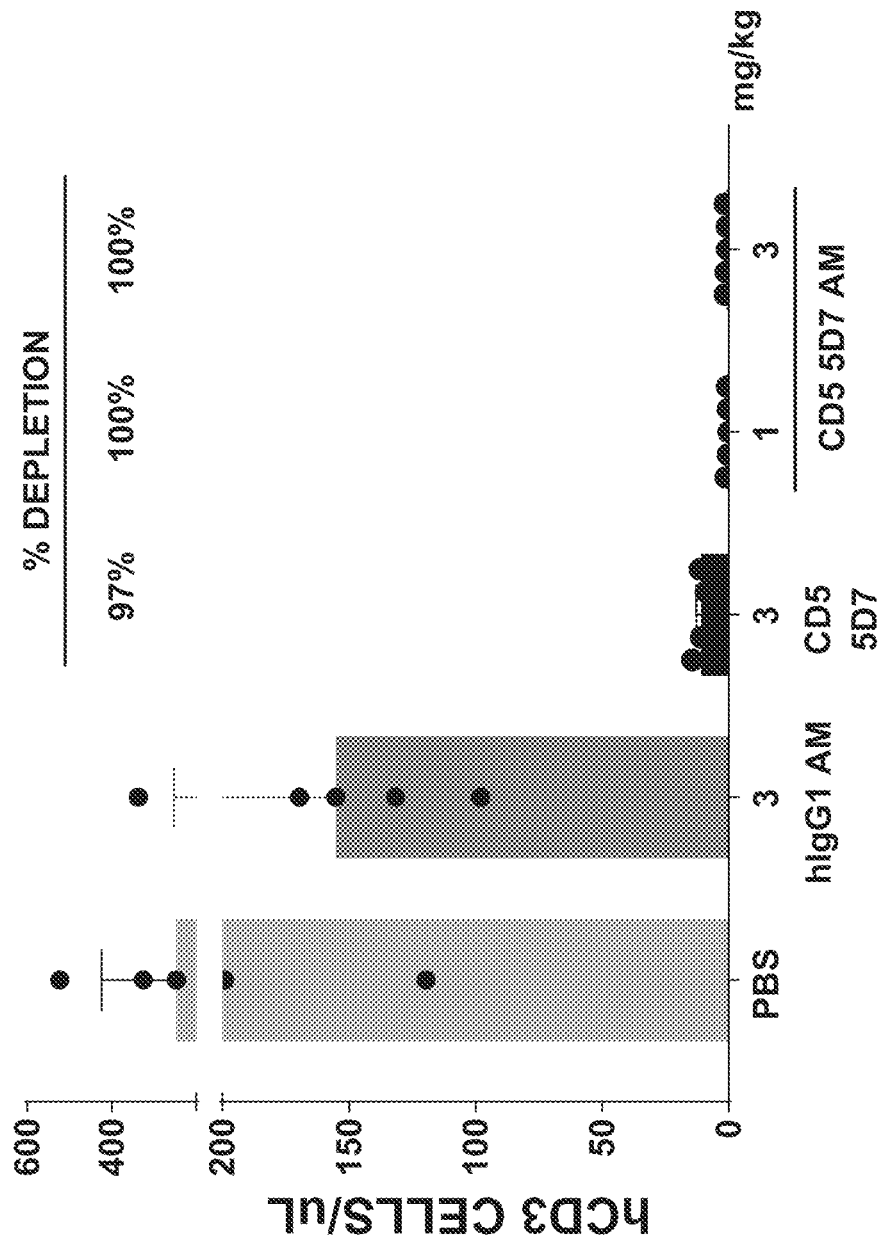
Figure 5B:
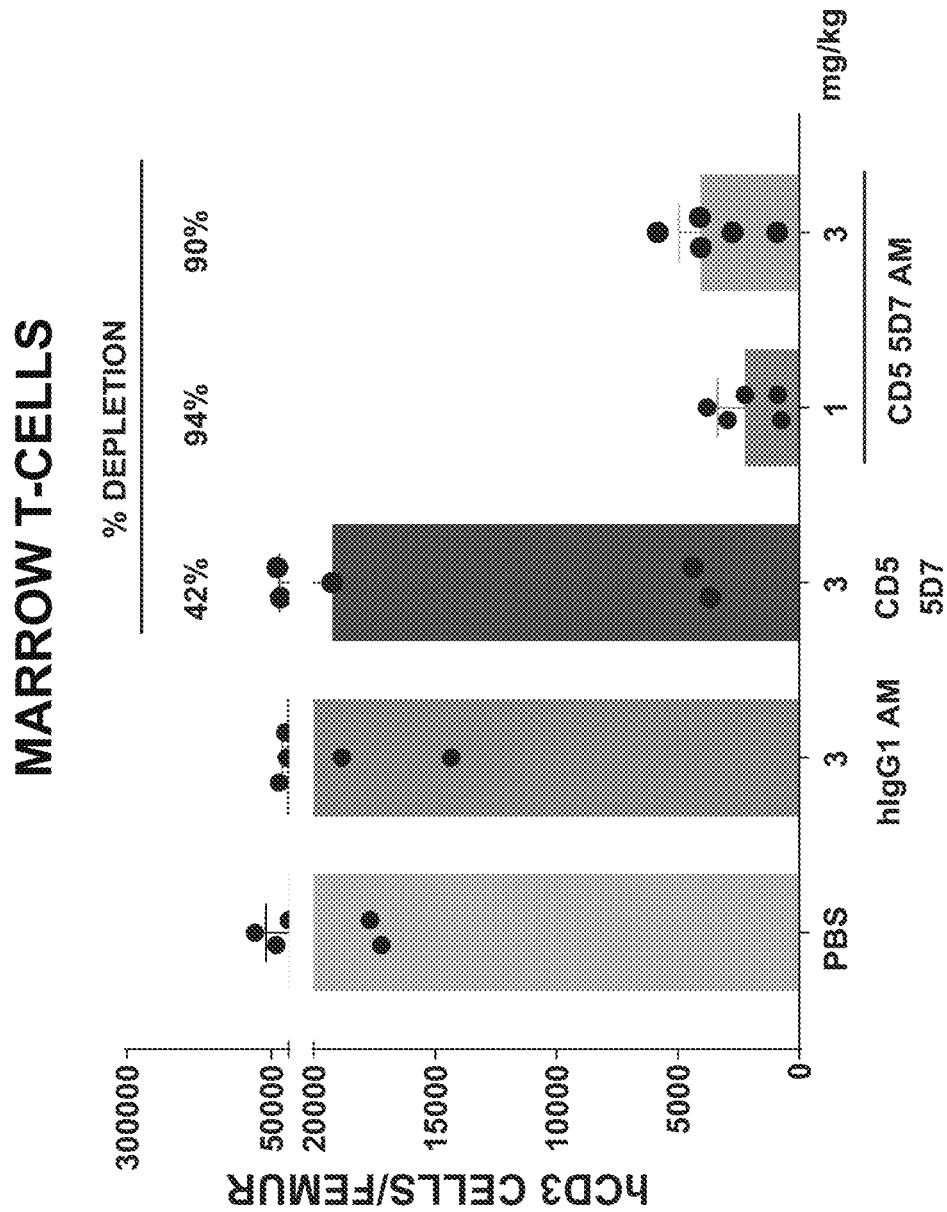
Figure 5C:
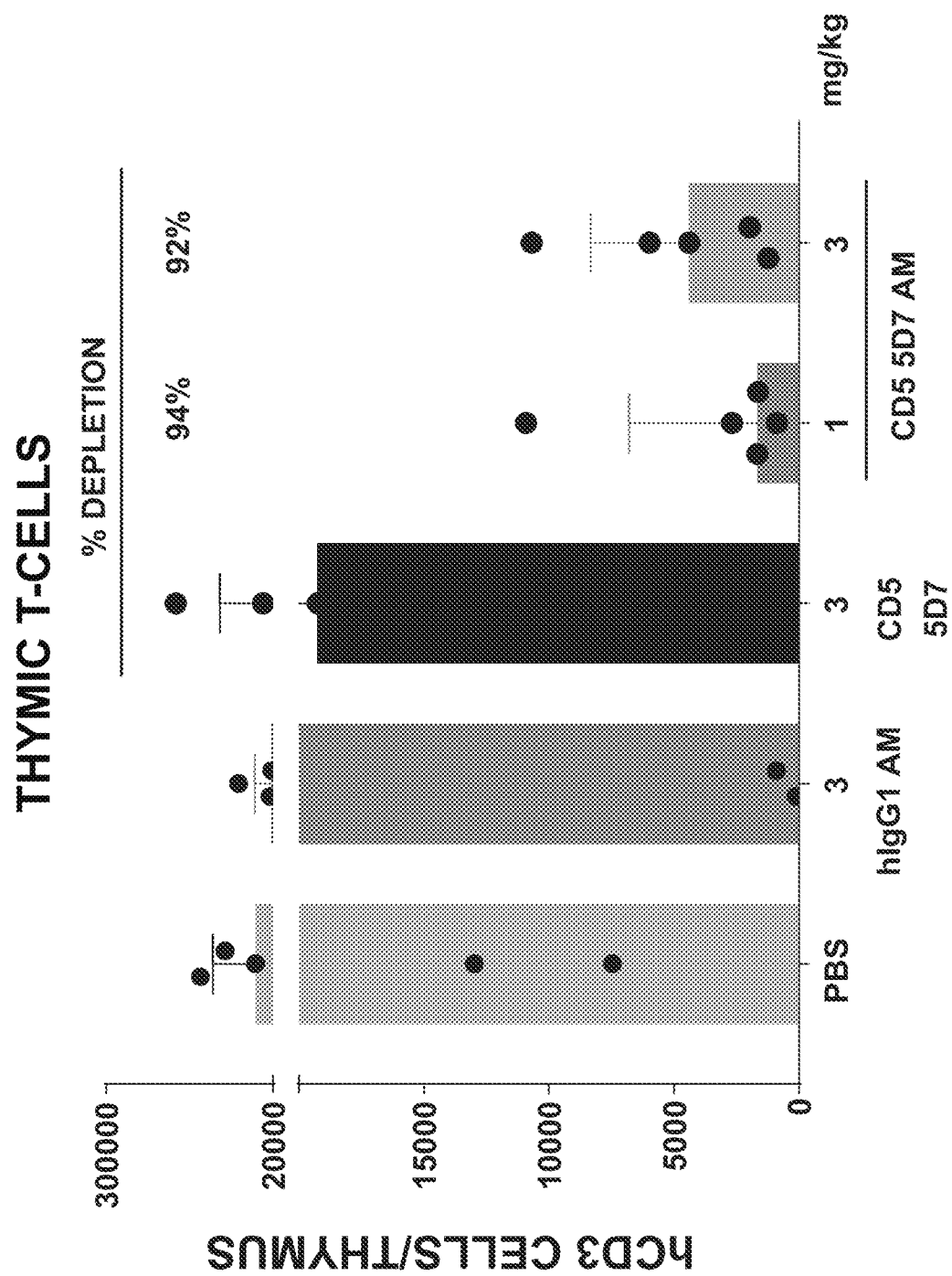

FIGS. 5A-5C graphically depict the results of an in vivo T-cell depletion assay showing the absolute levels of T-cells (CD3+ cells; y-axis) in the peripheral blood (FIG. 5A), bone marrow (FIG. 5B), and thymus (FIG. 5C) of humanized NSG mice 7 days after a single administration of 1 mg/kg or 3 mg/kg of an anti-CD5 5D7-amanitin ADC (i.e., CD5 5D7-AM) having a site-specific DAR of 2. For comparison, FIGS. 5A-5C also show the level of T-cell depletion following treatment of humanized NSG mice with 3 mg/kg of an unconjugated anti-CD5 antibody (i.e., CD5 5D7) or with the indicated controls (i.e., 3 mg/kg hIgG1-amanitin-ADC ("hIgG1-AM") or PBS).

DETAILED DESCRIPTION

The present invention provides methods for promoting acceptance of an immune cell (either autologous or allogeneic) expressing a chimeric antigen receptor (CAR) in a human subject receiving CAR therapy by administering an anti-CD5 antibody drug conjugate (ADC) to the patient receiving the CAR therapy. The methods disclosed herein can be used to improve acceptance of autologous or allogeneic immune cells (e.g., T cells) without reliance on (or alternatively a reduced use of) lymphodepleting chemotherapy commonly used as a conditioning therapy to reduce rejection of the CAR expressing immune cells.

I. Definitions

As used herein, the term "about" refers to a value that is within 5% above or below the value being described.

As used herein, the term "allogeneic", when used in the context of transplantation, is used to define cells (or tissue or an organ) that are transplanted from a donor to a recipient of the same species, where the donor and the recipient are not the same subject.

As used herein, the term "autologous" refers to cells or a graft where the donor and recipient are the same subject.

As used herein, the term "xenogeneic" refers to cells where the donor and recipient species are different.

As used herein, the term "immune cell" is intended to include, but is not limited to, a cell that is of hematopoietic origin and that plays a role in the immune response. Immune cells include, but are not limited to, T cells and natural killer (NK) cells. Natural killer cells are well known in the art. In one embodiment, natural killer cells include cell lines, such as NK-92 cells. Further examples of NK cell lines include NKG, YT, NK-YS, HANK-1, YTS cells, and NKL cells. An immune cell can be allogeneic or autologous.

An "engineered cell" means any cell of any organism that is modified, transformed, or manipulated by addition or modification of a gene, a DNA or RNA sequence, or protein or polypeptide. Isolated cells, host cells, and genetically engineered cells of the present disclosure include isolated immune cells, such as NK cells and T cells that contain the DNA or RNA sequences encoding a CAR and express the CAR on the cell surface. Isolated host cells and engineered cells may be used, for example, for enhancing an NK cell activity or a T lymphocyte activity, treatment of cancer, and treatment of autoimmune diseases. In an embodiment, the engineered cell includes immune cells, e.g., T-cells or Natural Killer (NK cells).

As used herein, the term "antibody" refers to an immunoglobulin molecule that specifically binds to, or is immunologically reactive with, a particular antigen. An antibody includes, but is not limited to, monoclonal antibodies, polyclonal antibodies, multispecific antibodies (e.g., bispecific antibodies), and antibody fragments so long as they exhibit the desired antigen-binding activity.

Generally, antibodies comprise heavy and light chains containing antigen binding regions. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH, and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding fragment," as used herein, refers to one or more portions of an antibody that retain the ability to specifically bind to a target antigen. The antigen-binding function of an antibody can be performed by fragments of a full-length antibody. The antibody fragments can be, for example, a Fab, F(ab')2, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the VL, VH, CL, and CH1 domains; (ii) a F(ab')2 fragment, a bivalent fragment containing two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb including VH and VL domains; (vi) a dAb fragment that consists of a VH domain (see, e.g., Ward et al., Nature 341:544-546, 1989); (vii) a dAb which consists of a VH or a VL domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, VL and VH, are coded for by separate genes, they can be joined, using recombinant methods, by a linker that enables them to be made as a single protein chain in which the VL and VH regions pair to form monovalent molecules (known as single chain Fv (scFv); see, for example, Bird et al., Science 242:423-426, 1988 and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

An "intact" or "full length" antibody, as used herein, refers to an antibody having two heavy (H) chain polypeptides and two light (L) chain polypeptides interconnected by disulfide bonds.

As used herein, the term "anti-CD5 antibody" or "an antibody that binds to CD5" or an "anti-CD5 ADC" or "an ADC that binds to CD5" refers to an antibody or ADC that specifically binds to human CD5 as CD5 is found on the cell surface of cells, such as T cells. The amino acid sequence of human CD5 to which an anti-CD5 antibody (or anti-CD5 ADC) would bind is described below in SEQ ID NO: 20.

The term "specifically binds", as used herein, refers to the ability of an antibody (or ADC) to recognize and bind to a specific protein structure (epitope) rather than to proteins generally. If an antibody is specific for epitope "A", the presence of a molecule containing epitope A (or free, unlabeled A), in a reaction containing labeled "A" and the antibody, will reduce the amount of labeled A bound to the antibody. By way of example, an antibody "binds specifically" to a target if the antibody, when labeled, can be competed away from its target by the corresponding non-labeled antibody. In one embodiment, an antibody specifically binds to a target, e.g., CD5, if the antibody has a $K_D$ for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or less (less meaning a number that is less than $10^{-12}$, e.g. $10^{-13}$). In one embodiment, the term "specific binding to CD5" or "specifically binds to CD5," as used herein, refers to an antibody or that binds to CD5 and has a dissociation constant ($K_D$) of $1.0 \times 10^{-7}$ M or less, as determined by surface plasmon resonance. In one embodiment, $K_D$ is determined according to standard bio-layer interferometery (BLI). It shall be understood, however, that the antibody may be capable of specifically binding to two or more antigens which are related in sequence. For example, in one embodiment, an antibody can specifically bind to both human and a non-human (e.g., mouse or non-human primate) orthologs of CD5.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397.

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332.

As used herein, the terms "chimeric antigen receptor" or "CAR" refer to a recombinant polypeptide comprising at least an extracellular domain capable of specifically binding an antigen, a transmembrane domain, and at least one intracellular signaling domain. Generally a CAR is a genetically engineered receptor that redirects cytotoxicity of immune effector cells toward cells presenting the given antigen. CARs are molecules that combine antibody-based specificity for a desired antigen (e.g., a tumor antigen) with a T cell receptor-activating intracellular domain to generate a chimeric protein that exhibits a specific cellular immune activity. In particular embodiments, CARs comprise an extracellular domain (also referred to as a binding domain or antigen-specific binding domain), a transmembrane domain, and an intracellular (cytoplasmic) signaling domain. Engagement of the antigen binding domain of the CAR with the target antigen on the surface of a target cell results in clustering of the CAR and delivers an activation stimulus to the CAR-containing cell. A main characteristic of a CAR is its ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors. In some embodiments, a CAR comprises an extracellular binding domain that specifically binds to a tumor antigen; a transmembrane domain; and one or more intracellular signaling domains. In various embodiments, a CAR comprises an extracellular binding domain that specifically binds human CD5; a transmembrane domain; and one or more intracellular signaling domains.

As used herein, the term "CAR therapy" refers to administration of an immune cell that has been engineered to express a CAR, to a human subject for the treatment of a given disease, e.g., cancer or an autoimmune disease. CAR therapy refers to the specific treatment of the patient with the engineered immune cells and is not intended to include therapies that commonly are used in conjunction with CAR cell treatment, e.g., lymphodepleting chemotherapy. Notably, where the term "cell" is used throughout, populations of cells are also included by the term unless otherwise specified. For example, as CAR therapy requires administration of a population of engineered cells.

As used herein, the term "combination" or "combination therapy" refers to the use of two (or more) therapies in a single human patient. The terms are not intended to refer to a combination composition. For example, described herein is a combination therapy comprising administering an anti-CD5 ADC and CAR therapy.

The term "conditioning" refers to the preparation of a patient in need of CAR therapy for a suitable condition. Conditioning as used herein includes, but is not limited to, reducing the number of endogenous lymphocytes, removing a cytokine sink, increasing a serum level of one or more homeostatic cytokines or pro-inflammatory factors, enhancing an effector function of T cells administered after the conditioning, enhancing antigen presenting cell activation and/or availability, or any combination thereof prior to a T cell therapy.

The term "deplete," in the context of the effect of an anti-CD5 antibody or ADC on CD5-expressing cells, refers to a reduction in the number of or elimination of CD5-expressing cells.

As used herein, the term "effective amount" or "therapeutically effective amount" refers to an amount that is sufficient to achieve the desired result or to have an effect on an autoimmune disease or cancer.

As used herein, the terms "subject" and "patient" refer to an organism, such as a human, that receives treatment for a particular disease or condition as described herein.

As used herein "to treat" or "treatment", refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act. Beneficial or desired clinical results include, but are not limited to, promoting acceptance of CAR expressing immune cells (allogeneic or autologous—both of which can cause immune reactions in a patient receiving CAR therapy). Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state is completely avoided.

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of CARs or include plasmids that contain regulatory sequences, such as promoter and enhancer regions, which direct gene transcription. Other useful vectors for antibody or CAR expression contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

As used herein, the term "antibody drug conjugate" or "ADC" refers to an antibody which is linked to a cytotoxin. An ADC is formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules bound to one another, e.g., between an antibody and a cytotoxin. Notably, the term "conjugate" (when referring to a compound) is also referred to interchangeably herein as a "drug conjugate", "antibody drug conjugate" or "ADC". Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012).

As used herein, the term "coupling reaction" refers to a chemical reaction in which two or more substituents suitable for reaction with one another react so as to form a chemical moiety that joins (e.g., covalently) the molecular fragments bound to each substituent. Coupling reactions include those in which a reactive substituent bound to a fragment that is a cytotoxin, such as a cytotoxin known in the art or described herein, reacts with a suitably reactive substituent bound to a fragment that is an antibody, or antigen-binding fragment thereof, such as an antibody, antigen-binding fragment thereof, or specific anti-CD5 antibody that binds CD5 known in the art or described herein. Examples of suitably reactive substituents include a nucleophile/electrophile pair (e.g., a thiol/haloalkyl pair, an amine/carbonyl pair, or a thiol/α,β-unsaturated carbonyl pair, among others), a diene/dienophile pair (e.g., an azide/alkyne pair, among others), and the like. Coupling reactions include, without limitation, thiol alkylation, hydroxyl alkylation, amine alkylation, amine condensation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein.

As used herein, the term "microtubule-binding agent" refers to a compound which acts by disrupting the microtubular network that is essential for mitotic and interphase cellular function in a cell. Examples of microtubule-binding agents include, but are not limited to, maytasine, maytansinoids, and derivatives thereof, such as those described herein or known in the art, vinca alkaloids, such as vinblastine, vinblastine sulfate, vincristine, vincristine sulfate, vindesine, and vinorelbine, taxanes, such as docetaxel and paclitaxel, macrolides, such as discodermolides, cochicine, and epothilones, and derivatives thereof, such as epothilone B or a derivative thereof.

As used herein, the term "amatoxin" refers to a member of the amatoxin family of peptides produced by *Amanita phalloides* mushrooms, or derivative thereof, such as a variant or derivative thereof capable of inhibiting RNA polymerase II activity. Amatoxins useful in conjunction with the compositions and methods described herein include compounds such, as but not limited to, compounds of Formula (II), e.g., α-amanitin, β-amanitin, γ-amanitin, ε-amanitin, amanin, amaninamide, amanullin, amanullinic acid, or proamanullin. Amatoxins may be isolated from a variety of mushroom species (e.g., *Amanita phalloides, Galerina marginata, Lepiota brunneo-incarnata*) or may be prepared semi-synthetically or synthetically. A member of this family, α-amanitin, is described in Wieland, *Int. J. Pept. Protein Res.* 1983, 22(3):257-276. A derivative of an amatoxin may be obtained by chemical modification of a naturally occurring compound ("semi-synthetic"), or may be obtained from an entirely synthetic source. Synthetic routes to various amatoxin derivatives are disclosed in, for example, U.S. Pat. No. 9,676,702 and in Perrin et al., J. Am. Chem. Soc. 2018, 140, p. 6513-6517, each of which is incorporated by reference herein in their entirety with respect to synthetic methods for preparing and derivatizing amatoxins.

As described herein, amatoxins may be conjugated to an antibody, or antigen-binding fragment thereof, for instance, by way of a linker moiety (L) (thus forming an ADC). The structures of exemplary amatoxin-linker conjugates are represented by Formulas (III), (IIIA), and (IIIB). Exemplary methods of amatoxin conjugation and linkers useful for such processes are described below. Exemplary linker-containing amatoxins useful for conjugation to an antibody, or antigen-binding fragment, in accordance with the compositions and methods are also described herein.

The term "acyl" as used herein refers to —C(=O)R, wherein R is hydrogen ("aldehyde"), $C_1$-$C_{12}$ alkyl, $C_2$-$C_{12}$ alkenyl, $C_2$-$C_{12}$ alkynyl, $C_3$-$C_7$ carbocyclyl, $C_6$-$C_{20}$ aryl, 5-10 membered heteroaryl, or 5-10 membered heterocyclyl, as defined herein. Non-limiting examples include formyl, acetyl, propanoyl, benzoyl, and acryloyl.

The term "$C_1$-$C_{12}$ alkyl" as used herein refers to a straight chain or branched, saturated hydrocarbon having from 1 to 12 carbon atoms. Representative $C_1$-$C_{12}$ alkyl groups include, but are not limited to, -methyl, -ethyl, -n-propyl, -n-butyl, -n-pentyl, and -n-hexyl; while branched $C_1$-$C_{12}$ alkyls include, but are not limited to, -isopropyl, -sec-butyl, -isobutyl, -tert-butyl, -isopentyl, and 2-methylbutyl. A $C_1$-$C_{12}$ alkyl group can be unsubstituted or substituted.

The term "alkenyl" as used herein refers to $C_2$-$C_{12}$ hydrocarbon containing normal, secondary, or tertiary carbon atoms with at least one site of unsaturation, i.e., a carbon-carbon, $sp^2$ double bond. Examples include, but are not limited to: ethylene or vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, and the like. An alkenyl group can be unsubstituted or substituted.

"Alkynyl" as used herein refers to a $C_2$-$C_{12}$ hydrocarbon containing normal, secondary, or tertiary carbon atoms with at least one site of unsaturation, i.e., a carbon-carbon, sp triple bond. Examples include, but are not limited to acetylenic and propargyl. An alkynyl group can be unsubstituted or substituted.

"Aryl" as used herein refers to a $C_6$-$C_{20}$ carbocyclic aromatic group. Examples of aryl groups include, but are not limited to, phenyl, naphthyl and anthracenyl. An aryl group can be unsubstituted or substituted.

"Arylalkyl" as used herein refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms. An alkaryl group can be unsubstituted or substituted.

"Cycloalkyl" as used herein refers to a saturated carbocyclic radical, which may be mono- or bicyclic. Cycloalkyl groups include a ring having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted.

"Cycloalkenyl" as used herein refers to an unsaturated carbocyclic radical, which may be mono- or bicyclic. Cycloalkenyl groups include a ring having 3 to 6 carbon atoms as a monocycle or 7 to 12 carbon atoms as a bicycle. Examples of monocyclic cycloalkenyl groups include 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl. A cycloalkenyl group can be unsubstituted or substituted.

"Heteroaralkyl" as used herein refers to an acyclic alkyl radical in which one of the hydrogen atoms bonded to a carbon atom, typically a terminal or sp3 carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo[4,5], [5,5], [5,6], or [6,6] system.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl radical comprises 2 to 20 carbon atoms and 1 to 3 heteroatoms selected from N, O, P, and S. A heteroaryl or heterocycloalkyl may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system. Heteroaryl and heterocycloalkyl can be unsubstituted or substituted.

Heteroaryl and heterocycloalkyl groups are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heteroaryl groups include by way of example and not limitation pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl.

Examples of heterocycloalkyls include by way of example and not limitation dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl.

By way of example and not limitation, carbon bonded heteroaryls and heterocycloalkyls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heteroaryls and heterocycloalkyls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or beta-carboline. Still more typically, nitrogen bonded heterocycles include 1-aziridyl, 1-azetedyl, 1-pyrrolyl, 1-imidazolyl, 1-pyrazolyl, and 1-piperidinyl.

"Substituted" as used herein and as applied to any of the above alkyl, alkenyl, alkynyl, aryl, arylalkyl, cycloalkyl, heteroaryl, heterocyclyl, and the like, means that one or more hydrogen atoms are each independently replaced with a substituent. Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", heterocycloalkylene", "aryl," "arylene", "heteroaryl", and "heteroarylene" groups can optionally be substituted.

Typical substituents include, but are not limited to, —X, —R, —OH, —OR, —SH, —SR, $NH_2$, —NHR, —N(R)$_2$, —N$^+$(R)$_3$, —CX$_3$, —CN, —OCN, —SCN, —NCO, —NCS, —NO, —NO$_2$, —N$_3$, —NC(=O)H, —NC(=O)R, —C(=O)H, —C(=O)R, —C(=O)NH$_2$, —C(=O)N(R)$_2$, —SO$_3$—, —SO$_3$H, —S(=O)$_2$R, —OS(=O)$_2$OR, —S(=O)$_2$NH$_2$, —S(=O)$_2$N(R)$_2$, —S(=O)R, —OP(=O)(OH)$_2$, —OP(=O)(OR)$_2$, —P(=O)(OR)$_2$, —PO$_3$, —PO$_3$H$_2$, —C(=O)X, —C(=S)R, —CO$_2$H, —CO$_2$R, —CO$_2$—, —C(=S)OR, —C(=O)SR, —C(=S)SR, —C(=O)NH$_2$, —C(=O)N(R)$_2$, —C(=S)NH$_2$, —C(=S)N(R)$_2$, —C(=NH)NH$_2$, and —C(=NR)N(R)$_2$; wherein each X is independently selected for each occasion from F, Cl, Br, and I; and each R is independently selected for each occasion from $C_1$-$C_{12}$ alkyl, $C_6$-$C_{20}$ aryl, $C_3$-$C_{14}$ heterocyoalkyl or heteroaryl, protecting group and prodrug moiety. Wherever a group is described as "optionally substituted," that group can be substituted with one or more of the above substituents, independently for each occasion.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene," "alkenylene," "arylene," "heterocycloalkylene," and the like.

Wherever a substituent is depicted as a di-radical (i.e., has two points of attachment to the rest of the molecule), it is to be understood that the substituent can be attached in any directional configuration unless otherwise indicated.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers," or sometimes "optical isomers."

A carbon atom bonded to four non-identical substituents is termed a "chiral center." "Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J. Chem. Educ. 1964, 41, 116). A mixture containing equal amounts of individual enantiomeric forms of opposite chirality is termed a "racemic mixture."

The compounds disclosed in this description and in the claims may comprise one or more asymmetric centers, and different diastereomers and/or enantiomers of each of the compounds may exist. The description of any compound in this description and in the claims is meant to include all enantiomers, diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer. Accordingly, enantiomers, optical isomers, and diastereomers of each of the structural formulae of the present disclosure are contemplated herein. In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. The compounds may occur in different tautomeric forms. The compounds according to the disclosure are meant to include all tautomeric forms, unless stated otherwise. When the structure of a compound is depicted as a specific tautomer, it is to be understood that the invention of the present application is not limited to that specific tautomer.

The compounds of any formula described herein include the compounds themselves, as well as their salts, and their solvates, if applicable. A salt, for example, can be formed between an anion and a positively charged group (e.g., amino) on a compound of the disclosure. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a compound of the disclosure. Suitable cations include sodium ion, potassium ion, magnesium ion, calcium ion, and an ammonium cation such as tetramethylammonium ion. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. The compounds of the disclosure also include those salts containing quaternary nitrogen atoms.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Additionally, the compounds of the present disclosure, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc. "Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hydrate refers to, for example, a mono-hydrate, a di-hydrate, a tri-hydrate, etc.

In addition, a crystal polymorphism may be present for the compounds or salts thereof represented by the formulae disclosed herein. It is noted that any crystal form, crystal form mixture, or anhydride or hydrate thereof, is included in the scope of the present disclosure.

The sections that follow provide a description of methods based on the administration of an anti-CD5 ADCs to a human patient to promote acceptance of an immune cell expressing a CAR in CAR therapy.

II. Anti-CD5 ADC and CAR Methods of Treatment

A challenge of chimeric antigen receptor (CAR) therapy is determining a means by which the engineered CAR expressing cells, e.g., CAR-T cells, can be accepted by a human recipient. Such acceptance of the engineered immune cells can impact the efficacy of the treatment and also results in adverse side effects to the patient.

Lymphodepleting chemotherapy is a traditional way of suppressing the recipient's immune system to improve acceptance, but commonly has adverse side effects. Described herein are methods of promoting acceptance of (CAR) expressing immune cells in human patients who are receiving CAR therapy. The methods described herein specifically target CD5+ cells, e.g., CD5+ T cells, in the human patient who is undergoing CAR therapy and ablates the CD5+ cells. The methods disclosed herein are more targeted than lymphodepleting chemotherapy and provide a means by which either autologous or allogeneic cells can be used.

Described herein are methods of administering anti-CD5 antibody-drug conjugates (ADCs) to deplete a population of CD5 specific immune cells within the patient receiving CAR therapy in order to facilitate the acceptance and efficacy of CAR-expressing immune cells. This selective depletion of specific CD5 expressing cells of the immune system improves overall and relapse-free patient survival while decreasing the risk of rejection of the CAR-expressing immune cell for treating autoimmune disorders or cancer.

The risk of rejection of a CAR expressing immune cell remains high following the administration of CAR cell therapies. The methods and compositions disclosed herein may be used to inhibit or prevent the rejection of a CAR cell in a human patient. The anti-CD5 ADCs may be used to selectively target activated T cells in a patient who will be receiving a CAR cell therapy. Anti-CD5 ADCs, as described herein, may also be used to reduce the risk of the rejection of a CAR cell by targeting and depleting CD5 positive cells in a human patient who has already received a CAR cell therapy.

The compositions and methods described herein may be used to deplete CD5+ cells, e.g., T cells, that are associated with CAR cell therapy rejection. The methods of the invention promote acceptance of an immune cell expressing a CAR in a human subject, e.g., a human subject having cancer or an autoimmune disease. In one embodiment, the method includes administering an anti-CD5 antibody drug conjugate (ADC) to a human subject who will be undergoing or has undergone CAR therapy, and administering a therapeutically effective amount of an immune cell expressing a CAR to the human subject.

The anti-CD5 ADC can be administered to the human patient in need thereof prior to, concomitantly with, or following administration of one or more CAR cell therapies. In one embodiment, an anti-CD5 ADC is administered to the human patient in need thereof prior to (e.g., about 3 days before, about 2 days before, about 12 hours before) administration of CAR cell therapies. A single dose of an anti-CD5 ADC may be administered to the human patient either prior to, after, or concomitantly with, administration of CAR cell therapies, where such single dose is sufficient to prevent or reduce the risk of depletion of the CAR expressing immune cell. In one embodiment, an anti-CD5 ADC is administered to the human patient in need thereof about 3 days prior to administration of CAR cell therapies. In one embodiment, an anti-CD5 ADC is administered to the human patient in need thereof about 2 days prior to administration of CAR cell therapies. In one embodiment, an anti-CD5 ADC is administered to the human patient in need thereof about 1 day prior to administration of CAR cell therapies. In one embodiment, an anti-CD5 ADC is administered to the human patient in need thereof about 20 hours prior to administration of CAR cell therapies. In one embodiment, an anti-CD5 ADC is administered to the human patient in need thereof about 18 hours prior to administration of CAR cell therapies. In one embodiment, an anti-CD5 ADC is administered to the human patient in need thereof 15 hours prior to administration of CAR cell therapies. In one embodiment, an anti-CD5 ADC is administered to the human patient in need thereof about 12 hours prior to administration of CAR cell therapies. In one embodiment, an anti-CD5 ADC is administered to the human patient in need thereof about 6 hours prior to administration of CAR cell therapies. In one embodiment, an anti-CD5 ADC is administered to the human patient in need thereof about 4 hours prior to administration of CAR cell therapies. In one embodiment, an anti-CD5 ADC is administered to the human patient in need thereof about 2 hours prior to administration of CAR cell therapies. In one embodiment, an anti-CD5 ADC is administered to the human patient in need thereof concomitantly with the administration of CAR cell therapies. In one embodiment, an anti-CD5 ADC is administered to the human patient in need thereof about 2 hours after administration of CAR cell therapies. In one embodiment, an anti-CD5 ADC is administered to the human patient in need thereof about 4 hours after administration of CAR cell therapies. In one embodiment, an anti-CD5 ADC is administered to the human patient in need thereof about 6 hours after administration of CAR cell therapies. In one embodiment, an anti-CD5 ADC is administered to the human patient in need thereof about 12 hours after administration of CAR cell therapies.

In some embodiments, the anti-CD5 ADC can be administered up to about 21 days prior to the administration of one or more CAR cell therapies, e.g., about 21 days, about 20 days, about 19 days, about 18 days, about 17 days, about 16 days, about 15 days, about 14 days, about 13 days, about 12 days, about 11 days, about 10 days, about 9 days, about 8 days, about 7 days, about 6 days, about 5 days, about 4 days, about 3 days, about 2 days, about 1 day, about 24 hours, about 12 hours, about 6 hours, about 3 hours, about 2 hours, or about 1 hour prior to the administration of one or more CAR cell therapies.

In some embodiments, the anti-CD5 ADC can be administered about 12 hours after administration of CAR cell therapies, e.g., about 12 hours, about 11 hours, about 10 hours, about 9 hours, about 8 hours, about 7 hours, about 6 hours, about 5 hours, about 4 hours, about 3 hours, about 2 hours, about 1 hour after the administration of one or more CAR cell therapies. In some embodiments, the anti-CD5 ADC can be administered about 10 days after administration of CAR cell therapies, e.g., about 10 days, about 9 days, about 8 days, about 7 days, about 6 days, about 5 days, about 4 days, about 3 days, about 2 days, about 1 day after the administration of one or more CAR cell therapies.

In one embodiment, the anti-CD5 ADC is administered before the CAR expressing immune cells are administered to the human patient in need thereof. In one embodiment, the anti-CD5 ADC is administered to the human patient in combination with CAR therapy, where the anti-CD5 ADC is administered to the human subject about 12 hours to about 21 days before administration of the CAR expressing immune cells. In one embodiment, the anti-CD5 ADC is administered to the human patient in combination with CAR therapy, where the anti-CD5 ADC is administered to the human subject about 18 hours to about 20 days before administration of the CAR expressing immune cells. In one embodiment, the anti-CD5 ADC is administered to the human patient in combination with CAR therapy, where the anti-CD5 ADC is administered to the human subject about 20 hours to about 18 days before administration of the CAR expressing immune cells. In one embodiment, the anti-CD5 ADC is administered to the human patient in combination with CAR therapy, where the anti-CD5 ADC is administered to the human subject about 1 day to about 15 days before administration of the CAR expressing immune cells. In one embodiment, the anti-CD5 ADC is administered to the human patient in combination with CAR therapy, where the anti-CD5 ADC is administered to the human subject about 1 day to about 10 days before administration of the CAR expressing immune cells. In one embodiment, the anti-CD5 ADC is administered to the human patient in combination with CAR therapy, where the anti-CD5 ADC is administered to the human subject about 2 days to about 8 days before administration of the CAR expressing immune cells. In one embodiment, the anti-CD5 ADC is administered to the human patient in combination with CAR therapy, where the anti-CD5 ADC is administered to the human subject about 3 days to about 6 days before administration of the CAR expressing immune cells.

Overall levels of T cells in a biological sample from a human patient can be tested following administration of an anti-CD5 ADC, wherein a decrease in the overall number of T cells in a human patient following administration of the anti-CD5 ADC relative to the level prior to administration indicates efficacy of the anti-CD5 ADC for preventing rejection of the CAR cell therapy. In one embodiment, the level of endogenous T cells in a biological sample from the human patient is reduced by at least about 5%, at least about 10%, at least about 15%, at least about 20%, relative to the level of T cells in a biological sample (of the same type, e.g., blood) from the human patient just prior to administration of the anti-CD5 ADC. In one embodiment, the level of endogenous T cells in a biological sample from the human patient is reduced by about 5% to 25%, by about 5% to 20%, by about 5% to 15%, or by about 5% to 10%, relative to the level of T cells in a biological sample (of the same type, e.g., blood) from the human patient just prior to administration of the anti-CD5 ADC. In one embodiment, the level of endogenous T cells is determined one day or less prior to administration of the anti-CD5 ADC.

Levels of T cells can be determined according to standard methods known in the art, including, but not limited, to fluorescence-activated cell sorting (FACs) analysis or a hematology analyzer.

As described above, one of the advantages of the methods described herein is that lymphodepleting chemotherapeutic agents can be reduced in amount or not included in the conditioning regimen administered to a human patient having or planning on having CAR therapy. Lymphodepleting chemotherapeutic agents such as, but not limited to, fludarabine, cyclophosphamide, bendamustine, and/or pentostatin are commonly used as anti-rejection agents to promote CAR expressing cell acceptance in a human receiving CAR therapy. In certain embodiments, a human patient is administered an anti-CD5 ADC in combination with, e.g., prior to, administration of a CAR expressing immune cell (e.g., T cell) such that the human patient does not receive lymphodepleting chemotherapeutic agent, e.g., fludarabine and/or cyclophosphamide, prior to, concomitantly with, or following prior to, concomitantly with, or following administration of the CAR expressing immune cell.

The use of other immune depleting agents can also be avoided or reduced through the use of an anti-CD5 ADC as an agent to deplete a human subject's endogenous immune cells and reduce the risk of rejection of the CAR expressing immune cells. For example, alemtuzumab is commonly used as an anti-rejection agent in combination with CAR therapy to promote CAR expressing cell acceptance in the human receiving CAR therapy. In certain embodiments, a human patient is administered an anti-CD5 ADC in combination with, e.g., prior to, administration of a CAR expressing immune cell (e.g., T cell) such that the human patient does not receive alemtuzumab prior to, concomitantly with, or following administration of the CAR expressing immune cell.

In certain embodiments, an anti-CD5 ADC is used in combination with another therapy in order to promote tolerance of the CAR expressing immune cells. For example, an anti-CD2 ADC may also be administered to the human patient prior to the human patient receiving CAR therapy. The anti-CD2 ADC can be administered prior to, concomitantly with, or following the anti-CD5 ADC, where both the anti-CD2 ADC and the anti-CD5 ADC are administered to the human patient prior to CAR therapy.

The methods disclosed herein can be used both for autologous and allogeneic cells expressing CARs. Importantly, the anti-CD5 ADC conditioning methods described herein are useful for expanding the type of immune cell that can be used in CAR therapy by providing a means by which tolerance of an allogeneic cell can be provided. In one embodiment, the CAR expressing immune cell is an allogeneic cell or an autologous cell. Examples of the types of immune cells that may be engineered to express a CAR include, but are not limited to, an allogeneic T cell, an autologous T cell, an autologous NK cell, or an allogeneic NK cell.

In one embodiment, the anti-CD5 antibody-drug conjugate is used to deplete CD5 expressing donor cells, e.g., activated T cells expressing CD5, by administering the anti-CD5 antibody-drug conjugate after the administration of CAR cell therapies. In one embodiment, the CAR cell therapies comprise allogeneic cells.

The methods disclosed herein are particularly useful for the treatment of cancer or an autoimmune disease in a human subject having one of these disorders.

In one embodiment, the methods disclosed herein are used to treat cancer. More specifically, an anti-CD5 ADC is administered to a human subject having cancer in combination with CAR therapy. Examples of the types of cancer that can be treated using the methods disclosed herein include, but are not limited to, adult advanced cancer, pancreatic cancer, non-resectable pancreatic cancer, colorectal cancer, metastatic colorectal cancer, ovarian cancer, triple-negative breast cancer, hematopoietic/lymphoid cancer, colon cancer liver metastasis, small cell lung cancer, non-small cell lung cancer, B-cell lymphoma, relapsed or refractory B-cell lymphoma, follicular lymphoma, mantle cell lymphoma, diffuse large cell lymphoma, relapsed or refractory diffuse large cell lymphoma, anaplastic large cell lymphoma, primary mediastinal B-cell lymphoma, recurrent mediastinal, refractory mediastinal large B-cell lymphoma, large B-cell lymphoma, Hodgkin lymphoma, non-Hodgkin lymphoma, relapsed or refractory non-Hodgkin lymphoma, refractory aggressive non-Hodgkin lymphoma, B-cell non-Hodgkin lymphoma, refractory non-Hodgkin lymphoma, colorectal carcinoma, gastric carcinoma, pancreatic carcinoma, triple-negative invasive breast carcinoma, renal cell carcinoma, lung squamous cell carcinoma, hepatocellular-carcinoma, urothelial carcinoma, leukemia, B-cell leukemia, B-cell acute lymphocytic leukemia, B-cell acute lymphoblastic leukemia, adult acute lymphoblastic leukemia, B-cell prolymphocytic leukemia, childhood acute lymphoblastic leukemia, refractory childhood acute lymphoblastic leukemia, acute leukemia, acute lymphoblastic leukemia, acute lymphocytic leukemia, prolymphocytic leukemia, chronic lymphocytic leukemia, acute myeloid leukemia, recurrent plasma cell myeloma, refractory plasma cell myeloma, multiple myeloma, relapsed or refractory multiple myeloma, multiple myeloma of bone, malignant glioma of brain, myelodysplastic syndrome, EGFR-positive colorectal cancer, glioblastoma multiforme, neoplasms, blastic plasmacytoid dendritic cell neoplasms, liver metastases, solid tumors, advanced solid tumors, mesothelin positive tumors, hematological malignancies, and other advanced malignancies.

In one embodiment, the methods disclosed herein are used to treat an autoimmune disease. More specifically, an anti-CD5 ADC is administered to a human subject having an autoimmune disease in combination with CAR therapy. Examples of autoimmune diseases that can be treated using the combination methods disclosed herein include, but are not limited to, multiple sclerosis, Crohn's disease, ulcerative colitis, rheumatoid arthritis, type 1 diabetes, lupus, and psoriasis.

In certain embodiments, an anti-CD5 ADC is administered to a human patient in combination with a CAR-T cell therapy. In one embodiment, the anti-CD5 ADC is administered to the human patient prior to administration of the CAR-T therapy. Examples of CAR-T cells that could be used in combination with the anti-CD5 ADC therapy described herein include, but are not limited to, CD19 CAR-T (e.g., CART-19-01,02,03 (Fujian Medical University); daopeicart (Hebei Senlang Biotechnology Inc.); IM19CART/001, YMCART201702 (Beijing Immunochina Medical Science & Technology Co.); CART-CD19-02,03 (Wuhan Sian Medical Technology Co.); Universal CD19-CART/SHBYCL001,002 (Shanghai Bioray Laboratory Inc.); UnicarTherapy201701 (Shanghai Unicar-Therapy Biomedicine Technology Co.); Genechem/NCT02672501 (Shanghai GeneChem Co.); SenL_19 (Hebei Senlang Biotechnology Inc.); PCAR-019 (PersonGen BioTherapeutics (Suzhou); ICAR19 (Immune Cell, Inc.); WM-CART-02 (Sinobioway Cell Therapy Co.); HenanCH080,109,152 (Henan Cancer Hospital/The Pregene (ShenZhen) Biotechnology Co.); IM19-CD28 and IM19-41BB CAR-T cells (Beijing Immunochina Medical Science & Technology Company); CTL019/IT1601-CART19 (Beijing Sanwater Biological Technology Co.); CTL019/CCTL019C2201 (Novartis Pharmaceuticals); CD19:4-1BB:CD28:CD3/FirstShenzhen01 (Shenzhen Second People's Hospital/The Beijing Pregene Science and Technology Company); MB-CART19.1 (Shanghai Children's Medical Center/Miltenyi Biotec GmbH); PZ01 CAR-T cells (Pinze Lifetechnology Co.); YMCART201701 (Beijing Immunochina Medical Science & Technology Co.); 2016YJZ12 (Peking University/Marino Biotechnology Co.); EGFRt/19-28z/4-1BBL CAR T cells (Memorial Sloan Kettering Cancer Center/Juno Therapeutics, Inc.); Doing-002 (Beijing Doing Biomedical Co.); PCAR-019 (PersonGen BioTherapeutics (Suzhou) Co.); C-CAR011 (Peking Union Medical College Hospital/Cellular Biomedicine Group Ltd.); iPD1 CD19 eCAR T cells (Peking University/Marino Biotechnology Co.); 2013-1018/NCT02529813 (M.D. Anderson Cancer Center/Ziopharm/Intrexon Corp.); HenanCH CAR 2-1 (Henan Cancer Hospital/The Pregene (ShenZhen) Biotechnology Co.); JCAR015 (Juno Therapeutics, Inc.); JCAR017/017001,004, 006 (Juno Therapeutics, Inc.); JCAR017 (Celgene); TBI-1501 (Takara Bio Inc.); JMU-CD19CAR (Jichi Medical University); KTE-C19 (Kite, A Gilead Company); TriCAR-T-CD19 (Timmune Biotech Inc.); PF-05175157 (Fred Hutchinson Cancer Research Center)); CD22/CD30/CD7/BCMA/CD123 (e.g., 2016040/NCT03121625 (Hebei Senlang Biotechnology Inc.)); CD22 (e.g., Ruijin-CAR-01 (Ruijin Hospital/Shanghai Unicar-Therapy Bio-medicine Technology Co.); AUTO-PA1,DB1 (Autolus Limited)), CD20 (e.g., Doing-006 (Beijing Doing Biomedical Co.)); or CD20/CD22/CD30 (e.g., SZ5601 (The First Affiliated Hospital of Soochow University Shanghai/Unicar-Therapy Bio-medicine Technology Co.)).

Chimeric Antigen Receptors (CARs)

The present invention includes the use of CAR therapy in combination with an anti-CD5 immune suppressing ADC. The invention is not generally limited to a specific CAR construct, e.g., a specific antigen binding region or intracellular signaling domain, as the invention is based, at least in part, on the discovery that anti-CD5 ADCs can serve as a conditioning agent for CAR therapy by promoting acceptance of CAR expressing cells by ablating endogenous CD5+ immune cells, such as endogenous T cells. Specific CARs, e.g., CD19 specific CARs, are contemplated herein and are included in the methods disclosed herein, but are not meant to be limiting.

CAR constructs are known in the art and generally contain (a) an extracellular region comprising an antigen binding domain, (b) a transmembrane domain and (c) a cytoplasmic signaling domain. Exemplary CAR configurations are known in the art, and any suitable configuration can be used in the methods described herein. For example, the CAR may be a first generation, a second generation, or a third generation CAR, e.g., as described in Guedan et al. *Molecular Therapy—Methods & Clinical Development.* 12: 145-156 (2019) or Sadelain et al. *Cancer discovery* 3.4: 388-398 (2013), the entire contents of which are hereby incorporated by reference. Briefly, a "first generation" CAR can comprise an (a) extracellular antigen binding domain, (b) a transmembrane domain, (c) one or more intracellular signaling domains, and optionally (d) a hinge region connecting the antigen binding domain to the transmembrane domain. A "second generation" CAR can comprise elements (a), (b), (c), and optionally (d), and further includes a co-stimulatory domain, for example, a co-stimulatory domain of CD28 or 4-1BB. A "third generation" CAR can comprise elements (a), (b), (c), and optionally (d), and further includes multiple co-stimulatory domains, for example, the co-stimulatory domains of CD28 and 4-1BB, or the co-stimulatory domains of CD28 and OX40. Each of the foregoing elements is described in detail below. It should be appreciated that in some embodiments, CAR molecules described by the following exemplary, non-limiting arrangements are from left to right, N-terminus to C-terminus of the CAR. A CAR as described by the disclosure may comprise or further comprise any other combination of elements as described herein.

The CAR used in the methods disclosed herein can include an extracellular antigen binding domain. The extracellular antigen binding domain can be any molecule that binds to an antigen, including, but not limited to, a human antibody, a humanized antibody, or any a functional fragment thereof. In certain embodiments, the antigen binding domain is an scFv. In other embodiments, the extracellular antigen binding domain is a non-immunoglobulin scaffold protein. In other embodiments, the extracellular binding domain of the CAR comprises a single chain T cell receptor (scTCR). As described in U.S. Pat. Nos. 5,359,046, 5,686,281 and 6,103,521, the extracellular domain may also be obtained from any of the wide variety of extracellular domains or secreted proteins associated with ligand binding and/or signal transduction.

The choice of the molecular target (antigen) of the extracellular binding domain depends upon the type and number of ligands that define the surface of a target cell. For example, the antigen binding domain may be chosen to recognize a ligand that acts as a cell surface marker on target cells associated with a particular disease state. Thus, in one aspect, the CAR-mediated immune cell (e.g., T-cell) response can be directed to an antigen of interest by way of engineering an extracellular antigen binding domain that specifically binds a desired antigen into a CAR. For example, the antigen binding domain may be chosen to recognize a ligand that acts as a cell surface marker on target cells associated with a particular disease state, such as cancer or an autoimmune disease. Thus examples of cell surface markers that may act as ligands for the antigen binding domain in a CAR include those associated with cancer cells and other forms of diseased cells, for example, autoimmune disease cells and pathogen infected cells. In some embodiments, a CAR is engineered to target a tumor antigen of interest by way of engineering a desired antigen binding domain that specifically binds to an antigen on a tumor cell. In the context of the present invention, "tumor antigen" refers to antigens that are common to specific hyperproliferative disorders such as cancer. In one embodiment, the antigen is a tumor antigen, examples of which include, but are not limited to, CD19, CD22, CD30, CD7, BCMA, CD137, CD22, CD20, AFP, GPC3, MUC1, mesothelin, CD38, PD1, EGFR (e.g., EGFRvIII), MG7, BCMA, TACI, CEA, PSCA, CEA, HER2, MUC1, CD33, ROR2, NKR-2, PSCA, CD28, TAA, NKG2D, or CD123. In one embodiment, CAR comprises an scFv that binds to CD19, CD22, CD30, CD7, BCMA, CD137, CD22, CD20, AFP, GPC3, MUC1, mesothelin, CD38, PD1, EGFR (e.g., EGFRvIII), MG7, BCMA, TACI, CEA, PSCA, CEA, HER2, MUC1, CD33, ROR2, NKR-2, PSCA, CD28, TAA, NKG2D, or CD123.

In another aspect, the extracellular binding domain of the CAR binds to an antigen that is AFP (e.g., ETCH17AFPCAR01 (Aeon Therapeutics (Shanghai) Co./Eureka Therapeutics Inc.)), GPC3 (e.g., GeneChem GPC-3 CART (Shanghai GeneChem Co.); 302 GPC3-CART (Shanghai GeneChem Co.); CAR-T for liver cancer (Shanghai GeneChem Co.); CAR-GPC3 T cells (Carsgen Therapeutics)), MUC1 (e.g., PG-021-001,002 (PersonGen BioTherapeutics (Suzhou) Co.)), mesothelin (e.g., H2017-01-P01 (Ningbo Cancer Hospital); TAI-meso-CART (Shanghai GeneChem Co.); K16-4/NCT02930993 (China Meitan General Hospital/Marino Biotechnology Co.)), CD38 (e.g., Anti-CD38 A2 CAR-T/SOR-CART-MM-001 (Sorrento Therapeutics, Inc.)), herinCAR-PD1 (e.g., herinCAR-PD1/ NBWYKY2016-06-001,002,003 (Ningbo Cancer Hospital); SIMC-20160101,02,03 (Shanghai International Medical Center)), BCMA (e.g., P-BCMA-101 autologous T stem cell memory (Tscm) CAR-T cells/P-BCMA-101-001 (Poseida Therapeutics, Inc.); HenanCH284 (Henan Cancer Hospital/ The Pregene (ShenZhen) Biotechnology Company); LCAR-B38M CAR-T cells (Nanjing Legend Biotech Co.); 9762/ NCT03338972 (Fred Hutchinson Cancer Research Center/ Juno Therapeutics, Inc.); Descartes-08 (Cartesian Therapeutics); KITE-585 (Kite, A Gilead Company); bb21217 (bluebird bio); bb21217 (Celgene); JCARH125 (Juno Therapeutics, Inc.)), CD30 (e.g., ICAR30 T cells (Immune Cell, Inc.)), EGFR (e.g., EGFR:4-1BB:CD28:CD3 modified T cells/First Shenzhen02 (Shenzhen Sceond People's Hospital/The Beijing Pregene Science and Technology Company); EGFR-IL12-CART (Shenzhen Second People's Hospital/The Pregene (ShenZhen) Biotechnology Co.); SBNK-2016-015-01 (Beijing Sanbo Brain Hospital/Marino Biotechnology Co.)), MG7 (e.g., MG7-CART (Xijing Hospital/Shanghai GeneChem Co.)), BCMA/TACI (e.g., AUTO2-MM1 (Autolus Limited)), CEA (e.g., 383-74/ NCT02416466 (Roger Williams Medical Center/Sirtex Medical)), mesothelin/PSCA/CEA/HER2/MUC1/EGFRvIII (e.g., NCT03267173 (First Affiliated Hospital of Harbin Medical University/Shanghai Unicar-Therapy Bio-medicine Technology Co.)), CD20 (e.g., EY201605-19 (Beijing Biohealthcare Biotechnology Co.)), CD33 (e.g., 2016-0341/ NCT03126864 (M.D. Anderson Cancer Center/Intrexon Corp./Ziopharm)), EGFR/BCMA (e.g., EGFRt/BCMA-41BBz CAR T cell (Memorial Sloan Kettering Cancer Center/Juno Therapeutics, Inc.)), ROR2 (e.g., autologous CCT301-38 or CCT301-59 T cells (Shanghai Sinobioway Sunterra Biotech)), NKR-2 (e.g., CYAD-N2T-002,003,004 (Celyad)), PSCA (e.g., BP-012 (Bellicum Pharmaceuticals)), CD28 (e.g., autologous CSR T cells (Beijing Sanbo Brain Hospital/Marino Biotechnology Co.)), TAA (e.g., AMG 119 (Amgen)), NKG2D (e.g., CM-CS1 (Celyad)), or CD123 (e.g., UCART123 (Cellectis S.A.)). The foregoing sentence further provides examples of CARs that bind said antigens (e.g., AMG 119 (Amgen)). These CAR constructs may be used in the conditioning methods disclosed herein with an anti-CD5 ADC.

A CAR construct can further contain a transmembrane domain that connects (either literally or by general proximity, e.g., with spacers) the extracellular antigen binding domain to a cytoplasmic signaling domain. In some embodiments, the extracellular antigen binding domain (e.g., a scFv, Fab or other antigen binding moiety) of a CAR can be linked to a transmembrane domain using a hinge or other linker. A spacer, linker, or hinge can be introduced between the extracellular antigen binding domain and the transmembrane domain to provide the flexibility to allow the antigen-binding domain to orient in different directions, thereby facilitating antigen recognition and binding. The cytoplasmic side of the transmembrane domain can be attached to an intracellular signaling domain, such as the intracellular signaling domain of CD28 or CD3 zeta (CD3-ζ), and can additionally include one or more co-stimulatory domains as discussed below.

Thus, in certain embodiments, the CAR can further comprise a hinge region positioned between the extracellular antigen binding domain and the transmembrane domain. For example, the hinge region can be derived from the hinge region of IgG1, IgG2, IgG3, IgG4, IgA, IgD, IgE, IgM, CD28, or CD8 alpha. In one particular embodiment, the hinge region is derived from the hinge region of IgG4. In another embodiment, the hinge region is a CD8 hinge domain (see SwissProt/GenBank Acc. No. P01732).

In one embodiment, a CAR comprises an extracellular antigen binding domain and a transmembrane domain connected via a CD8 hinge: AKPTTTPAPR PPTPAPTIAS QPLSLRPEAC RPAAGGAVHT RGLDFA (SEQ ID NO: 9).

In one embodiment, a CAR comprises an extracellular antigen binding domain and a transmembrane domain connected via a hybrid CD8-CD28 hinge: AKPTTTPAPR PPTPAPTIAS QPLSLRPEAC RPAAGGAVHT RGLDFAPRKI EVMYPPPYLD NEKSNGTIIH VKGKHLCPSP LFPGPSKP (SEQ ID NO: 10).

The transmembrane domain may be derived from the sequence of a protein contributing the extracellular antigen binding domain, a protein contributing the effector function signaling domain, a protein contributing the proliferation signaling portion, or by a totally different protein. In some embodiments, the transmembrane domain is naturally associated with one of the other domains of the CAR. For example, the transmembrane domain and the cytoplasmic domain can be derived from the transmembrane region and the cytoplasmic region of the same protein. In one embodiment, the transmembrane and cytoplasmic domains of the CAR comprise contiguous portions of the CD28 sequence. Any transmembrane domain may be used in the CAR constructs described herein, provided that the domain is capable of anchoring a CAR comprising the antigen binding domain to a cell membrane.

The transmembrane domain may be derived either from a natural or from a synthetic source. Where the source is natural, the domain may be derived from any membrane-bound or transmembrane protein. Exemplary transmembrane domains that can be used in the methods provided herein may be derived from (e.g., comprise at least the transmembrane domain(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, LFA-1 T-cell co-receptor, CD2 T-cell co-receptor/adhesion molecule, CD8 alpha, and fragments thereof. The transmembrane domain of a protein can be identified using any method known in the art, e.g., hydrophobicity analysis, structural analysis, etc., or by using public databased, e.g., the UniProt Database.

In some embodiments, the transmembrane domain may be synthetic. In exemplary embodiments, the transmembrane domain can comprise predominantly hydrophobic residues such as leucine and valine. In one embodiment, a triplet of phenylalanine, tryptophan and valine can be positioned at each end of a synthetic transmembrane domain. Optionally, a short oligo- or polypeptide linker, preferably between 2 and 10 amino acids in length may form the linkage between the transmembrane domain and the cytoplasmic signaling domain of a CAR. A glycine-serine doublet provides a particularly suitable linker.

In some embodiments, the transmembrane domain in the CAR used herein is the CD8 transmembrane domain, or a portion thereof. Sequences of CD8 for this purpose are taught in PCT Publication No. W02014/055771A1.

In some embodiments, the transmembrane domain in the CAR is the CD8 transmembrane domain, or a functional portion thereof. For example, a CAR can comprise a CD3 transmembrane domain having an amino acid sequence of LDPKLCYLLD GILFIYGVIL TALFLRVK (SEQ ID NO: 11), or a functional portion thereof, such as LCYLLDGILF IYGVILTALF L (SEQ ID NO: 12).

In some embodiments, the transmembrane domain in the CAR of the invention is a CD28 transmembrane domain. An exemplary sequence of CD28 is provided below, as well as an exemplary transmembrane domain sequence. In some embodiments, the CD28 transmembrane domain comprises the exemplary transmembrane domain sequence below, or a fragment or variant thereof that is capable of anchoring a CAR comprising the sequence to a cell membrane. Thus, in some embodiments, the transmembrane domain of the CAR is a CD28 transmembrane domain containing the following amino acid sequence: FWVLVVVGGVLACYSLL-VTVAFIIFWV (SEQ ID NO: 13). In one embodiment, the transmembrane domain of the CAR is a CD28 transmembrane domain containing the following amino acid sequence: IEVMYPPPYL DNEKSNGTII HVKGKHLCPS PLFPGPSKPF WVLVVVGGVL ACYSLLVTVA FIIFWV (SEQ ID NO: 16), or a functional fragment thereof, e.g., SEQ ID NO: 14.

In addition to an extracellular antigen binding domain and a transmembrane domain, a CAR further comprises an intracellular (or cytoplasmic) signaling domain.

It is known that signals generated through the endogenous TCR alone are insufficient for full activation of the T cell and that a secondary or co-stimulatory signal may also be required. Thus, T cell activation can be mediated by two distinct classes of cytoplasmic signaling sequences: those that initiate antigen-dependent primary activation through the TCR (primary cytoplasmic signaling sequences) and those that act in an antigen-independent manner to provide a secondary or co-stimulatory signal (secondary cytoplasmic signaling sequences).

An "intracellular signaling domain" or "cytoplasmic signaling domain" as the terms are used herein, refers to an intracellular portion of a molecule. The intracellular signaling domain can generate a signal that promotes an immune effector function of the CAR containing immune cell, e.g., a CAR-T cell or CAR-expressing NK cell. Examples of immune effector function, e.g., in a CART cell or CAR-expressing NK cell, include cytolytic activity and helper activity, including the secretion of cytokines. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In one embodiment, the intracellular signaling domain of the CAR contains a CD3 zeta signaling region as described in SEQ ID NO: 15, or a signaling portion thereof:

```
                                            (SEQ ID NO: 15)
RVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYD

ALHMQALPPR
```

Cytoplasmic signaling domains further can include, but are not limited to, those derived from CD3 zeta, FcR gamma, FcR beta, CD3 gamma, CD3 delta, CD3 epsilon, CD5, CD22, CD79a, CD79b, CD278 ("ICOS"), Fc-epsilon-RI, CD66d, DAP10, and DAP12.

A CAR may further contain an "intracellular costimulatory domain" which is a polypeptide chain derived from an intracellular signaling domain of a costimulatory protein or proteins, such as CD28 and 4-1BB, that enhance cytokine production.

Exemplary co-stimulatory signaling regions include 4-1BB, CD21, CD28, CD27, CD127, ICOS, IL-15Rα, and OX40.

In certain embodiments, the cytoplasmic costimulatory domain of a CAR comprises the 4-1BB signaling domain by itself or combined with any other desired cytoplasmic domain(s) useful in the context of a CAR. 4-1BB is a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank acc no. AAA62478.2, or the equivalent residues from a non-human species, e.g., mouse, rodent, monkey, ape and the like.

In one embodiment, the intracellular costimulatory signaling domain of the CAR is a 4-1BB (CD137) co-stimulatory signaling region, or a signaling portion thereof:

```
                                            (SEQ ID NO: 60)
KRGRKKLLYIFKQPFMRPVQTTQEEDGCSCRFPEEEEGGCEL
```

In one embodiment, the costimulatory signaling domain of the CAR is a CD28 co-stimulatory signaling region sequence. For example, the costimulatory signaling domain can comprise the following CD28 co-stimulatory signaling region, or a signaling portion thereof:

```
                                            (SEQ ID NO: 17)
RSKRSRLLHSDYMNMTPRRPGPTRKHYQPYAPPRDFAAYRS.
```

In exemplary embodiments, the cytoplasmic domain of the CAR can contain a CD3-zeta signaling domain, in combination with any other desired cytoplasmic domain(s) useful in the context of the CAR of the invention. In certain embodiments, the cytoplasmic domain of the CAR can comprise a CD3 zeta domain and a costimulatory signaling region, including, but not limited to, a costimulatory signaling region of 4-1BB, CD28, and CD27.

The cytoplasmic signaling sequences within the cytoplasmic signaling portion of the CAR of the invention may be linked to each other in a random or specified order. Optionally, a short oligo- or polypeptide linker or spacer, preferably between 5 and 20 amino acids in length may be inserted between cytoplasmic domains. A GGGGS (SEQ ID NO: 18) or (GGGGS)×3 (SEQ ID NO: 19) provides a particularly suitable linker.

In one embodiment, a CAR used herein includes an extracellular domain containing a single chain variable domain of an anti-CD19 monoclonal antibody, a transmembrane domain containing a hinge and transmembrane domain of CD8α, and a cytoplasmic domain containing the signaling domain of CD3ζ and the signaling domain of 4-1BB. An exemplary CAR includes an extracellular domain include the anti-CD19 monoclonal antibody which is described in Nicholson I C, et al., Mol Immunol 34:1157-1165 (1997) plus the 21 amino acid signal peptide of CD8α (translated from 63 nucleotides at positions 26-88 of Gen-Bank Accession No. NM_001768). The CD8α hinge and transmembrane domain consists of 69 amino acids translated from the 207 nucleotides at positions 815-1021 of GenBank Accession No. NM_001768. The CD3 signaling domain of the preferred embodiment contains 112 amino acids translated from 339 nucleotides at positions 1022-1360 of GenBank Accession No. NM_000734.

Between the extracellular domain (comprising the antigen binding domain) and the transmembrane domain of the CAR (described above), or between the cytoplasmic domain and the transmembrane domain of the CAR, there may be incorporated a spacer or hinge domain. As used herein, the term "spacer domain" generally means any oligo- or polypeptide that functions to link the transmembrane domain to the extracellular domain and/or the cytoplasmic domain in the polypeptide chain. As used herein, a hinge domain generally means any oligo- or polypeptide that functions to provide flexibility to the CAR, or domains thereof, and/or prevent steric hindrance of the CAR, or domains thereof. In some embodiments, a spacer or hinge domain may comprise up to 300 amino acids, preferably 10 to 100 amino acids and most preferably 5 to 20 amino acids. It also should be appreciated that one or more spacer domains may be included in other regions of a CAR, as aspects of the disclosure are not limited in this respect.

It is to be understood that a CAR can include a region (e.g., an antigen binding domain, a transmembrane domain, a cytoplasmic domain, a signaling domain, a safety domain, and/or a linker, or any combination thereof) having a sequence provided herein or a variant thereof or a fragment of either one thereof (e.g., a variant and/or fragment that retains the function required for the CAR activity) can be included in a CAR protein as described herein. In some embodiments, a variant has 1, 2, 3, 4, 5, 6, 7, 8, 9, or 10 amino acid changes relative to the illustrated sequence. In some embodiments, a variant has a sequence that is at least 80%, at least 85%, at least 90%, 90%-95%, at least 95% or at least 99% identical to the illustrated sequence. In some embodiments, a fragment is 1-5, 5-10, 10-20, 20-30, 30-40, or 40-50 amino acids shorter than a sequence provided herein. In some embodiments, a fragment is shorter at the N-terminal, C-terminal, or both terminal regions of the sequence provided. In some embodiments, a fragment contains 80%-85%, 85%-90%, 90%-95%, or 95%-99% of the number of amino acids in a sequence provided herein.

In some embodiments, the above exemplary, non-limiting arrangements are from left to right, N-terminus to C-terminus of the CAR. The CAR may comprise or further comprise any other combination of elements as described herein.

Once the CAR construct is identified with its various parts, a CAR expressing immune cell is produced whereby the immune cell expresses the CAR. The method includes introducing into, e.g., transducing, the immune cell with a nucleic acid molecule described herein (e.g., an RNA molecule, e.g., an mRNA), or a vector comprising a nucleic acid molecule encoding a CAR, e.g., a CAR described herein. Notably, included in the invention are nucleic acids encoding the amino acid sequences disclosed herein. The present invention also provides a method of generating a population of cells (e.g., RNA-engineered cells transiently expressing an exogenous RNA). The method includes introducing into the cell an RNA as described herein (e.g., an in vitro transcribed RNA or synthetic RNA; an mRNA sequence encoding a CAR polypeptide as described herein). In embodiments, the RNA expresses the CAR polypeptide transiently. In one embodiment, the cell is a cell as described herein, e.g., an immune effector cell (e.g., T cells or NK cells, or cell population).

Other exemplary chimeric antigen receptor constructs are disclosed in U.S. Pat. Nos. 9,328,156; 9,783,591; 9,714,278; 9,765,156; 10,117,896; 9,573,988; 10,308,717; 10,221,245; 10,040,865; U.S. Patent Publication No. 2018/0256712A1; U.S. Patent Publication No. 2018/0271907A1; U.S. Patent Publication No. 2016/0046724A1; U.S. Patent Publication No. 2018/0044424A1; U.S. Patent Publication No. 2018/0258149A1; U.S. Patent Publication No. 2019/0151363A1; and U.S. Patent Publication No. 2018/0273601A1; the contents of each of the foregoing patents and patent publications are incorporated by reference herein in their entirety.

III. Anti-CD5 Antibody Drug Conjugates (ADCs)

As described herein, anti-CD5 ADCs can be used in combination with CAR therapy to treat cancer or an autoimmune disease in a human patient. More specifically, anti-CD5 ADCs can be used to deplete CD5+ cells (e.g., CD5+ T cells) in a human subject who is also receiving CAR therapy. Anti-CD5 ADCs target endogenous T cells and kill these cells such that the patient's immune system will not attack the CAR expressing immune cells (autologous or allogeneic) administered to the subject. Thus, anti-CD5 ADCs are used as a conditioning step in combination with CAR therapy to promote acceptance of the engineered CAR expressing immune cells in the recipient patient. One advantage of using anti-CD5 ADCs as a conditioning regimen is that endogenous T cells expressing CD5 can be specifically targeted for depletion versus more traditional methods of conditioning for CAR therapy where general lymphodepleting chemotherapeutic agents are administered to the subject.

Anti-CD5 Antibodies

ADCs capable of binding CD5 can be used as therapeutic agents to promote acceptance in a human patient of immune cells expressing CARs by preventing or reducing the risk of rejection of the immune cells expressing CARs.

The anti-CD5 ADCs described herein include an anti-CD5 antibody or antigen binding portion thereof, linked to a cytotoxin.

Human CD5 is also referred to as Lymphocyte Antigen T1, T1, Leu-1, and LEU1. CD5 is expressed on human T cells. Two isoforms of human CD5 have been identified. Isoform 1 contains 495 amino acids and is described in Gladkikh et al (2017) *Cancer Med.* 6(12):2984 and Jones et al. (1986) *Nature* 323 (6086): 346). The amino acid sequence of CD5 (isoform 1) is provided below (NCBI Reference Sequence: NP_055022.2):

```
                                          (SEQ ID NO: 20)
mpmgslqpla tlyllgmlva sclgrlswyd pdfqarltrs nskcqgqlev ylkdgwhmvc sqswgrsskq wedpsqaskv cqrlncgvpl slgpflvtyt pqssiicygq lgsfsncshs rndmchslgl tclepqkttp pttrpppttt peptapprlq lvaqsggqhc agvvefysgs lggtisyeaq dktqdlenfl cnnlqcgsfl khlpeteagr aqdpgepreh qplpiqwkiq nssctslehc frkikpqksg rvlallcsgf qpkvqsrlvg gssicegtve vrqgaqwaal cdsssarssl rweevcreqq cgsvnsyrvl dagdptsrgl fcphqklsqc helwernsyc kkvfvtcqdp npaglaagtv asiilalvll vvllvvcgpl aykklvkkfr qkkqrqwigp tgmnqnmsfh rnhtatvrsh
```

```
aenptashvd neysqpprns hlsaypaleg alhrssmqpd nssdsdydlh gaqrl
```

A second isoform of human CD5 is 438 amino acids and is identified below as NCBI Reference Sequence: NP_001333385.1. Unlike isoform 1, CD5 isoform 2 is an intracellular protein. Isoform 2 contains a distinct 5' UTR and lacks an in-frame portion of the 5' coding region, compared to isoform 1. The resulting isoform 2 has a shorter N-terminus, compared to isoform 1. The CD5 isoform 2 lacks the leader peptide, compared to isoform 1 and represents an intracellular isoform found in a subset of B lymphocytes. The ADCs described herein are specific for human CD5 isoform 1 which represents the extracellular version of human CD5.

In one embodiment, an anti-CD5 antibody that may be used in the methods and compositions described herein is Antibody 5D7v (Ab5D7v). The heavy chain variable region (VH) amino acid sequence of Ab5D7v is provided below as SEQ ID NO: 1.

```
                                           (SEQ ID NO: 1)
QVTLKESGPVLVKPTETLTLTCTFSGFSLSTSGMGVGWIRQAPGKGLEWVA

HIWWDDDVYYNPSLKSRLTITKDASKDQVSLKLSSVTAADTAVYYCVRRRA

TGTGFDYWGQGTLVTVSS
```

The VH CDR amino acid sequences of Ab5D7v are underlined above and are as follows:

```
                                      (VH CDR1; SEQ ID NO: 3)
        FSLSTSGMG;

(VH CDR2; SEQ ID NO: 4)
        WWDDD;
        and (VH CDR3; SEQ ID NO: 5)
        RRATGTGFDY.
```

The light chain variable region (VL) amino acid sequence of Ab5D7v is provided below as SEQ ID NO 2.

```
                                           (SEQ ID NO: 2)
NIVMTQSPSSLSASVGDRVTITCQASQDVGTAVAWYQQKPDQSPKLLIYWT

STRHTGVPDRFTGSGSGTDFTLTISSLQPEDIATYFCHQYNSYNTFGSGTK

LEIK
```

The VL CDR amino acid sequences of Ab5D7v are underlined above and are as follows:

```
                                      (VL CDR1; SEQ ID NO: 6)
        QDVGTA;
                                      (VL CDR2; SEQ ID NO: 7)
        WTSTRHT;
        and
                                      (VL CDR3; SEQ ID NO: 8)
        YNSYNT.
```

In one embodiment, an anti-CD5 ADC comprises an anti-CD5 antibody comprising a heavy chain comprising a CDR1 domain comprising the amino acid sequence set forth in SEQ ID NO: 3, a CDR2 domain comprising the amino acid sequence set forth in SEQ ID NO: 4, and a CDR3 domain comprising the amino acid sequence set forth in SEQ ID NO: 5, and comprises a light chain comprising a CDR1 domain comprising the amino acid sequence set forth in SEQ ID NO: 6, a CDR2 domain comprising the amino acid sequence set forth in SEQ ID NO: 7, and a CDR3 domain comprising the amino acid sequence set forth in SEQ ID NO: 8, wherein the antibody is conjugated to a cytotoxin via a linker.

In one embodiment, an anti-CD5 ADC comprises an anti-CD5 antibody comprising a heavy chain comprising a variable region comprising an amino acid sequence as set forth in SEQ ID NO: 1, and a light chain comprising a variable region comprising an amino acid sequence as set forth in SEQ ID NO: 2, wherein the antibody is conjugated to a cytotoxin via a linker.

In another embodiment, an anti-CD5 antibody used in the ADCs described herein is the 5D7 antibody (see, e.g., US 20080254027, the disclosure of which is incorporated herein by reference). In another embodiment, an anti-CD5 antibody that may be used in the methods and compositions (including ADCs) described herein is a variant of the 5D7 antibody (see, e.g., US 20080254027, the disclosure of which is incorporated herein by reference).

Further, in certain embodiments the anti-CD5 ADC has a serum half-life in a human subject of 3 days or less.

Additional anti-CD5 antibodies that can be used in the ADCs described herein can be identified using techniques known in the art, such as hybridoma production. Hybridomas can be prepared using a murine system. Protocols for immunization and subsequent isolation of splenocytes for fusion are known in the art. Fusion partners and procedures for hybridoma generation are also known. Alternatively, anti-CD5 antibodies can be generated using the HuMAb-Mouse® or XenoMouse™. In making additional anti-CD5 antibodies, the CD5 antigen is isolated and/or purified. The CD5 antigen may be a fragment of CD5 from the extracellular domain of CD5. Immunization of animals can be performed by any method known in the art. See, e.g., Harlow and Lane, Antibodies: A Laboratory Manual, New York: Cold Spring Harbor Press, 1990. Methods for immunizing animals such as mice, rats, sheep, goats, pigs, cattle and horses are well known in the art. See, e.g., Harlow and Lane, supra, and U.S. Pat. No. 5,994,619. The CD5 antigen may be administered with an adjuvant to stimulate the immune response. Adjuvants known in the art include complete or incomplete Freund's adjuvant, RIBI (muramyl dipeptides) or ISCOM (immunostimulating complexes). After immunization of an animal with a CD5 antigen, antibody-producing immortalized cell lines are prepared from cells isolated from the immunized animal. After immunization, the animal is sacrificed and lymph node and/or splenic B cells are immortalized by methods known in the art (e.g., oncogene transfer, oncogenic virus transduction, exposure to carcinogenic or mutating compounds, fusion with an immortalized cell, e.g., a myeloma cell, and inactivating a tumor suppressor gene. See, e.g., Harlow and Lane, supra. Hybridomas can be selected, cloned and further screened for desirable characteristics, including robust growth, high antibody production and desirable antibody characteristics.

Anti-CD5 antibodies for use in the anti-CD5 ADCs described herein can also be identified using high throughput screening of libraries of antibodies or antibody fragments for molecules capable of binding CD5. Such methods include in vitro display techniques known in the art, such as phage display, bacterial display, yeast display, mammalian cell display, ribosome display, mRNA display, and cDNA display, among others. The use of phage display to isolate antibodies, antigen-binding fragments, or ligands that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules. In addition, functional antibody fragments, such as Fab and scFv fragments, have been expressed in in vitro display formats (see, for example, McCafferty et al., Nature 348: 552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules).

In addition to in vitro display techniques, computational modeling techniques can be used to design and identify anti-CD5 antibodies or antibody fragments in silico, for instance, using the procedures described in US 2013/0288373, the disclosure of which is incorporated herein as it pertains to molecular modeling methods for identifying anti-CD5 antibodies. For example, using computational modeling techniques, one of skill in the art can screen libraries of antibodies or antibody fragments in silico for molecules capable of binding specific epitopes on CD5, such as extracellular epitopes of CD5.

In one embodiment, the anti-CD5 antibody used in the ADCs described herein are able to internalize into the cell. In identifying an anti-CD5 antibody (or fragment thereof) additional techniques can be used to identify antibodies or antigen-binding fragments that bind CD5 on the surface of a cell (e.g., a T cell) and further are able to be internalized by the cell, for instance, by receptor-mediated endocytosis. For example, the in vitro display techniques described above can be adapted to screen for antibodies or antigen-binding fragments thereof that bind CD5 on the surface of a hematopoietic stem cell and that are subsequently internalized. Phage display represents one such technique that can be used in conjunction with this screening paradigm. To identify anti-CD5 antibodies or fragments thereof that bind CD5 and are subsequently internalized a CD5+ cell, one of skill in the art can use the phage display techniques described in Williams et al., Leukemia 19:1432-1438, 2005, the disclosure of which is incorporated herein by reference in its entirety.

The internalizing capacity of an anti-CD5 antibody or fragment thereof can be assessed, for instance, using radionuclide internalization assays known in the art. For example, an anti-CD5 antibody or fragment thereof, identified using in vitro display techniques described herein or known in the art can be functionalized by incorporation of a radioactive isotope, such as $^{18}$F, $^{75}$Br, $^{77}$Br, $^{122}$I, $^{123}$I, $^{124}$I, $^{125}$I, $^{129}$I, $^{131}$I, $^{211}$At, $^{67}$Ga, $^{111}$In, $^{99}$Tc, $^{169}$Yb, $^{186}$Re, $^{64}$Cu, $^{67}$Cu, $^{177}$Lu, $^{77}$As, $^{72}$As, $^{86}$Y, $^{90}$Y, $^{89}$Zr, $^{212}$Bi, $^{213}$Bi, or $^{225}$Ac. For instance, radioactive halogens, such as $^{18}$F, $^{75}$Br, $^{77}$Br, $^{122}$I, $^{123}$I, $^{124}$I, $^{125}$I, $^{129}$I, $^{131}$I, $^{211}$At, can be incorporated into antibodies, fragments thereof, or ligands using beads, such as polystyrene beads, containing electrophilic halogen reagents (e.g., Iodination Beads, Thermo Fisher Scientific, Inc., Cambridge, MA). Radiolabeled antibodies, or fragments thereof, can be incubated with hematopoietic stem cells for a time sufficient to permit internalization. Internalized antibodies, or fragments thereof, can be identified by detecting the emitted radiation (e.g., γ-radiation) of the resulting hematopoietic stem cells in comparison with the emitted radiation (e.g., γ-radiation) of the recovered wash buffer. The foregoing internalization assays can also be used to characterize ADCs.

In some embodiments, the anti-CD5 antibody (or fragment thereof) has a defined serum half-life. For example, an anti-CD5 antibody (or fragment thereof) may have a serum half-life of about 1-24 hours in the human patient. ADCs containing such anti-CD5 antibodies can also, for example, have a serum half-life of about 1-24 hours in a human patient. Pharmacokinetic analysis by measurement of serum levels can be performed by assays known in the art.

For recombinant production of an anti-CD5 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR– CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003). In one embodiment, the host cell is eukaryotic, e.g. a Chinese Hamster Ovary (CHO) cell or lymphoid cell (e.g., Y0, NS0, Sp20 cell).

In some embodiments, the anti-CD5 antibodies that can be used in conjunction with the compositions and methods described herein include those that contain a combination of CDR-H1, CDR-H2, CDR-H3, CDR-L1, CDR-L2, and CDR-L3 regions set forth in Tables 1A and 1B, below.

TABLE 1A

| Ab No. | Name | CDRH1 | SEQ ID NO: | CDRH2 | SEQ ID NO: | CDRH3 | SEQ ID NO: |
|---|---|---|---|---|---|---|---|
| 1 | 1D8 | SGYSFTGYTM | 61 | LINPYNGGTT | 98 | CARDYYGSSPDFDYW | 135 |
| 2 | 3I21 | SGYSFTDYTM | 62 | LINPYNGGTM | 99 | CARDNYGSSPDFDYW | 136 |
| 3 | 4H10 | SGYSFTGYTM | 63 | LINPYNGGTM | 100 | CARDNYGSSPYFDYW | 137 |
| 4 | 8J23 | SGYSFTGYTM | 64 | LINPYNGGTM | 101 | CARDNYGSSPYFDYW | 138 |
| 5 | 5O4 | SGYSFTGYTM | 65 | LINPYNGGTT | 102 | CARDYYGSSPDFDYW | 139 |
| 6 | 4H2 | SGFTFSNYAM | 66 | SISSGGNTF | 103 | CVRYYYGVTYWYFDVW | 140 |
| 7 | 5G2 | SGFTFSSYAM | 67 | SISSGGSTY | 104 | CVRYYYGIRYWYFDVW | 141 |
| 8 | 8G8 | SGYSFTAYNI | 68 | SIDPYYGDTK | 105 | CARRMITMGDWYFDVW | 142 |
| 9 | 6M4 | SGYSFTAYSM | 69 | SIDPYYGDTK | 106 | CARRMITTGDWYFDVW | 143 |
| 10 | 2E3 | SGYTFTNFAI | 70 | LISSNSGDVS | 107 | CARHYGAHNYFDYW | 144 |
| 11 | 4E24 | SGYTFTNFAI | 71 | LISTSSGDVS | 108 | CARHYGANNYFDYW | 145 |
| 12 | 4F10 | SGYTFTNFAI | 72 | LISSNSGDVS | 109 | CARHYGAHNYFDYW | 146 |
| 13 | 7J9 | SGYTFTNFAI | 73 | LISSNSGDVS | 110 | CARHYGAHNYFDYW | 147 |
| 14 | 7P9 | SGFNIKDTYM | 74 | RIDPANGNTK | 111 | CAREENYYGTYYFDYW | 148 |
| 15 | 8E24 | SGYSFTSYWM | 75 | MIHPSDSETR | 112 | CARWGDHDDAMDFW | 149 |
| 16 | 6L18 | SGFSLTNYDV | 76 | VIWSGGNTD | 113 | CARNHGDGYFNWYFDVW | 150 |
| 17 | 7H7 | SGFSLTNYDV | 77 | VIWSGGNTD | 114 | CARNHGDGYYNWYFDVW | 151 |
| 18 | 1E7 | SGFTFSNYGM | 78 | AINSNGDITY | 115 | CARGTAWFTYW | 152 |
| 19 | 8J21 | SGYSFTGYTM | 79 | LINPYNGGTR | 116 | CARDGDDGWDIDVW | 153 |
| 20 | 7I11 | SGYIFANYGM | 80 | WINTYTGEPT | 117 | CARRGTYWHFDVW | 154 |
| 21 | 8M9 | SGYNFTNYGM | 81 | WINTYTGEPT | 118 | CARRGSYWHFDVW | 155 |
| 22 | 1P21 | SGYTFTNYGM | 28 | WINITYTGEPT | 119 | CARRSTLVFDYW | 156 |
| 23 | 2H11 | SGYTFTDYYI | 83 | WIYPGGGNTR | 120 | CARNGYWYFDVW | 157 |
| 24 | 3M22 | SGYTFTDYYI | 84 | WIYPGGGNTR | 121 | CARNGYWYFDVW | 158 |
| 25 | 5M6 | SGNTFTNFYL | 85 | CIYPGNVKTK | 122 | CAKEGDYDGTAYFDYW | 159 |
| 26 | 5H8 | SGYTFTNYGM | 86 | WINITYTGEPT | 123 | CARRDGNFDYW | 160 |
| 27 | 7I19 | SEFTFSNYAM | 87 | TISSGGSYTY | 124 | CVRHGYFDVW | 161 |
| 28 | 1A20 | SGYTFTSYRM | 88 | RIDPYDSGTH | 125 | CAFYDGAYW | 162 |
| 29 | 8E15 | SGFNIKDTYM | 89 | RIDPANGNTK | 126 | CASYDPDYW | 163 |
| 30 | 8C10 | SGYSFTDYTM | 90 | LINPYNGGTR | 127 | CARDTTATYYFDYW | 164 |
| 31 | 3P16 | SGYMFTNHGM | 91 | WINITYTGEPT | 128 | CARRVATYFDVW | 165 |
| 32 | 4F3 | SGYMFTNYGM | 92 | WINITYTGEPT | 129 | CTRRSHITLDYW | 166 |
| 33 | 5M24 | SGYIFTNYGM | 93 | WINITYTGEPT | 130 | CARRRTTAFDYW | 167 |
| 34 | 5O24 | SGFNIKDYYI | 94 | WIDPENGRTE | 131 | CNNGNYVRHYYFDYW | 168 |
| 35 | 7B16 | SGYTFINYGM | 95 | WINITYTGEPT | 132 | CTRRREITFDYW | 169 |

TABLE 1A-continued

| Ab No. | Name | CDRH1 | SEQ ID NO: | CDRH2 | SEQ ID NO: | CDRH3 | SEQ ID NO: |
|---|---|---|---|---|---|---|---|
| 36 | 1E8 | SGYTFTDYFI | 96 | EIYPGSSNTY | 133 | CARSGISPFTYW | 170 |
| 37 | 2H16 | SGYIFTGYNI | 97 | AVYPGNGDTS | 134 | CAKYDRFFASW | 171 |

TABLE 1B

| Ab No. | Name | CDRL1 | SEQ ID NO: | CDRL2 | SEQ ID NO: | CDRL3 | SEQ ID NO: |
|---|---|---|---|---|---|---|---|
| 1 | 1D8 | SQGISNHL | 172 | YFTSS | 209 | CQQYSNLPYTF | 246 |
| 2 | 3I21 | SQURNYL | 173 | YFTSS | 210 | CQQYSNLPYTF | 247 |
| 3 | 4H10 | SQGISNHL | 174 | YFTSS | 211 | CQQYSNLPYTF | 248 |
| 4 | 8J23 | SQGINNYL | 175 | YYTSS | 212 | CQQYSKIPYTC | 249 |
| 5 | 5O4 | SQGISNHL | 176 | YFTSS | 213 | CQQYSNLPYTF | 250 |
| 6 | 4H2 | SQSVDHDGDSYM | 177 | YAASN | 214 | CQQNYEDPTF | 251 |
| 7 | 5G2 | SQSVDYDGDSYM | 178 | YAASN | 215 | CQQSNEDPTF | 252 |
| 8 | 8G8 | SQDISNYL | 179 | YYTSR | 216 | CQQGDALPWTF | 253 |
| 9 | 6M4 | SQDISTYL | 180 | FYTSR | 217 | CQQGNSLPFTF | 254 |
| 10 | 2E3 | TSSISSSYL | 181 | YGTSN | 218 | CQQWSSRPPTF | 255 |
| 11 | 4E24 | NSSVSSSYL | 182 | YGTSN | 219 | CQQYSGYPLTF | 256 |
| 12 | 4F10 | TSSISSSYL | 183 | YGTSN | 220 | CQQYSDYPLTF | 257 |
| 13 | 7J9 | TSSISSSYL | 184 | YGTSN | 221 | CQQRSYFPFTF | 258 |
| 14 | 7P9 | SENIYYNL | 185 | YNANS | 222 | CKQVYDVPFTF | 259 |
| 15 | 8E24 | SENIYGYF | 186 | YNAKT | 223 | CQHHYGTPFTF | 260 |
| 16 | 6L18 | SQDINNYI | 187 | HYTST | 224 | CLQYDNLWTF | 261 |
| 17 | 7H7 | SQDINKYI | 188 | HYTST | 225 | CLQYDNLWTF | 262 |
| 18 | 1E7 | SENIYSYL | 189 | YNAKT | 226 | CQHHYGYPYTF | 263 |
| 19 | 8J21 | SQGIRNYL | 190 | YHTST | 227 | CQQYSNLPLTF | 264 |
| 20 | 7I11 | SQDVRTDV | 191 | YSASF | 228 | CQQHYTSPWTF | 265 |
| 21 | 8M9 | SQDVITAV | 192 | YSASY | 229 | CQQHYSTPWTF | 266 |
| 22 | 1P21 | SQSIGTSI | 193 | KSASE | 230 | CQQSNRWPLTF | 267 |
| 23 | 2H11 | SSQSLLNQKNYL | 194 | YWAST | 231 | CQNDYDYPYTF | 268 |
| 24 | 3M22 | SSSVSSSYL | 195 | YSTSN | 232 | CHQYHRSPLTF | 269 |
| 25 | 5M6 | SENIYYNL | 196 | YNANS | 233 | CQQTFDVPWTF | 270 |
| 26 | 5H8 | SQTIGTSI | 197 | KNASE | 234 | CQQSNSWPLTY | 271 |
| 27 | 7I19 | SQSLLYSSDQKNYL | 198 | YWAST | 235 | CQQYNYPLTF | 272 |
| 28 | 1A20 | NSSVSYM | 199 | YDTSK | 236 | CQQWSSNPFTF | 273 |
| 29 | 8E15 | SENIYYNL | 200 | YNANS | 237 | CKQAYDVPWTF | 274 |
| 30 | 8C10 | SSSLSYM | 201 | YDTSN | 238 | CQQWSSFPPTF | 275 |
| 31 | 3P16 | SQRIGTSM | 202 | KSASE | 239 | CQQSNSWPLTF | 276 |

TABLE 1B -continued

| Ab No. | Name | CDRL1 | SEQ ID NO: | CDRL2 | SEQ ID NO: | CDRL3 | SEQ ID NO: |
|---|---|---|---|---|---|---|---|
| 32 | 4F3 | SQSIGTSI | 203 | KSASE | 240 | CQQSNSWPLTF | 277 |
| 33 | 5M24 | SQNIGTSI | 204 | KDASE | 241 | CQQSDSWPLTF | 278 |
| 34 | 5O24 | ISSVSYM | 205 | YATSN | 242 | CQQWSSNPRTF | 279 |
| 35 | 7B16 | SQTIATSI | 206 | KNASE | 243 | CQQSNSWPLTF | 280 |
| 36 | 1E8 | SQSLVHSNGNTYL | 207 | YKVSN | 244 | CWQNTHFPQTF | 281 |
| 37 | 2H16 | NESVEYSGTSLM | 208 | SAASN | 245 | CQQSRQVPLTF | 282 |

Cytotoxins

Various cytotoxins can be conjugated to an anti-CD5 antibody via a linker for use in the combination therapies described herein. In particular, the anti-CD5 ADCs include an antibody (or an antigen-binding fragment thereof) conjugated (i.e., covalently attached by a linker) to a cytotoxic moiety (or cytotoxin). As used herein, the terms "cytotoxin", "cytotoxic moiety", and "drug" are used interchangeably. In various embodiments, the cytotoxic moiety exhibits reduced or no cytotoxicity when bound in a conjugate, but resumes cytotoxicity after cleavage from the linker. In various embodiments, the cytotoxic moiety maintains cytotoxicity without cleavage from the linker. In some embodiments, the cytotoxic molecule is conjugated to a cell internalizing antibody, or antigen-binding fragment thereof as disclosed herein, such that following the cellular uptake of the antibody, or fragment thereof, the cytotoxin may access its intracellular target and, e.g., mediate T cell death.

ADCs of the present invention therefore may be of the general Formula I, wherein an antibody or antigen-binding fragment thereof (Ab) is conjugated (covalently linked) to linker (L), through a chemical moiety (Z), to a cytotoxic moiety ("drug," D).

Ab-(Z-L-D)$_n$      (I)

Accordingly, the antibody or antigen-binding fragment thereof may be conjugated to a number of drug moieties as indicated by integer n, which represents the average number of cytotoxins per antibody, which may range, e.g., from about 1 to about 20. Any number of cytotoxins can be conjugated to the antibody, e.g., about 1, about 2, about 3, about 4, about 5, about 6, about 7, or about 8. In some embodiments, n is from 1 to 4. In some embodiments, n is from 1 to 3. In some embodiments, n is about 2. In some embodiments, n is about 1. The average number of drug moieties per antibody in preparations of ADC from conjugation reactions may be characterized by conventional means such as mass spectroscopy, ELISA assay, and HPLC. The quantitative distribution of ADC in terms of n may also be determined. In some instances, separation, purification, and characterization of homogeneous ADC where n is a certain value from ADC with other drug loadings may be achieved by means such as reverse phase HPLC or electrophoresis.

For some anti-CD5 ADCs, n may be limited by the number of attachment sites on the antibody. For example, where the attachment is a cysteine thiol, an antibody may have only one or several cysteine thiol groups, or may have only one or several sufficiently reactive thiol groups through which a linker may be attached. Generally, antibodies do not contain many free and reactive cysteine thiol groups which may be linked to a drug moiety; primarily, cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, higher drug loading, e.g. n>5, may cause aggregation, insolubility, toxicity, or loss of cellular permeability of certain antibody-drug conjugates.

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Only the most reactive lysine groups may react with an amine-reactive linker reagent. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments.

Cytotoxins suitable for use with the compositions and methods described herein include DNA-intercalating agents, (e.g., anthracyclines), agents capable of disrupting the mitotic spindle apparatus (e.g., vinca alkaloids, maytansine, maytansinoids, and derivatives thereof), RNA polymerase inhibitors (e.g., an amatoxin, such as α-amanitin, and derivatives thereof), and agents capable of disrupting protein biosynthesis (e.g., agents that exhibit rRNA N-glycosidase activity, such as saporin and ricin A-chain), among others known in the art.

In some embodiments, the cytotoxin is a microtubule-binding agent (for instance, maytansine or a maytansinoid), an amatoxin, pseudomonas exotoxin A, deBouganin, diphtheria toxin, saporin, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof, or another cytotoxic compound described herein or known in the art.

In some embodiments, the cytotoxin of the antibody-drug conjugate is an RNA polymerase inhibitor. In some embodiments, the RNA polymerase inhibitor is an amatoxin or derivative thereof. In some embodiments, the cytotoxin of the antibody-drug conjugate as disclosed herein is an amatoxin or derivative thereof, such as an α-amanitin, β-amanitin, γ-amanitin, ε-amanitin, amanin, amaninamide, amanullin, amanullinic acid, proamanullin or a derivative thereof.

Additional details regarding cytotoxins that can be used in the anti-CD5 ADCs useful in the methods of the invention are described below.

Amatoxins

In some embodiments, the RNA polymerase inhibitor is an amatoxin or derivative thereof. In some embodiments, the cytotoxin of the antibody-drug conjugate as disclosed herein is an amatoxin or derivative thereof, such as an α-amanitin, β-amanitin, γ-amanitin, ε-amanitin, amanin, amaninamide, amanullin, amanullinic acid, proamanullin or a derivative thereof. Structures of the various naturally occurring amatoxins are represented by Formula II and accompanying Table 2, and are disclosed in, e.g., Zanotti et al., Int. J. Peptide Protein Res. 30, 1987, 450-459.

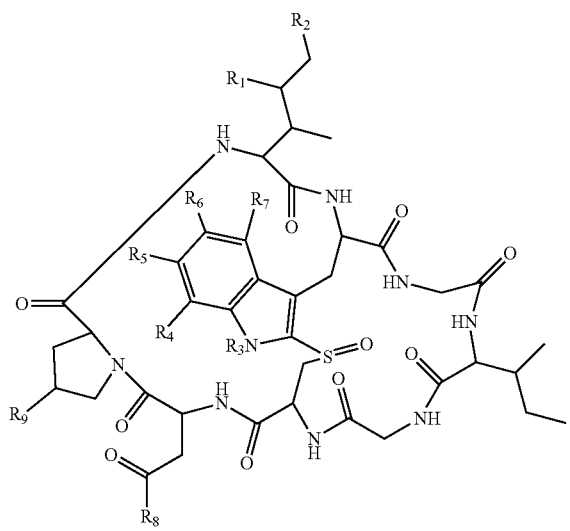

(II)

TABLE 2

Amatoxin structure table.

| Name | $R_1$ | $R_2$ | $R_3, R_4$ | $R_5$ | $R_6, R_7$ | $R_8$ | $R_9$ |
|---|---|---|---|---|---|---|---|
| α-amanitin | OH | OH | H | OH | H | $NH_3$ | OH |
| β-amanitin | OH | OH | H | OH | H | OH | OH |
| γ-amanitin | OH | H | H | OH | H | $NH_3$ | OH |
| ε-amanitin | OH | H | H | OH | H | OH | OH |
| Amanin | OH | OH | H | H | H | OH | OH |
| Amaninamide | OH | OH | H | H | H | $NH_3$ | OH |
| Amanullin | H | H | H | OH | H | $NH_3$ | OH |
| Amanullinic acid | H | H | H | OH | H | OH | OH |
| Proamanullin | H | H | H | OH | H | $NH_3$ | H |

In one embodiment, the cytotoxin is an amanitin or derivative thereof. In one embodiment, the cytotoxin is an α-amanitin or derivative thereof.

Many positions on amatoxins or derivatives thereof can serve as the position to covalently bond the linking moiety L, and, hence the antibodies or antigen-binding fragments thereof. In some embodiments, the cytotoxin in the ADC of Formula I is an amatoxin or derivative thereof according to formula (II), In one embodiment, the ADC is represented by the formula Ab-Z-L-Am, wherein Ab is an antibody or antigen-binding fragment thereof that binds CD5, L is a linker, Z is a chemical moiety, and Am is an amatoxin. In this embodiment, the linker-amatoxin conjugate Am-L-Z is represented by formula (III):

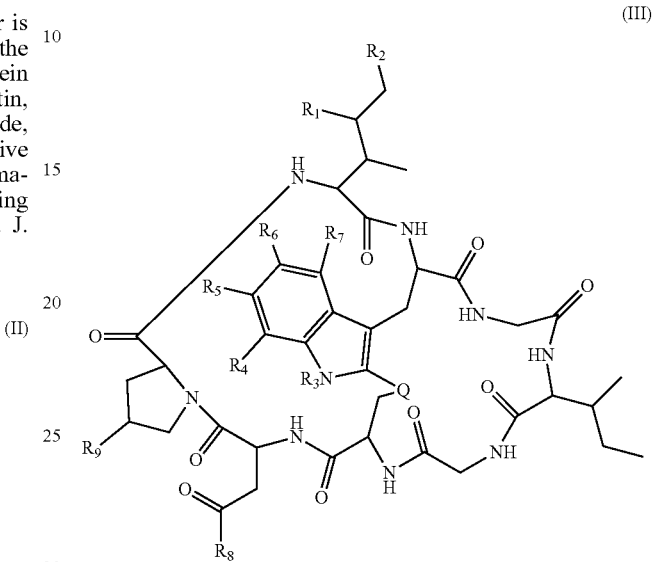

(III)

wherein:

$R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form a 5-membered heterocycloalkyl group;

$R_3$ is H, $R_C$, or $R_D$;

each of $R_4$, $R_5$, $R_6$, and $R_7$ is independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

Q is —S—, —S(O)—, or —$SO_2$—;

$R_C$ is -L-Z' or -L-Z-Ab, wherein L is a linker, and is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl; or comprises a dipeptide; or —$((CH_2)_mO)_n(CH_2)_m$—, where m and n are each independently selected from 1, 2, 3, 4, 5, 6, 7, 8, 9, and 10; Z' is a reactive moiety, and Z is a chemical moiety resulting from a coupling reaction of Z' with a functional group on Ab; and $R_D$ is $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, heteroaryl, or a combination thereof, wherein each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, or heteroaryl is optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

Formula (III) includes an amatoxin and a linker and, in some embodiments, a linker, a chemical moiety, and an antibody.

In some embodiments, the cytotoxin is an amatoxin, and the linker-amatoxin conjugate or the antibody-linker-amatoxin conjugate is represented by formula (IIIA):

(IIIA)

[Chemical structure of formula (IIIA)]

wherein:
$R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form a 5-membered heterocycloalkyl group;
$R_3$ is H, $R_C$, or $R_D$;
each of $R_4$, $R_5$, $R_6$, and $R_7$ is independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
Q is —S—, —S(O)—, or —SO$_2$—;
$R_C$ is -L-Z' or -L-Z-Ab, wherein L is a linker, and is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl; or comprises a dipeptide; or —((CH$_2$)$_m$O)$_n$(CH$_2$)$_m$—, where m and n are each independently selected from 1, 2, 3, 4, 5, 6, 7, 8, 9, and 10; Z' is a reactive moiety, and Z is a chemical moiety resulting from a coupling reaction of Z' with a functional group on Ab; and
$R_D$ is $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, heteroaryl, or a combination thereof, wherein each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, or heteroaryl is optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, the amatoxin contains one $R_C$ substituent.

In some embodiments, $R_A$ and $R_B$, together with the oxygen atoms to which they are bound, combine to form a 5-membered heterocycloalkyl group of formula:

[Chemical structure]

wherein Y is —(C=O)—, —(C=S)—, —(C=NR$_E$)—, or —(CR$_E$R$_{E'}$)—; and
wherein $R_E$ and $R_{E'}$ are each independently H, $C_1$-$C_6$ alkylene-$R_C$, $C_1$-$C_6$ heteroalkylene-$R_C$, $C_2$-$C_6$ alkenylene-$R_C$, $C_2$-$C_6$ heteroalkenylene-$R_C$, $C_2$-$C_6$ alkynylene-$R_C$, $C_2$-$C_6$ heteroalkynylene-$R_C$, cycloalkylene-$R_C$, heterocycloalkylene-$R_C$, arylene-$R_C$, or heteroarylene-$R_C$, or a combination thereof; wherein each $C_1$-$C_6$ alkylene-$R_C$, $C_1$-$C_6$ heteroalkylene-$R_C$, $C_2$-$C_6$ alkenylene-$R_C$, $C_2$-$C_6$ heteroalkenylene-$R_C$, $C_2$-$C_6$ alkynylene-$R_C$, $C_2$-$C_6$ heteroalkynylene-$R_C$, cycloalkylene-$R_C$, heterocycloalkylene-$R_C$, arylene-$R_C$, or heteroarylene-$R_C$ is optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro. Formula (IIIA) includes an amatoxin and a linker and, in some embodiments, a linker, a chemical moiety, and an antibody.

In some embodiments, the cytotoxin is an amatoxin or derivative thereof, and the amatoxin-linker conjugate is represented by formula IIIA, wherein
$R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form:

[Chemical structure]

wherein $R_3$ is H or $R_C$.

In some embodiments, the cytotoxin is an amatoxin or derivative thereof and the amatoxin-linker conjugate is represented by formula IIIA, wherein
$R_1$ is H, OH, $OR_A$, or $OR_C$;
$R_2$ is H, OH, $OR_B$, or $OR_C$;

$R_A$ and $R_B$, when present, together with the oxygen atoms to which they are bound, combine to form:

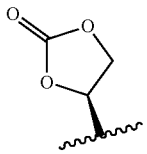

wherein
$R_3$ is H or $R_C$;
$R_4$ and $R_5$ are each independently H, OH, $OR_C$, $R_C$, or $OR_D$;
$R_6$ and $R_7$ are each H;
$R_8$ is OH, $NH_2$, $OR_C$, or $NHR_C$;
$R_9$ is H or OH; and
wherein $R_C$ and $R_D$ are as defined above.

In some embodiments, the cytotoxin is an amatoxin or derivative thereof and the amatoxin-linker conjugate is represented by formula IIIA, wherein:
$R_1$ is H, OH, or $OR_A$;
$R_2$ is H, OH, or $OR_B$;
$R_A$ and $R_B$, when present, together with the oxygen atoms to which they are bound, combine to form:

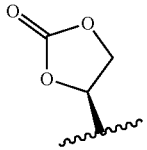

wherein
$R_3$, $R_4$, $R_6$, and $R_7$ are each H;
$R_5$ is $OR_C$;
$R_8$ is OH or $NH_2$;
$R_9$ is H or OH;
Q is —S—, —S(O)—, or —$SO_2$—; and
wherein $R_C$ and $R_D$ are as defined above. Such amatoxin-linker conjugates are described, for example, in U.S. Patent Application Publication No. 2016/0002298, the disclosure of which is incorporated herein by reference in its entirety.

In some embodiments, the cytotoxin is an amatoxin or derivative thereof, and the amatoxin-linker conjugate is represented by formula IIIA, wherein:
$R_1$ and $R_2$ are each independently H or OH;
$R_3$ is $R_C$;
$R_4$, $R_6$, and $R_7$ are each H;
$R_5$ is H, OH, or $OC_1$-$C_6$ alkyl;
$R_8$ is OH or $NH_2$;
$R_9$ is H or OH;
Q is —S—, —S(O)—, or —$SO_2$—; and
wherein $R_C$ and $R_D$ are as defined above. Such amatoxin-linker conjugates are described, for example, in U.S. Patent Application Publication No. 2014/0294865, the disclosure of which is incorporated herein by reference in its entirety.

In some embodiments, the cytotoxin is an amatoxin or derivative thereof and the amatoxin-linker conjugate is represented by formula IIIA, wherein:
$R_1$ and $R_2$ are each independently H or OH;
$R_3$, $R_6$, and $R_7$ are each H;
$R_4$ and $R_5$ are each independently H, OH, $OR_C$, or $R_C$;
$R_8$ is OH or $NH_2$;
$R_9$ is H or OH;
Q is —S—, —S(O)—, or —$SO_2$—; and
wherein $R_C$ and $R_D$ are as defined above. Such amatoxin-linker conjugates are described, for example, in U.S. Patent Application Publication No. 2015/0218220, the disclosure of which is incorporated herein by reference in its entirety.

In some embodiments, the cytotoxin is an amatoxin or derivative thereof and the amatoxin-linker conjugate is represented by formula IIIA, wherein:
$R_1$ and $R_2$ are each independently H or OH;
$R_3$, $R_6$, and $R_7$ are each H;
$R_4$ and $R_5$ are each independently H or OH;
$R_8$ is OH, $NH_2$, $OR_C$, or $NHR_C$;
$R_9$ is H or OH;
Q is —S—, —S(O)—, or —$SO_2$—; and
wherein $R_C$ and $R_D$ are as defined above. Such amatoxin-linker conjugates are described, for example, in U.S. Pat. Nos. 9,233,173 and 9,399,681, the disclosures of each of which are incorporated herein by reference in their entirety.

In some embodiments, the cytotoxin is an amatoxin or derivative thereof and the amatoxin-linker conjugate is represented by formula IIIB:

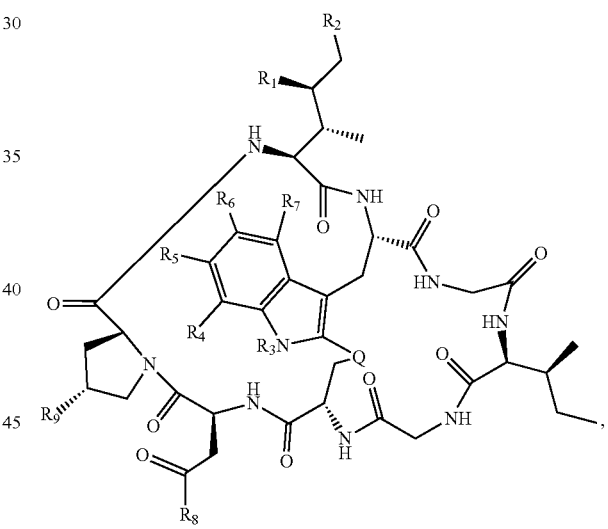

(IIIB)

wherein:
$R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form a 5-membered heterocycloalkyl group;
$R_3$ is H, $R_C$, or $R_D$;
each of $R_4$, $R_5$, $R_6$, and $R_7$ is independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
Q is —S—, —S(O)—, or —$SO_2$—;
$R_C$ is -L-Z' or -L-Z-Ab, wherein L is a linker, and is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl; or comprises a dipeptide; or —(($CH_2$)$_m$O)$_n$($CH_2$)$_m$—, where m and n are each independently selected from 1, 2, 3, 4, 5, 6, 7, 8, 9, and 10; Z' is a reactive moiety, and Z is a chemical moiety resulting from a coupling reaction of Z' with a functional group on Ab; and $R_D$ is $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, heteroaryl, or a combination thereof, wherein each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, or heteroaryl is optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

Formula (IIIA) includes an amatoxin and a linker and, in some embodiments, a linker, a chemical moiety, and an antibody.

In some embodiments, $R_A$ and $R_B$, together with the oxygen atoms to which they are bound, combine to form a 5-membered heterocycloalkyl of formula:

wherein Y is —(C═O)—, —(C═S)—, —(C═$NR_E$)—, or —($CR_E R_{E'}$)—; and wherein $R_E$ and $R_{E'}$ are each independently H, $C_1$-$C_6$ alkylene-$R_C$, $C_1$-$C_6$ heteroalkylene-$R_C$, $C_2$-$C_6$ alkenylene-$R_C$, $C_2$-$C_6$ heteroalkenylene-$R_C$, $C_2$-$C_6$ alkynylene-$R_C$, $C_2$-$C_6$ heteroalkynylene-$R_C$, cycloalkylene-$R_C$, heterocycloalkylene-$R_C$, arylene-$R_C$, or heteroarylene-$R_C$, or a combination thereof, wherein each $C_1$-$C_6$ alkylene-$R_C$, $C_1$-$C_6$ heteroalkylene-$R_C$, $C_2$-$C_6$ alkenylene-$R_C$, $C_2$-$C_6$ heteroalkenylene-$R_C$, $C_2$-$C_6$ alkynylene-$R_C$, $C_2$-$C_6$ heteroalkynylene-$R_C$, cycloalkylene-$R_C$, heterocycloalkylene-$R_C$, arylene-$R_C$, or heteroarylene-$R_C$ is optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, the antibodies or antigen-binding fragments thereof as described herein are conjugated to an amatoxin-linker conjugate, or derivative thereof, represented by formula IIIB, wherein $R_1$ is H, OH, $OR_A$, or $OR_C$;
$R_2$ is H, OH, $OR_B$, or $OR_C$;

$R_A$ and $R_B$, when present, together with the oxygen atoms to which they are bound, combine to form a 5-membered heterocycloalkyl of formula:

wherein $R_3$ is H or $R_C$.

In some embodiments, the cytotoxin is an amatoxin or derivative thereof, and the amatoxin-linker conjugate is represented by formula IIIB, wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form a 5-membered heterocycloalkyl group of formula:

wherein
$R_3$ is H or $R_C$;
$R_4$ and $R_5$ are each independently H, OH, $OR_C$, $R_C$, or $OR_D$;
$R_6$ and $R_7$ are each H;
$R_8$ is OH, $NH_2$, $OR_C$, or $NHR_C$;
$R_9$ is H or OH; and
wherein $R_C$ and $R_D$ are as defined above.

In some embodiments, the cytotoxin is an amatoxin or derivative thereof, and the amatoxin-linker conjugate is represented by formula IIIB, wherein:

$R_1$ is H, OH, or $OR_A$;
$R_2$ is H, OH, or $OR_B$;
$R_A$ and $R_B$, when present, together with the oxygen atoms to which they are bound, combine to form a 5-membered heterocycloalkyl group of formula:

wherein
$R_3$, $R_4$, $R_6$, and $R_7$ are each H;
$R_5$ is $OR_C$;
$R_8$ is OH or $NH_2$;
$R_9$ is H or OH;
Q is —S—, —S(O)—, or —$SO_2$—; and
wherein $R_C$ and $R_D$ are as defined above. Such amatoxin-linker conjugates are described, for example, in U.S. Patent Application Publication No. 2016/0002298, the disclosure of which is incorporated herein by reference in its entirety.

In some embodiments, the cytotoxin is an amatoxin or derivative thereof, and the amatoxin-linker conjugate is represented by formula IIIB, wherein:

$R_1$ and $R_2$ are each independently H or OH;
$R_3$ is $R_C$;
$R_4$, $R_6$, and $R_7$ are each H;
$R_5$ is H, OH, or $OC_1$-$C_6$ alkyl;
$R_8$ is OH or $NH_2$;
$R_9$ is H or OH;
Q is —S—, —S(O)—, or —$SO_2$—; and
wherein $R_C$ and $R_D$ are as defined above. Such amatoxin-linker conjugates are described, for example, in U.S. Patent Application Publication No. 2014/0294865, the disclosure of which is incorporated herein by reference in its entirety.

In some embodiments, the cytotoxin is an amatoxin or derivative thereof, and the amatoxin-linker conjugate is represented by formula IIIB, wherein:

$R_1$ and $R_2$ are each independently H or OH;
$R_3$, $R_6$, and $R_7$ are each H;
$R_4$ and $R_5$ are each independently H, OH, $OR_C$, or $R_C$;
$R_8$ is OH or $NH_2$;
$R_9$ is H or OH;
Q is —S—, —S(O)—, or —$SO_2$—; and
wherein $R_C$ and $R_D$ are as defined above. Such amatoxin-linker conjugates are described, for example, in U.S. Patent Application Publication No. 2015/0218220, the disclosure of which is incorporated herein by reference in its entirety.

In some embodiments, the cytotoxin is an amatoxin or derivative thereof, and the amatoxin-linker conjugate is represented by formula IIIB, wherein:

$R_1$ and $R_2$ are each independently H or OH;
$R_3$, $R_6$, and $R_7$ are each H;
$R_4$ and $R_5$ are each independently H or OH;
$R_8$ is OH, $NH_2$, $OR_C$, or $NHR_C$;
$R_9$ is H or OH;
Q is —S—, —S(O)—, or —$SO_2$—; and
wherein $R_C$ and $R_D$ are as defined above. Such amatoxin-linker conjugates are described, for example, in U.S. Pat. Nos. 9,233,173 and 9,399,681, the disclosures of each of which are incorporated herein by reference in their entirety.

Auristatins

Anti-CD5 antibodies and antigen-binding fragments thereof described herein can be conjugated to a cytotoxin that is an auristatin (U.S. Pat. Nos. 5,635,483; 5,780,588). Auristatins are anti-mitotic agents that interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965).

(U.S. Pat. Nos. 5,635,483; 5,780,588). The auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF (MMAE and MMAF, respectively), disclosed in Senter et al, Proceedings of the American Association for Cancer Research, Volume 45, Abstract Number 623, presented Mar. 28, 2004, the disclosure of which is expressly incorporated by reference in its entirety.

An exemplary auristatin embodiment is MMAE:

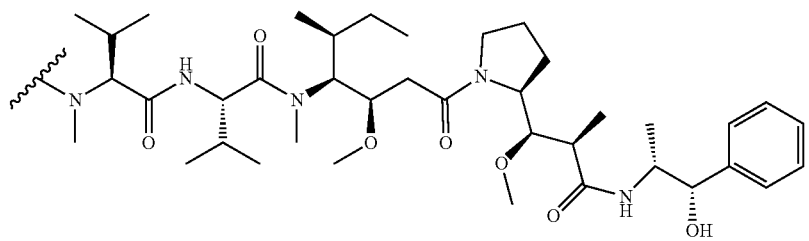 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

wherein the wavy line indicates the point of covalent attachment to the linker of an antibody-drug or drug-linker conjugate (-L-Z-Ab or -L-Z', as described herein).

Another exemplary auristatin embodiment is MMAF,

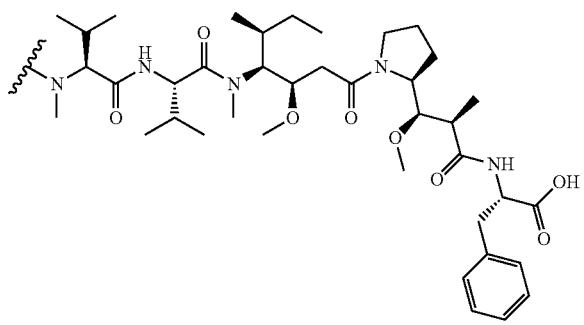 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

wherein the wavy line indicates the point of covalent attachment to the linker of an antibody-linker conjugate (-L-Z-Ab or -L-Z', as described herein), as disclosed in US 2005/0238649:

Auristatins may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 15:859-863; and Doronina (2003) Nat. Biotechnol. 21(7):778-784.

Maytansinoids

Antibodies and antigen-binding fragments thereof described herein can be conjugated to a cytotoxin that is a microtubule binding agent. In some embodiments, the microtubule binding agent is a maytansine, a maytansinoid or a maytansinoid analog. Maytansinoids are mitototic inhibitors which bind microtubules and act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Examples of suitable maytansinoids include esters of maytansinol, synthetic maytansinol, and maytansinol analogs and derivatives. Included herein are any cytotoxins that inhibit microtubule formation and that are highly toxic to mammalian cells, as are maytansinoids, maytansinol, and maytansinol analogs, and derivatives.

Examples of suitable maytansinol esters include those having a modified aromatic ring and those having modifications at other positions. Such suitable maytansinoids are disclosed in U.S. Pat. Nos. 4,137,230; 4,151,042; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,424,219; 4,450,254; 4,322,348; 4,362,663; 4,371,533; 5,208,020; 5,416,064; 5,475,092; 5,585,499; 5,846,545; 6,333,410; 7,276,497; and 7,473,796, the disclosures of each of which are incorporated herein by reference as they pertain to maytansinoids and derivatives thereof.

In some embodiments, the antibody-drug conjugates (ADCs) of the present disclosure utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula IV:

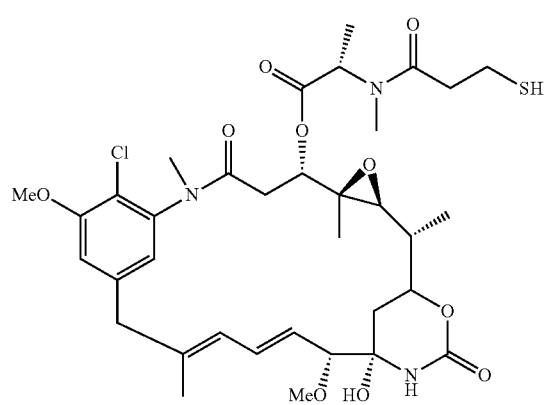

(IV)

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula V:

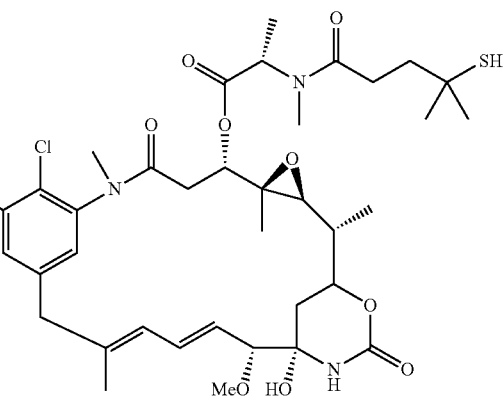

(V)

Another maytansinoid comprising a side chain that contains a sterically hindered thiol bond is $N^{2'}$-deacetyl-$N^{2'}$(4-mercapto-1-oxopentyl)-maytansine (termed DM3), represented by the following structural formula VI:

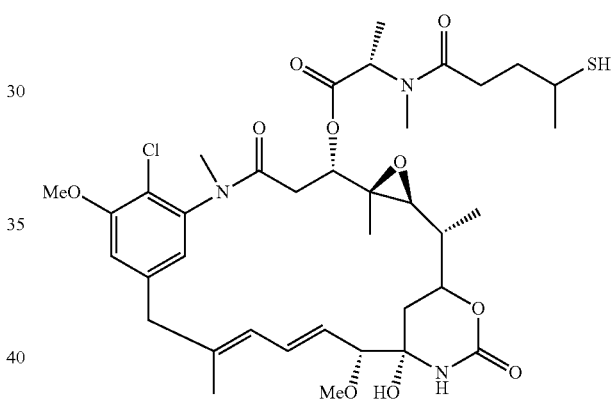

(VI)

Each of the maytansinoids taught in U.S. Pat. Nos. 5,208,020 and 7,276,497, can also be used in the conjugates of the present disclosure. In this regard, the entire disclosure of U.S. Pat. Nos. 5,208,020 and 7,276,697 is incorporated herein by reference.

Many positions on maytansinoids can serve as the position to covalently bond the linking moiety and, hence the antibodies or antigen-binding fragments thereof (-L-Z-Ab or -L-Z', as described herein). For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to covalently bond the linker moiety, and in some particular embodiments, the C-3 position of maytansinol serves as the position to covalently bond the linking moiety. There are many linking groups known in the art for making antibody-maytansinoid conjugates, including, for example, those disclosed in U.S. Pat. Nos. 5,208,020, 6,441,163, and EP Patent No. 0425235 B1; Chari et al., Cancer Research 52:127-131 (1992); and U.S. 2005/0169933 A1, the disclosures of which are hereby expressly incorporated by reference. Additional linking groups are described and exemplified herein.

The present invention also includes various isomers and mixtures of maytansinoids and conjugates. Certain compounds and conjugates of the present invention may exist in various stereoisomeric, enantiomeric, and diastereomeric forms. Several descriptions for producing such antibody-maytansinoid conjugates are provided in U.S. Pat. Nos. 5,208,020; 5,416,064; 6,333,410; 6,441,163; 6,716,821; and 7,368,565, each of which is incorporated herein in its entirety.

Anthracyclines

In other embodiments, the antibodies and antigen-binding fragments thereof described herein can be conjugated to a cytotoxin that is an anthracycline molecule. Anthracyclines are antibiotic compounds that exhibit cytotoxic activity. Studies have indicated that anthracyclines may operate to kill cells by a number of different mechanisms including: 1) intercalation of the drug molecules into the DNA of the cell thereby inhibiting DNA-dependent nucleic acid synthesis; 2) production by the drug of free radicals which then react with cellular macromolecules to cause damage to the cells or 3) interactions of the drug molecules with the cell membrane [see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102]. Because of their cytotoxic potential anthracyclines have been used in the treatment of numerous cancers such as leukemia, breast carcinoma, lung carcinoma, ovarian adenocarcinoma and sarcomas [see e.g., P. H-Wiernik, in *Anthracycline: Current Status And New Developments* p 11]. Commonly used anthracyclines include doxorubicin, epirubicin, idarubicin and daunomycin.

Representative examples of anthracyclines include, but are not limited to daunorubicin (Cerubidine; Bedford Laboratories), doxorubicin (Adriamycin; Bedford Laboratories; also referred to as doxorubicin hydrochloride, hydroxydaunorubicin, and Rubex), epirubicin (Ellence; Pfizer), and idarubicin (Idamycin; Pfizer Inc.) The anthracycline analog, doxorubicin (ADRIAMYCINO) is thought to interact with DNA by intercalation and inhibition of the progression of the enzyme topoisomerase II, which unwinds DNA for transcription. Doxorubicin stabilizes the topoisomerase II complex after it has broken the DNA chain for replication, preventing the DNA double helix from being resealed and thereby stopping the process of replication. Doxorubicin and daunorubicin (DAUNOMYCIN) are prototype cytotoxic natural product anthracycline chemotherapeutics (Sessa et al., (2007) Cardiovasc. Toxicol. 7:75-79).

One non-limiting example of a suitable anthracycline for use herein is PNU-159682 ("PNU"), a highly potent major metabolite of nemorubicin. PNU exhibits greater than 3000-fold cytotoxicity relative to the parent nemorubicin (Quintieri et al., Clinical Cancer Research 2005, 11, 1608-1617). PNU is represented by the structural formula:

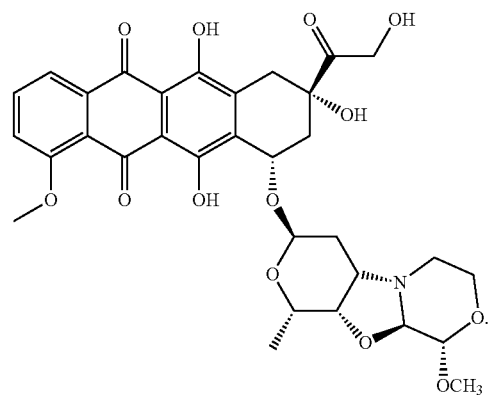

Multiple positions on anthracyclines such as PNU can serve as the position to covalently bond the linking moiety and, hence the anti-CD137 antibodies or antigen-binding fragments thereof as described herein. For example, linkers may be introduced through modifications to the hydroxymethyl ketone side chain.

In some embodiments, the cytotoxin is a PNU derivative represented by the structural formula:

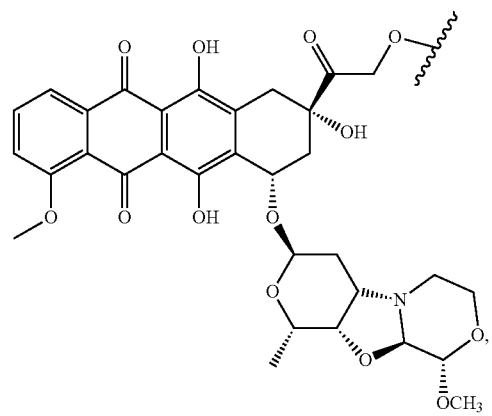

wherein the wavy line indicates the point of covalent attachment to the linker of the ADC as described herein.

In some embodiments, the cytotoxin is a PNU derivative represented by the structural formula:

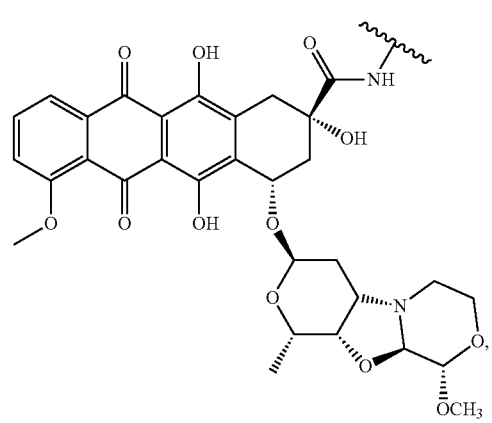

wherein the wavy line indicates the point of covalent attachment to the linker of the ADC as described herein.

Pyrrolobenzodiazepines (PBDs) In other embodiments, the anti-CD5 antibodies or antigen-binding fragments thereof described herein can be conjugated to a cytotoxin that is a pyrrolobenzodiazepine (PBD) or a cytotoxin that comprises a PBD. PBDs may be produced by certain actinomycetes and have been shown to be sequence selective DNA alkylating compounds. PBD cytotoxins include, but are not limited to, anthramycin, dimeric PBDs, and those disclosed in, for example, Hartley, J A (2011) The development of pyrrolobenzodiazepines as antitumour agents. Expert Opin Inv Drug, 20(6), 733-744 and Antonow D, Thurston D E (2011) Synthesis of DNA-interactive pyrrolo[2,1-c][1,4] benzodiazepines (PBDs). Chem Rev 111: 2815-2864.

In some embodiments, the cytotoxin may be a pyrrolobenzodiazepine dimer represented by the structural formula:

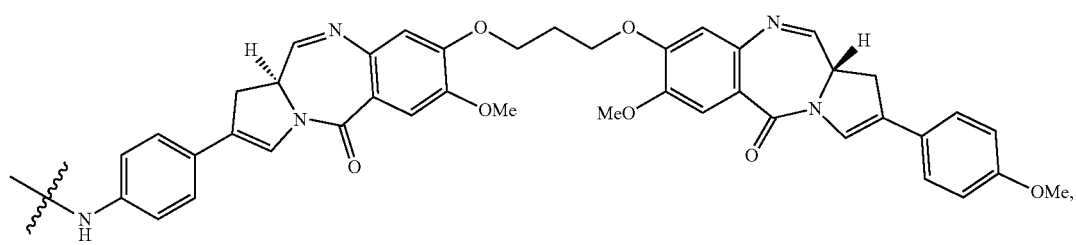 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

wherein the wavy line indicates the point of covalent attachment to the linker of the ADC as described herein. ADCs based on this PBD are disclosed in, for example, Sutherland et al., Blood 2013 122:1455-1463, which is incorporated by reference herein in its entirety.

In some embodiments, the cytotoxin may be a PBD dimer represented by the structural formula:

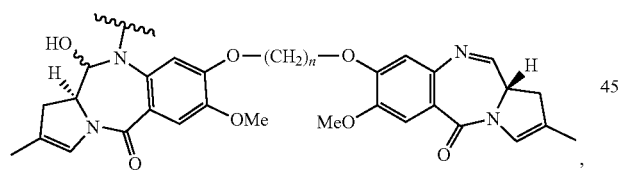

wherein n is 3 or 5, and wherein the wavy line indicates the point of covalent attachment to the linker of the ADC as described herein.

In some embodiments, the cytotoxin may be a PBD dimer represented by the structural formula:

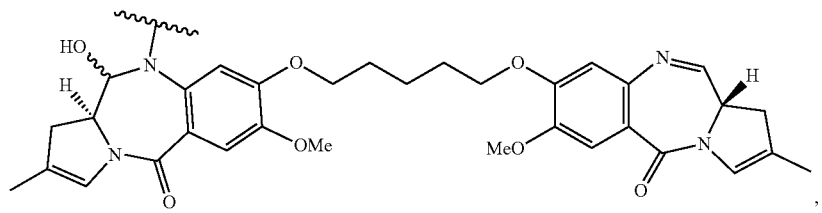

wherein the wavy line indicates the point of covalent attachment to the linker of the ADC as described herein.

In a specific embodiment, the cytotoxin may be a PBD dimer, which, when taken together with a linker and a reactive moiety Z', each as described herein, may be represented by the structure:

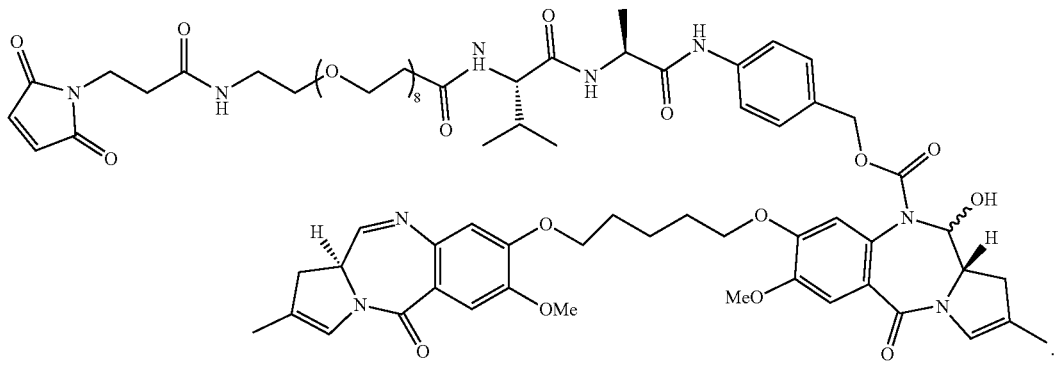

This particular cytotoxin-linker conjugate is known as tesirine (SG3249), and has been described in, for example, Howard et al., ACS Med. Chem. Lett. 2016, 7(11), 983-987, the disclosure of which is incorporated by reference herein in its entirety.

In a specific embodiment, the cytotoxin may be a PBD dimer, which, when taken together with a linker and a reactive moiety Z', each as described herein, may be represented by the structure:

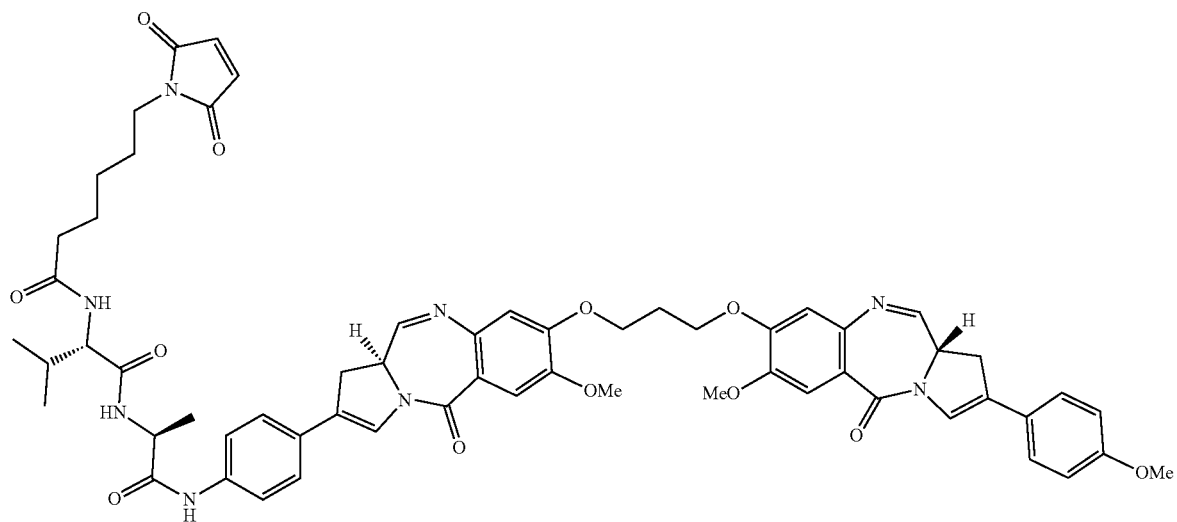 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@H]5C=N6)cc4N=C[C@@H]3C2)cc1]

This particular cytotoxin-linker conjugate is known as talirine, and has been described, for example, in Mantaj et al., Angewandte Chemie International Edition English 2017, 56, 462-488, the disclosure of which is incorporated by reference herein in its entirety.

Calicheamicin

In other embodiments, the antibodies and antigen-binding fragments thereof described herein can be conjugated to a cytotoxin that is an enediyne antitumor antibiotic (e.g., calicheamicins, ozogamicin). The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents to American Cyanamid. Examples of calicheamicins suitable for use in the present invention are disclosed, for example, in U.S. Pat. Nos. 4,671,958; 4,970,198, 5,053,394, 5,037,651; and 5,079,233, which are incorporated herein in their entirety.

An exemplary calicheamicin is designated $\gamma_1$, which is herein referenced simply as gamma, and has the structural formula:

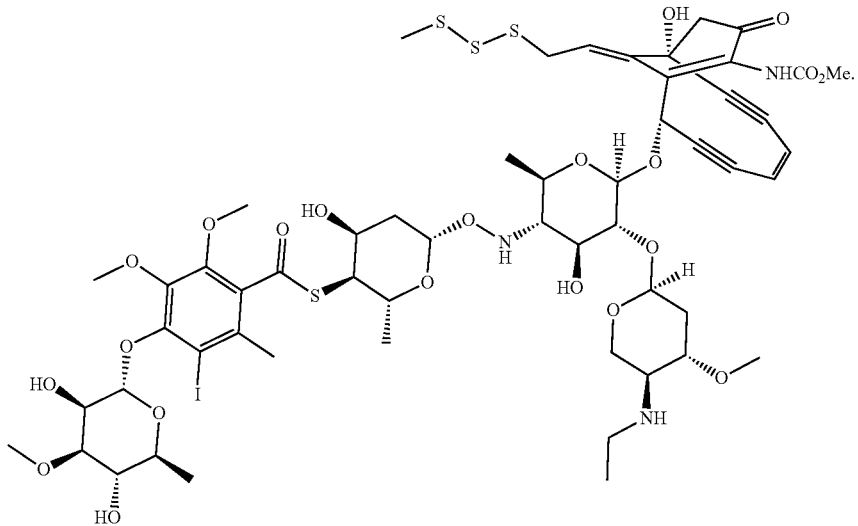

In some embodiments, the calicheamicin is a gamma-calicheamicin derivative or an N-acetyl gamma-calicheamicin derivative. Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents. Calicheamicins contain a methyltrisulfide moiety that can be reacted with appropriate thiols to form disulfides, at the same time introducing a functional group that is useful in attaching a calicheamicin derivative to an anti-CD5 antibody or antigen-binding fragment thereof as described herein, via a linker.

In one embodiment, the cytotoxin of the ADC as disclosed herein is a calicheamicin disulfide derivative represented by the formula:

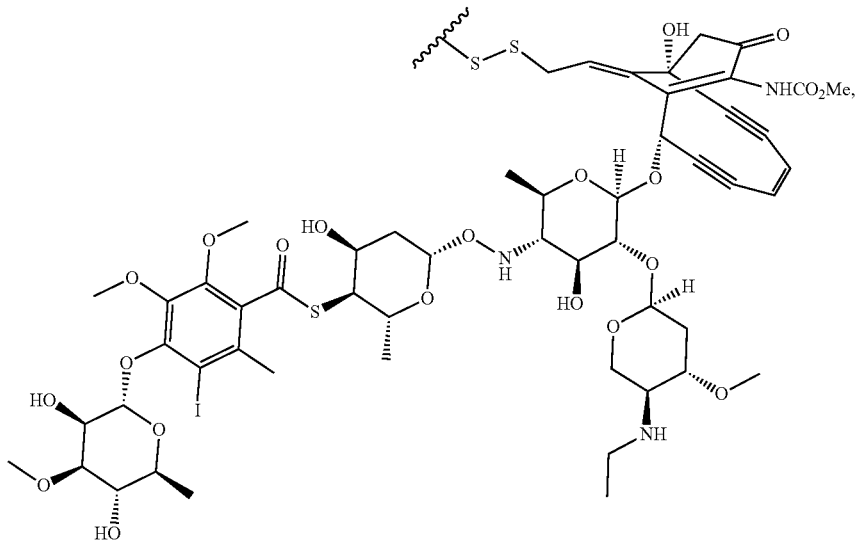

wherein the wavy line indicates the attachment point of the linker.

Additional Cytotoxins

In other embodiments, the antibodies and antigen-binding fragments thereof described herein can be conjugated to a cytotoxin other than or in addition to those cytotoxins disclosed herein above. Additional cytotoxins suitable for use with the compositions and methods described herein include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, antidorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, episteride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, rnerbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

Linkers

The term "Linker" as used herein means a divalent chemical moiety comprising a covalent bond or a chain of atoms that covalently attaches an anti-CD5 antibody or fragment thereof (Ab) to a drug moiety (D) to form antibody-drug conjugates (ADC) of formula I. Suitable linkers have two reactive termini, one for conjugation to an antibody and the other for conjugation to a cytotoxin. The antibody conjugation reactive terminus of the linker (reactive moiety, Z') is typically a site that is capable of conjugation to the antibody through a cysteine thiol or lysine amine group on the antibody, and so is typically a thiol-reactive group such as a double bond (as in maleimide) or a leaving group such as a chloro, bromo, iodo, or an R-sulfanyl group, or an amine-reactive group such as a carboxyl group; while the cytotoxin conjugation reactive terminus of the linker is typically a site that is capable of conjugation to the cytotoxin. Non-limiting examples for linker-cytotoxin conjugation include, for example, formation of an amide bond with a basic amine or carboxyl group on the cytotoxin, via a carboxyl or basic amine group on the linker, respectively, or formation of an ether or the like, via alkylation of an OH group on the cytotoxin, via e.g., a leaving group on the linker. In some embodiments, cytotoxin-linker conjugation is through formation of an amide bond with a basic amine or carboxyl group on the cytotoxin, and so the reactive substituent on the linker is respectively a carboxyl or basic amine group. When the term "linker" is used in describing the linker in conjugated form, one or both of the reactive termini will be absent (such as reactive moiety Z', having been converted to chemical moiety Z) or incomplete (such as being only the carbonyl of the carboxylic acid) because of the formation of the bonds between the linker and/or the cytotoxin, and between the linker and/or the antibody or antigen-binding fragment thereof. Such conjugation reactions are described further herein below.

A variety of linkers can be used to conjugate the antibodies, antigen-binding fragments, and ligands described to a cytotoxic molecule. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation. The linkers useful for the present ADCs are preferably stable extracellularly, prevent aggregation of ADC molecules and keep the ADC freely soluble in aqueous media and in a monomeric state. Before transport or delivery into a cell, the ADC is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the cytotoxic moiety. Stability of the ADC may be measured by standard analytical techniques such as mass spectroscopy, HPLC, and the separation/analysis technique LC/MS. Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Suitable cleavable linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation). Suitable cleavable linkers may include, for example, chemical moieties such as a hydrazine, a disulfide, a thioether or a dipeptide.

Linkers hydrolyzable under acidic conditions include, for example, hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are relatively stable under neutral pH conditions, such as those in the blood, but are unstable at below pH 5.5 or 5.0, the approximate pH of the lysosome.

Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety as it pertains to linkers suitable for covalent conjugation.

Linkers susceptible to enzymatic hydrolysis can be, e.g., a peptide-containing linker that is cleaved by an intracellular peptidase or protease enzyme, including, but not limited to, a lysosomal or endosomal protease. One advantage of using intracellular proteolytic release of the therapeutic agent is that the agent is typically attenuated when conjugated and the serum stabilities of the conjugates are typically high. In some embodiments, the peptidyl linker is at least two amino acids long or at least three amino acids long. Exemplary amino acid linkers include a dipeptide, a tripeptide, a tetrapeptide or a pentapeptide. Examples of suitable peptides include those containing amino acids such as Valine, Alanine, Citrulline (Cit), Phenylalanine, Lysine, Leucine, and Glycine. Amino acid residues which comprise an amino acid linker component include those occurring naturally, as well as minor amino acids and non-naturally occurring amino acid analogs, such as citrulline. Exemplary dipeptides include valine-citrulline (vc or val-cit) and alanine-phenylalanine (af or ala-phe). Exemplary tripeptides include glycine-valine-citrulline (gly-val-cit) and glycine-glycine-glycine (gly-gly-gly). In some embodiments, the linker includes a dipeptide such as Val-Cit, Ala-Val, or Phe-Lys, Val-Lys, Ala-Lys, Phe-Cit, Leu-Cit, Ile-Cit, Phe-Arg, or Trp-Cit. Linkers containing dipeptides such as Val-Cit or Phe-Lys are disclosed in, for example, U.S. Pat. No. 6,214,345, the disclosure of which is incorporated herein by reference in its entirety as it pertains to linkers suitable for covalent conjugation. In some embodiments, the linker includes a dipeptide selected from Val-Ala and Val-Cit.

Linkers suitable for conjugating the antibodies, antigen-binding fragments, and ligands described herein to a cytotoxic molecule include those capable of releasing a cytotoxin by a 1,6-elimination process. Chemical moieties capable of this elimination process include the p-aminobenzyl (PAB) group, 6-maleimidohexanoic acid, pH-sensitive carbonates, and other reagents as described in Jain et al., Pharm. Res. 32:3526-3540, 2015, the disclosure of which is incorporated herein by reference in its entirety as it pertains to linkers suitable for covalent conjugation.

In some embodiments, the linker includes a "self-immolative" group such as the aforementioned PAB or PABC (para-aminobenzyloxycarbonyl), which are disclosed in, for example, Carl et al., J. Med. Chem. (1981) 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other such chemical moieties capable of this process ("self-immolative linkers") include methylene carbamates and heteroaryl groups such as aminothiazoles, aminoimidazoles, aminopyrimidines, and the like. Linkers containing such heterocyclic self-immolative groups are disclosed in, for example, U.S. Patent Publication Nos. 20160303254 and 20150079114, and U.S. Pat. No. 7,754,681; Hay et al. (1999) Bioorg. Med. Chem. Lett. 9:2237; US 2005/0256030; de Groot et al (2001) J. Org. Chem. 66:8815-8830; and U.S. Pat. No. 7,223,837. In some embodiments, a dipeptide is used in combination with a self-immolative linker.

Linkers suitable for use herein further may include one or more groups selected from $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, and combinations thereof, each of which may be optionally substituted. Non-limiting examples of such groups include $(CH_2)_p$, $(CH_2CH_2O)_p$, and $-(C=O)(CH_2)_p-$ units, wherein p is an integer from 1-6, independently selected for each occasion.

In some embodiments, each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may optionally be interrupted by one or more heteroatoms selected from O, S and N.

In some embodiments, each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may optionally be interrupted by one or more heteroatoms selected from O, S and N and may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro. Suitable linkers may contain groups having solubility enhancing properties. Linkers including the $(CH_2CH_2O)_p$ unit (polyethylene glycol, PEG), for example, can enhance solubility, as can alkyl chains substituted with amino, sulfonic acid, phosphonic acid or phosphoric acid residues. Linkers including such moieties are disclosed in, for example, U.S. Pat. Nos. 8,236,319 and 9,504,756, the disclosure of each of which is incorporated herein by reference in its entirety as it pertains to linkers suitable for covalent conjugation. Further solubility enhancing groups include, for example, acyl and carbamoyl sulfamide groups, having the structure:

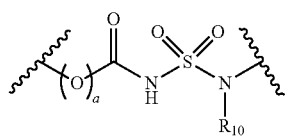

wherein a is 0 or 1; and $R^{10}$ is selected from the group consisting of hydrogen, $C_1$-$C_{24}$ alkyl groups, $C_3$-$C_{24}$ cycloalkyl groups, $C_1$-$C_{24}$ (hetero)aryl groups, $C_1$-$C_{24}$ alkyl(hetero)aryl groups and $C_1$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted and/or optionally interrupted by one or more heteroatoms selected from O, S and $NR^{11}R^{12}$, wherein $R^{11}$ and $R^{12}$ are independently selected from the group consisting of hydrogen and $C_1$-$C_4$ alkyl groups; or $R^{10}$ is a cytotoxin, wherein the cytotoxin is optionally connected to N via a spacer moiety. Linkers containing such groups are described, for example, in U.S. Pat. No. 9,636,421 and U.S. Patent Application Publication No. 2017/0298145, the disclosures of which are incorporated herein by reference in their entirety as they pertain to linkers suitable for covalent conjugation to cytotoxins and antibodies or antigen-binding fragments thereof.

In some embodiments, the linker may include one or more of a hydrazine, a disulfide, a thioether, a dipeptide, a p-aminobenzyl (PAB) group, a heterocyclic self-immolative group, an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted $C_2$-$C_6$ alkynyl, an optionally substituted $C_2$-$C_6$ heteroalkynyl, an optionally substituted $C_3$-$C_6$ cycloalkyl, an optionally substituted heterocycloalkyl, an optionally substituted aryl, an optionally substituted heteroaryl, a solubility enhancing group, acyl, —(C=O)—, or —$(CH_2CH_2O)_p$— group, wherein p is an integer from 1-6. One of skill in the art will recognize that one or more of the groups listed may be present in the form of a bivalent (diradical) species, e.g., $C_1$-$C_6$ alkylene and the like.

In some embodiments, the linker includes a p-aminobenzyl group (PAB). In one embodiment, the p-aminobenzyl group is disposed between the cytotoxic drug and a protease cleavage site in the linker. In one embodiment, the p-aminobenzyl group is part of a p-aminobenzyloxycarbonyl unit. In one embodiment, the p-aminobenzyl group is part of a p-aminobenzylamido unit.

In some embodiments, the linker comprises a dipeptide selected from the group consisting of Phe-Lys, Val-Lys, Phe-Ala, Phe-Cit, Val-Ala, Val-Cit, and Val-Arg. In some embodiments, the linker comprises one or more of PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a combination of one or more of a peptide, oligosaccharide, —$(CH_2)_p$—, —$(CH_2CH_2O)_p$—, PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a —(C=O) $(CH_2)_p$— unit, wherein p is an integer from 1-6.

In some embodiments, the linker comprises a —$(CH)_{2n}$— unit, where n is an integer from 2-6. In some embodiments, the linker includes —$((CH_2)_n$ where n is 6. In some embodiments, L-Z is

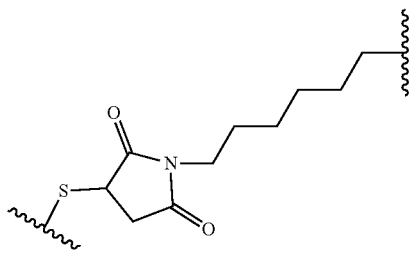

where S is a sulfur atom which represents the reactive substituent present within an antibody, or antigen-binding fragment thereof, that binds CD5 (e.g., from the —SH group of a cysteine residue).

In some embodiments, the linker comprises a $((CH_2)_m O)_n(CH_2)_m$— group where n and m are each independently selected from 1, 2, 3, 4, 5, 6, 7, 8, 9, and 10; and a heteroaryl group, wherein the heteroaryl group is a triazole. In some embodiments, the $((CH_2)_m O)_n(CH_2)_m$— group and triazole together comprise

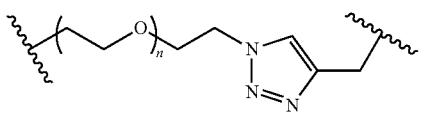

where n is from 1 to 10, and the wavy lines indicate attachment points to additional linker components, the chemical moiety Z, or the amatoxin. Other linkers that may used in the methods and compositions described herein are described in US 2019/0144504, which is incorporated by reference herein.

In one specific embodiment, the linker comprises PAB-Ala-Val-propionyl, represented by the structure

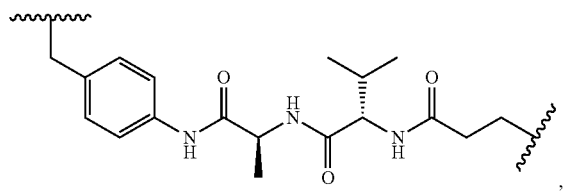 [SMILES: *CCC(=O)N[C@H](C(=O)N[C@@H](C)C(=O)Nc1ccc(C*)cc1)C(C)C]

, wherein the wavy lines indicate attachment points to the cytotoxin and the reactive moiety Z'.

In another specific embodiment, the linker comprises PAB-Cit-Val-propionyl, represented by the structure

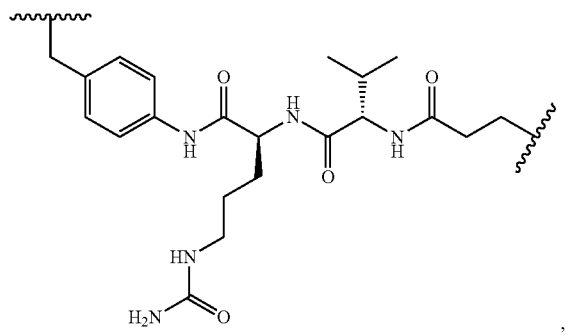 [SMILES: *CCC(=O)N[C@H](C(=O)N[C@@H](CCCNC(N)=O)C(=O)Nc1ccc(C*)cc1)C(C)C]

, wherein the wavy lines indicate attachment points to the cytotoxin and the reactive moiety Z'. Such PAB-dipeptide-propionyl linkers are disclosed in, e.g., Patent Application Publication No. WO2017/149077, which is incorporated by reference herein in its entirety. Further, the cytotoxins disclosed in WO2017/149077 are incorporated by reference herein.

It will be recognized by one of skill in the art that any one or more of the chemical groups, moieties and features disclosed herein may be combined in multiple ways to form linkers useful for conjugation of the antibodies and cytotoxins as disclosed herein. Further linkers useful in conjunction with the compositions and methods described herein, are described, for example, in U.S. Patent Application Publication No. 2015/0218220, the disclosure of which is incorporated herein by reference in its entirety.

In certain embodiments, an intermediate, which is the precursor of the linker, is reacted with the drug moiety under appropriate conditions. In certain embodiments, reactive groups are used on the drug and/or the intermediate or linker. The product of the reaction between the drug and the intermediate, or the derivatized drug, is subsequently reacted with the antibody or antigen-binding fragment under appropriate conditions. Alternatively, the linker or intermediate may first be reacted with the antibody or a derivatized antibody, and then reacted with the drug or derivatized drug. Such conjugation reactions will now be described more fully.

A number of different reactions are available for covalent attachment of linkers or drug-linker conjugates to the antibody or antigen-binding fragment thereof. Suitable attachment points on the antibody molecule include the amine groups of lysine, the free carboxylic acid groups of glutamic acid and aspartic acid, the sulfhydryl groups of cysteine, and the various moieties of the aromatic amino acids. For instance, non-specific covalent attachment may be undertaken using a carbodiimide reaction to link a carboxy (or amino) group on a compound to an amino (or carboxy) group on an antibody moiety. Additionally, bifunctional agents such as dialdehydes or imidoesters may also be used to link the amino group on a compound to an amino group on an antibody moiety. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates may also be used as coupling agents for covalently attaching drugs to binding agents. Other techniques are known to the skilled artisan and within the scope of the present disclosure.

Linkers useful in for conjugation to the antibodies or antigen-binding fragments as described herein include, without limitation, linkers containing chemical moieties Z formed by coupling reactions as depicted in Table 3, below. Curved lines designate points of attachment to the antibody or antigen-binding fragment, and the cytotoxic molecule, respectively.

TABLE 3

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition | |
| [3 + 2] Cycloaddition | |

TABLE 3-continued

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition, Esterification | 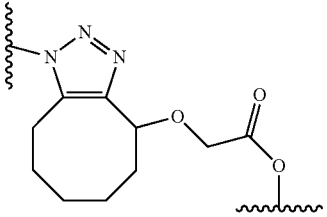 [SMILES: *OC(=O)COC1CCCCCc2c1nnn2*] |
| [3 + 2] Cycloaddition, Esterification | 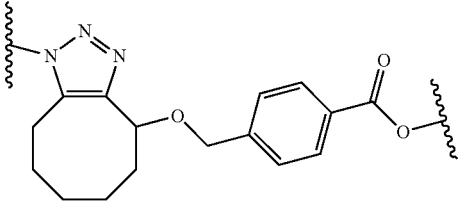 [SMILES: *OC(=O)c1ccc(COC2CCCCCc3c2nnn3*)cc1] |
| [3 + 2] Cycloaddition, Esterification | 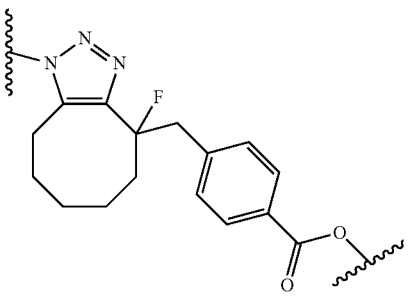 [SMILES: *OC(=O)c1ccc(CC2(F)CCCCCc3c2nnn3*)cc1] |
| [3 + 2] Cycloaddition, Esterification | 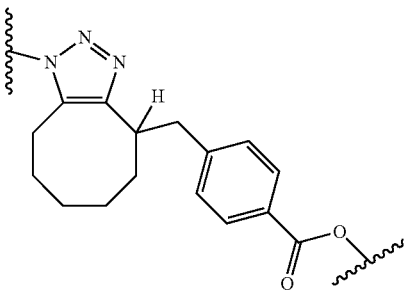 [SMILES: *OC(=O)c1ccc(CC2CCCCCc3c2nnn3*)cc1] |
| [3 + 2] Cycloaddition, Esterification | 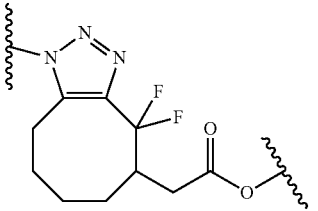 [SMILES: *OC(=O)CC1CCCCc2c(nnn2*)C1(F)F] |
| [3 + 2] Cycloaddition, Esterification | 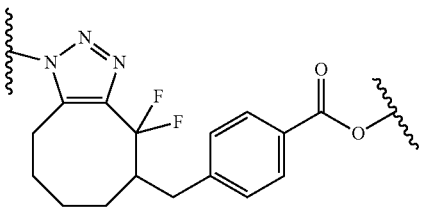 [SMILES: *OC(=O)c1ccc(CC2CCCCc3c(nnn3*)C2(F)F)cc1] |

TABLE 3-continued
Exemplary chemical moieties Z formed by coupling reactions in the formation of antibody-drug conjugates
| Exemplary Coupling Reactions | Chemical Moiety Z Formed by Coupling Reactions |
|---|---|
| [3 + 2] Cycloaddition, Esterification | 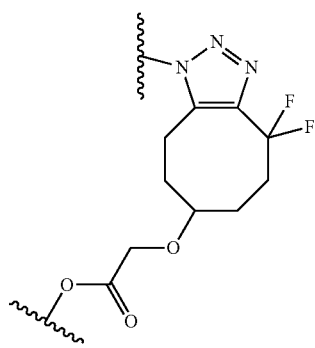 [SMILES: *OC(=O)COC1CCc2c(nnn2*)C(F)(F)CC1] |
| [3 + 2] Cycloaddition, Esterification | 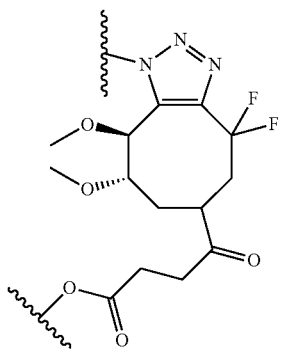 [SMILES: *OC(=O)CCC(=O)C1C[C@H](OC)[C@@H](OC)c2c(nnn2*)C(F)(F)C1] |
| [3 + 2] Cycloaddition, Esterification | 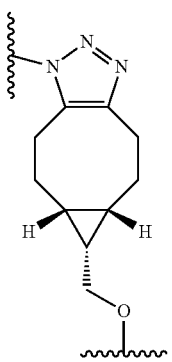 [SMILES: *OC[C@@H]1[C@@H]2CCc3c(nnn3*)CC[C@@H]21] |
| [3 + 2] Cycloaddition, Esterification | 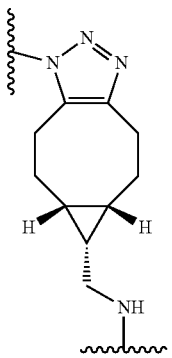 [SMILES: *NC[C@@H]1[C@@H]2CCc3c(nnn3*)CC[C@@H]21] |

TABLE 3-continued

Exemplary chemical moieties Z formed by coupling reactions in the formation of antibody-drug conjugates

| Exemplary Coupling Reactions | Chemical Moiety Z Formed by Coupling Reactions |
| --- | --- |
| [3 + 2] Cycloaddition, Esterification | |
| [3 + 2] Cycloaddition, Etherification | |
| [3 + 2] Cycloaddition | |
| Michael addition | |
| Michael addition | |
| Imine condensation, Amidation | |
| Imine condensation | |

TABLE 3-continued

Exemplary chemical moieties Z formed by coupling reactions in the formation of antibody-drug conjugates

| Exemplary Coupling Reactions | Chemical Moiety Z Formed by Coupling Reactions |
|---|---|
| Disulfide formation | [structure: S—S disulfide] |
| Thiol alkylation | [structure: S–CH2–C(=O)–] |
| Condensation, Michael addition | [structure: amidine-NH linked via CH2CH2–S to succinimide N] |

One of skill in the art will recognize that a reactive substituent Z' attached to the linker and a reactive substituent on the antibody or antigen-binding fragment thereof, are engaged in the covalent coupling reaction to produce the chemical moiety Z, and will recognize the reactive moiety Z'. Therefore, antibody-drug conjugates useful in conjunction with the methods described herein may be formed by the reaction of an antibody, or antigen-binding fragment thereof, with a linker or cytotoxin-linker conjugate, as described herein, the linker or cytotoxin-linker conjugate including a reactive substituent Z', suitable for reaction with a reactive substituent on the antibody, or antigen-binding fragment thereof, to form the chemical moiety Z.

As depicted in Table 3, examples of suitably reactive substituents on the linker and antibody or antigen-binding fragment thereof include a nucleophile/electrophile pair (e.g., a thiol/haloalkyl pair, an amine/carbonyl pair, or a thiol/α,β-unsaturated carbonyl pair, and the like), a diene/dienophile pair (e.g., an azide/alkyne pair, or a diene/α,β-unsaturated carbonyl pair, among others), and the like. Coupling reactions between the reactive substituents to form the chemical moiety Z include, without limitation, thiol alkylation, hydroxyl alkylation, amine alkylation, amine or hydroxylamine condensation, hydrazine formation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. Preferably, the linker contains an electrophilic functional group for reaction with a nucleophilic functional group on the antibody, or antigen-binding fragment thereof.

Reactive substituents that may be present within an antibody, or antigen-binding fragment thereof, as disclosed herein include, without limitation, nucleophilic groups such as (i) N-terminal amine groups, (ii) side chain amine groups, e.g. lysine, (iii) side chain thiol groups, e.g. cysteine, and (iv) sugar hydroxyl or amino groups where the antibody is glycosylated. Reactive substituents that may be present within an antibody, or antigen-binding fragment thereof, as disclosed herein include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. In some embodiments, the reactive substituents present within an antibody, or antigen-binding fragment thereof as disclosed herein include, are amine or thiol moieties. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, the reactive moiety Z' attached to the linker is a nucleophilic group which is reactive with an electrophilic group present on an antibody. Useful electrophilic groups on an antibody include, but are not limited to, aldehyde and ketone carbonyl groups. The heteroatom of a nucleophilic group can react with an electrophilic group on an antibody and form a covalent bond to the antibody. Useful nucleophilic groups include, but are not limited to, hydrazide, oxime, amino, hydroxyl, hydrazine, thiosemicarbazone, hydrazine carboxylate, and arylhydrazide.

In some embodiments, Z is the product of a reaction between reactive nucleophilic substituents present within the antibodies, or antigen-binding fragments thereof, such as amine and thiol moieties, and a reactive electrophilic substituent Z'. For instance, Z' may be a Michael acceptor (e.g., maleimide), activated ester, electron-deficient carbonyl compound, and aldehyde, among others. Several representative and non-limiting examples of reactive substituents Z' and the resulting chemical moieties Z are provided in Table 4.

TABLE 4

Complementary reactive substituents and chemical moieties

| | Functional Group on Antibody | Z' group | Z group |
|---|---|---|---|
| Naturally Occurring | —SH | maleimide | thiosuccinimide |
| | | alkene (CH2=CH–) | –S–CH2CH2– |
| | —NH2 | X–C(=O)– | –NH–C(=O)– |
| Synthetically Introduced | –C≡CH | N3– | triazole |
| | –N3 | HC≡C– | triazole |
| | | cyclooctyne | fused triazole |
| | R–C(=O)– (R = H or alkyl) | H2N–Y– (Y = O or NH) | Y–N=C(R)– |

For instance, linkers suitable for the synthesis of drug-antibody and drug-ligand conjugates include, without limitation, reactive substituents Z' such as maleimide or haloalkyl groups. These may be attached to the linker by reagents such as succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, in for instance, Liu et al., 18:690-697, 1979, the disclosure of which is incorporated herein by reference as it pertains to linkers for chemical conjugation.

In some embodiments, the reactive substituent Z' attached to linker L is a maleimide, azide, or alkyne. An example of a maleimide-containing linker is the non-cleavable maleimidocaproyl-based linker, which is particularly useful for the conjugation of microtubule-disrupting agents such as auristatins. Such linkers are described by Doronina et al., Bioconjugate Chem. 17:14-24, 2006, the disclosure of which is incorporated herein by reference as it pertains to linkers for chemical conjugation.

In some embodiments, the reactive substituent Z' is —(C=O)— or —NH(C=O)—, such that the linker may be joined to the antibody, or antigen-binding fragment thereof, by an amide or urea moiety, respectively, resulting from reaction of the —(C=O)— or —NH(C=O)— group with an amino group of the antibody or antigen-binding fragment thereof.

In some embodiments, the reactive substituent is an N-maleimidyl group, halogenated N-alkylamido group, sulfonyloxy N-alkylamido group, carbonate group, sulfonyl halide group, thiol group or derivative thereof, alkynyl group comprising an internal carbon-carbon triple bond, (hetero)cycloalkynyl group, bicyclo[6.1.0]non-4-yn-9-yl group, alkenyl group comprising an internal carbon-carbon double bond, cycloalkenyl group, tetrazinyl group, azido group, phosphine group, nitrile oxide group, nitrone group, nitrile imine group, diazo group, ketone group, (O-alkyl) hydroxylamino group, hydrazine group, halogenated N-maleimidyl group, 1,1-bis (sulfonylmethyl)methylcarbonyl group or elimination derivatives thereof, carbonyl halide group, or an allenamide group, each of which may be optionally substituted. In some embodiments, the reactive substituent comprises a cycloalkene group, a cycloalkyne group, or an optionally substituted (hetero)cycloalkynyl group.

Non-limiting examples of amatoxin-linker conjugates containing a reactive substituent Z' suitable for reaction with a reactive residue on the antibody or antigen-binding fragment thereof include, without limitation, 7'C-(4-(6-(maleimido)hexanoyl)piperazin-1-yl)-amatoxin; 7'C-(4-(6-(maleimido)hexanamido)piperidin-1-yl)-amatoxin; 7'C-(4-(6-(6-(maleimido)hexanamido)hexanoyl)piperazin-1-yl)-amatoxin; 7'C-(4-(4-((maleimido)methyl)cyclohexanecarbonyl)piperazin-1-yl)-amatoxin; 7'C-(4-(6-(4-((maleimido)methyl)cyclohexanecarboxamido)hexanoyl)piperazin-1-yl)-amatoxin; 7'C-(4-(2-(6-(maleimido)hexanamido)ethyl)piperidin-1-yl)-amatoxin; 7'C-(4-(2-(6-(6-(maleimido)hexanamido)hexanamido)ethyl)piperidin-1-yl)-amatoxin; 7'C-(4-(2-(4-((maleimido)methyl)cyclohexanecarboxamido)ethyl)piperidin-1-yl)-amatoxin; 7'C-(4-(2-(6-(4-((maleimido)methyl)cyclohexanecarboxamido)hexanamido)ethyl)piperidin-1-yl)-amatoxin; 7'C-(4-(2-(3-carboxypropanamido)ethyl)piperidin-1-yl)-amatoxin; 7'C-(4-(2-(2-bromoacetamido)ethyl)piperidin-1-yl)-amatoxin; 7'C-(4-(2-(3-(pyridin-2-yldisulfanyl)propanamido)ethyl)piperidin-1-yl)-amatoxin; 7'C-(4-(2-(4-(maleimido)butanamido)ethyl)piperidin-1-yl)-amatoxin; 7'C-(4-(2-(maleimido)acetyl)piperazin-1-yl)-amatoxin; 7'C-(4-(3-(maleimido)propanoyl)piperazin-1-yl)-amatoxin; 7'C-(4-(4-(maleimido)butanoyl)piperazin-1-yl)-amatoxin; 7'C-(4-(2-(6-(4-((maleimido)methyl)cyclohexanecarboxamido)hexanamido)ethyl)piperidin-1-yl)-amatoxin; 7'C-(3-((6-(maleimido)hexanamido)methyl)pyrrolidin-1-yl)-amatoxin; 7'C-(3-((6-(6-(maleimido)hexanamido)hexanamido)methyl)pyrrolidin-1-yl)-amatoxin; 7'C-(3-((4-((maleimido)methyl)cyclohexanecarboxamido)methyl)pyrrolidin-1-yl)-amatoxin; 7'C-(3-((6-((4-(maleimido)methyl)cyclohexanecarboxamido)hexanamido)methyl)pyrrolidin-1-yl)-amatoxin; 7'C-(4-(2-(6-(2-(aminooxy)acetamido)hexanamido)ethyl)piperidin-1-yl)-amatoxin; 7'C-(4-(2-(4-(2-(aminooxy)acetamido)butanamido)ethyl)piperidin-1-yl)-amatoxin; 7'C-(4-(4-(2-(aminooxy)acetamido)butanoyl)piperazin-1-yl)-amatoxin; 7'C-(4-(6-(2-(aminooxy)acetamido)hexanoyl)piperazin-1-yl)-amatoxin; 7'C-((4-(6-(maleimido)hexanamido)piperidin-1-yl)methyl)-amatoxin; 7'C-((4-(2-(6-(maleimido)hexanamido)ethyl)piperidin-1-yl)methyl)-amatoxin; 7'C-((4-(6-(maleimido)hexanoyl)piperazin-1-yl)methyl)-amatoxin; (R)-7'C-((3-((6-(maleimido)hexanamido)methyl)pyrrolidin-1-yl)methyl)-amatoxin; (S)-7'C-((3-((6-(maleimido)hexanamido)methyl)pyrrolidin-1-yl)methyl)-amatoxin; 7'C-((4-(2-(6-(6-(maleimido)hexanamido)hexanamido)ethyl)piperidin-1-yl)methyl)-amatoxin; 7'C-((4-(2-(4-((maleimido)methyl)cyclohexanecarboxamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((4-(2-(6-(maleimido)hexanamido)ethyl)piperazin-1-yl)methyl)-amatoxin; 7'C-((4-(2-(6-(6-(maleimido)hexanamido)hexanamido)ethyl)piperazin-1-yl)methyl)-amatoxin; 7'C-((4-(2-(4-((maleimido)methyl)cyclohexanecarboxamido)ethyl)piperazin-1-yl)methyl)-amatoxin; 7'C-((4-(2-(6-(4-((maleimido)methyl)cyclohexanecarboxamido)hexanamido)ethyl)piperazin-1-yl)methyl)-amatoxin; 7'C-((3-((6-(6-(maleimido)hexanamido)hexanamido)-S-methyl)pyrrolidin-1-yl)methyl)-amatoxin; 7'C-((3-((6-(6-(maleimido)hexanamido)hexanamido)-R-methyl)pyrrolidin-1-yl)methyl)-amatoxin; 7'C-((3-((4-((maleimido)methyl)cyclohexanecarboxamido)-S-methyl)pyrrolidin-1-yl)methyl)-amatoxin; 7'C-((3-((4-((maleimido)methyl)cyclohexanecarboxamido)-R-methyl)pyrrolidin-1-yl)methyl)-amatoxin; 7'C-((3-((6-(4-((maleimido)methyl)cyclohexanecarboxamido)hexanamido)methyl)pyrrolidin-1-yl)methyl)-amatoxin; 7'C-((4-(2-(3-carboxypropanamido)ethyl)piperazin-1-yl)methyl)-amatoxin; 7'C-((4-(6-(6-(maleimido)hexanamido)hexanoyl)piperazin-1-yl)methyl)-amatoxin; 7'C-((4-(6-(4-((maleimido)methyl)cyclohexanecarboxamido)hexanoyl)piperazin-1-yl)methyl)-amatoxin; 7'C-((4-(2-(maleimido)acetyl)piperazin-1-yl)methyl)-amatoxin; 7'C-((4-(3-(maleimido)propanoyl)piperazin-1-yl)methyl)-amatoxin; 7'C-((4-(4-(maleimido)butanoyl)piperazin-1-yl)methyl)-amatoxin; 7'C-((4-(2-(2-(maleimido)acetamido)ethyl)piperidin-1-yl)methyl)-amatoxin; 7'C-((4-(2-(4-(maleimido)butanamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((3-((6-(maleimido)hexanamido)methyl)azetidin-1-yl)methyl)-amatoxin; 7'C-((3-(2-(6-(maleimido)hexanamido)ethyl)azetidin-1-yl)methyl)-amatoxin; 7'C-((3-((4-((maleimido)methyl)cyclohexanecarboxamido)methyl)azetidin-1-yl)methyl)-amatoxin; 7'C-((3-(2-(4-((maleimido)methyl)cyclohexanecarboxamido)ethyl)azetidin-1yl)methyl)-amatoxin; 7'C-((3-(2-(6-(4-((maleimido)methyl)cyclohexanecarboxamido)hexanamido)ethyl)azetidin-1-yl)methyl)-amatoxin; 7'C-(((2-(6-(maleimido)-N-methylhexanamido)ethyl)(methyl)amino)methyl)-amatoxin; 7'C-(((4-(6-(maleimido)-N-methylhexanamido)butyl(methyl)amino)methyl)-amatoxin; 7'C-((2-(2-(6-(maleimido)hexanamido)ethyl)aziridin-1-yl)methyl)-amatoxin; 7'C-((2-(2-(6-(4-((maleimido)methyl)cyclohexanecarboxamido)hexanamido)ethyl)aziridin-1-yl)methyl)-amatoxin; 7'C-((4-(6-(6-(2-(aminooxy)acetamido)hexanamido)hexanoyl)piperazin-1-yl)methyl)-amatoxin; 7'C-((4-(1-(aminooxy)-2-oxo-6,9,12,15-tetraoxa-3-azaheptadecan-17-oyl)piperazin-1-yl)methyl)-amatoxin; 7'C-((4-(2-(2-(aminooxy)acetamido)acetyl)piperazin-1-yl)methyl)-amatoxin; 7'C-((4-(3-(2-(aminooxy)acetamido)propanoyl)piperazin-1-yl)methyl)-amatoxin; 7'C-((4-(4-(2-(aminooxy)acetamido)butanoyl)piperazin-1-yl)methyl)-amatoxin; 7'C-((4-(2-(6-(2-(aminooxy)acetamido)hexanamido)ethyl)piperidin-1-yl)methyl)-amatoxin; 7'C-((4-(2-(2-(2-(aminooxy)acetamido)acetamido)ethyl)piperidin-1-yl)methyl)-amatoxin; 7'C-((4-(2-(4-(2-(aminooxy)acetamido)butanamido)ethyl)piperidin-1-yl)methyl)-amatoxin; 7'C-((4-(20-(aminooxy)-4,19-dioxo-6,9,12,15-tetraoxa-3,18-diazaicosyl)piperidin-1-yl)methyl)-amatoxin; 7'C-(((2-(6-(2-(aminooxy)acetamido)-N-methylhexanamido)ethyl)(methyl)amino)methyl)-amatoxin; 7'C-(((4-(6-(2-(aminooxy)acetamido)-N-methylhexanamido)butyl)(methyl)amino)methyl)-amatoxin; 7'C-((3-((6-(4-((maleimido)methyl)cyclohexanecarboxamido)hexanamido)methyl)pyrrolidin-1-yl)-S-methyl)-amatoxin; 7'C-((3-((6-(4-((maleimido)methyl)cyclohexanecarboxamido)hexanamido)-R-methyl)pyrrolidin-1-yl)methyl)-amatoxin; 7'C-((4-(2-(2-bromoacetamido)ethyl)piperazin-1-yl)methyl)-amatoxin; 7'C-((4-(2-(2-bromoacetamido)ethyl)piperidin-1-yl)methyl)-amatoxin; 7'C-((4-(2-(3-(pyridine-2- yldisulfanyl)propanamido)ethyl)piperidin-1-yl)methyl)-amatoxin; 6'O-(6-(6-(maleimido)hexanamido)hexyl)-amatoxin; 6'O-(5-(4-((maleimido)methyl)cyclohexanecarboxamido)pentyl)-amatoxin; 6'O-(2-((6-(maleimido)hexyl)oxy)-2-oxoethyl)-amatoxin; 6'O-((6-(maleimido)hexyl)carbamoyl)-amatoxin; 6'O-((6-(4-((maleimido)methyl)cyclohexanecarboxamido)hexyl)carbamoyl)-amatoxin; 6'O-(6-(2-bromoacetamido)hexyl)-amatoxin; 7'C-(4-(6-(azido)hexanamido)piperidin-1-yl)-amatoxin; 7'C-(4-(hex-5-ynoylamino)piperidin-1-yl)-amatoxin; 7'C-(4-(2-(6-(maleimido)hexanamido)ethyl)piperazin-1-yl)-amatoxin; 7'C-(4-(2-(6-(6-(maleimido)hexanamido)hexanamido)ethyl)piperazin-1-yl)-amatoxin; 6'O-(6-(6-(11,12-didehydro-5,6-dihydro-dibenz[b,f]azocin-5-yl)-6-oxohexanamido)hexyl)-amatoxin; 6'O-(6-(hex-5-ynoylamino)hexyl)-amatoxin; 6'O-(6-(2-(aminooxy)acetylamido)hexyl)-amatoxin; 6'O-((6-aminooxy)hexyl)-amatoxin; and 6'O-(6-(2-iodoacetamido)hexyl)-amatoxin.

In some embodiments, the chemical moiety Z is selected from Table 3 or Table 4. In some embodiments, the chemical moiety Z is:

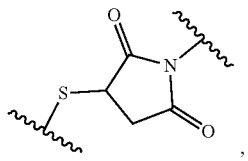

, where S is a sulfur atom which represents the reactive substituent present within an antibody, or antigen-binding fragment thereof, such as an anti-CD-5 antibody.

In some embodiments, an amatoxin as disclosed herein is conjugated to a linker-reactive moiety -L-Z' having the following formula:

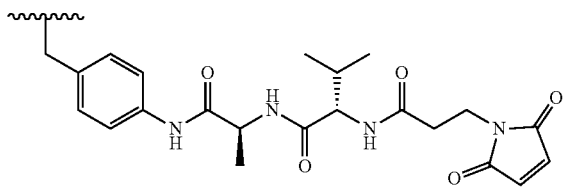 [SMILES: *Cc1ccc(NC(=O)[C@H](C)NC(=O)[C@@H](NC(=O)CCN2C(=O)C=CC2=O)C(C)C)cc1]

where the wavy line indicates the point of attachment to a substituent on the cytotoxin (e.g., an amatoxin). This linker-reactive substituent group L-Z' may alternatively be referred to as N-beta-maleimidopropionyl-Val-Ala-para-aminobenzyl (BMP-Val-Ala-PAB).

In some embodiments, an amatoxin as disclosed herein is conjugated to a linker-reactive moiety -L-Z' having the following formula:

where the wavy line indicates the point of attachment to a substituent on the cytotoxin (e.g., an amatoxin). This linker-reactive substituent group L-Z' may alternatively be referred to as N-beta-maleimidopropyl-Val-Cit-para-aminobenzyl (BMP-Val-Cit-PAB).

In some embodiments, the linker L and the chemical moiety Z, taken together as L-Z, is 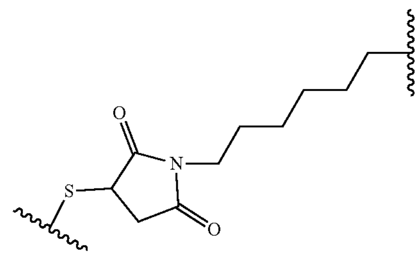 or 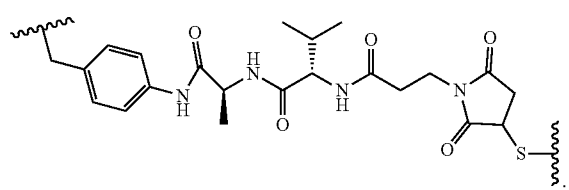 where S is a sulfur atom which represents the reactive substituent present within an antibody, or antigen-binding fragment thereof, such as an anti-CD-5 antibody. The wavy line at the linker terminus indicates the point of attachment to the amatoxin.

In some embodiments, the linker L and the chemical moiety Z, after conjugation to the antibody, taken together as L-Z-Ab, has the structure:

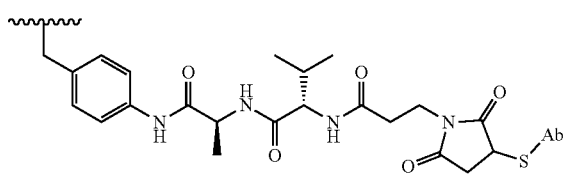

The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

In one embodiment, the CD5 antibodies, or antigen-binding fragments, described herein may be bound to an amatoxin so as to form a conjugate represented by the formula Ab-Z-L-Am, wherein Ab is the CD5 antibody, or antigen-binding fragment thereof, L is a linker, Z is a chemical moiety and Am is an amatoxin, each as described herein.

In some embodiments, Am-L-Z-Ab is:

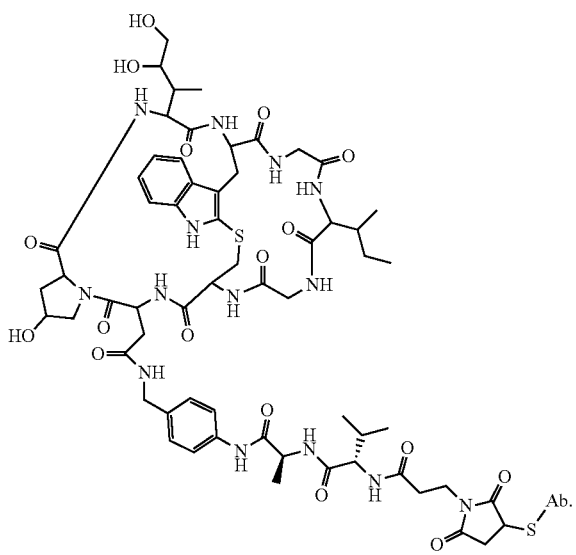

In some embodiments, Am-L-Z-Ab is:

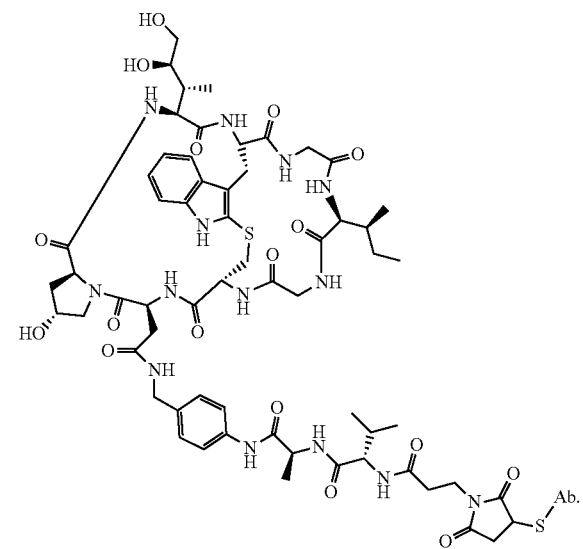

In some embodiments, Am-L-Z-Ab is:

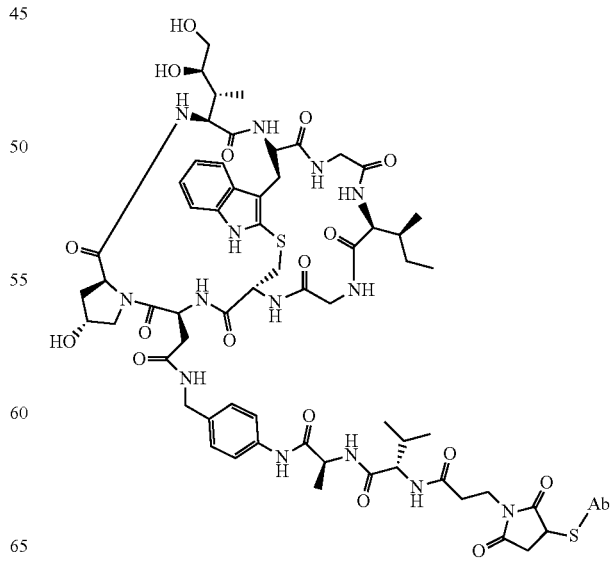

In some embodiments, Am-L-Z-Ab is:

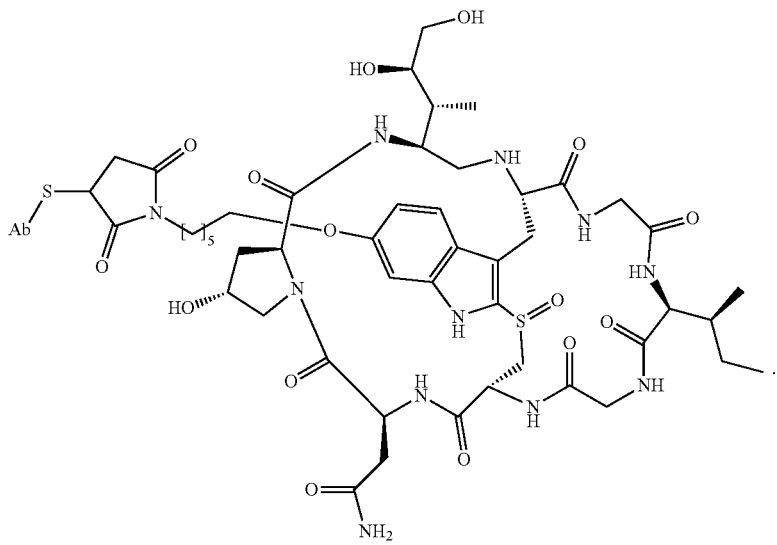

In some embodiments, Am-L-Z-Ab is:

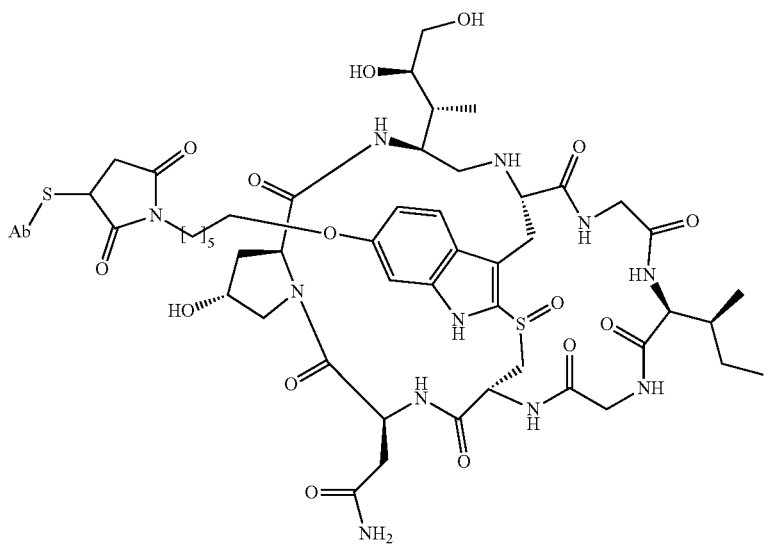

Preparation of Antibody-Drug Conjugates

In the ADCs of formula I as disclosed herein, an anti-CD5 antibody or antigen binding fragment thereof is conjugated to one or more cytotoxic drug moieties (D), e.g. about 1 to about 20 drug moieties per antibody, through a linker L and a chemical moiety Z as disclosed herein. The ADCs of the present disclosure may be prepared by several routes, employing organic chemistry reactions, conditions, and reagents known to those skilled in the art, including: (1) reaction of a reactive substituent of an antibody or antigen binding fragment thereof with a bivalent linker reagent to form Ab-Z-L as described herein above, followed by reaction with a drug moiety D; or (2) reaction of a reactive substituent of a drug moiety with a bivalent linker reagent to form D-L-Z', followed by reaction with a reactive substitu-ent of an antibody or antigen binding fragment thereof as described herein above. Additional methods for preparing ADC are described herein.

In another aspect, the anti-CD5 antibody or antigen binding fragment thereof has one or more lysine residues that can be chemically modified to introduce one or more sulfhydryl groups. The ADC is then formed by conjugation through the sulfhydryl group's sulfur atom as described herein above. The reagents that can be used to modify lysine include, but are not limited to, N-succinimidyl S-acetylthioacetate (SATA) and 2-Iminothiolane hydrochloride (Traut's Reagent).

In another aspect, the anti-CD5 antibody or antigen binding fragment thereof can have one or more carbohydrate groups that can be chemically modified to have one or more sulfhydryl groups. The ADC is then formed by conjugation through the sulfhydryl group's sulfur atom as described herein above.

In yet another aspect, the anti-CD5 antibody can have one or more carbohydrate groups that can be oxidized to provide an aldehyde (—CHO) group (see, for e.g., Laguzza, et al., J. Med. Chem. 1989, 32(3), 548-55). The ADC is then formed by conjugation through the corresponding aldehyde as described herein above. Other protocols for the modification of proteins for the attachment or association of cytotoxins are described in Coligan et al., Current Protocols in Protein Science, vol. 2, John Wiley & Sons (2002), incorporated herein by reference.

Methods for the conjugation of linker-drug moieties to cell-targeted proteins such as antibodies, immunoglobulins or fragments thereof are found, for example, in U.S. Pat. Nos. 5,208,020; 6,441,163; WO2005037992; WO2005081711; and WO2006/034488, all of which are hereby expressly incorporated by reference in their entirety.

Routes of Administration and Dosing

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

ADCs described herein can be administered to a patient (e.g., a human patient suffering from an immune disease or cancer) in a variety of dosage forms. For instance, ADCs described herein can be administered to a patient suffering from an immune disease or cancer in the form of an aqueous solution, such as an aqueous solution containing one or more pharmaceutically acceptable excipients. Suitable pharmaceutically acceptable excipients for use with the compositions and methods described herein include viscosity-modifying agents. The aqueous solution may be sterilized using techniques known in the art.

Pharmaceutical formulations comprising anti-CD5 ADCs as described herein are prepared by mixing such ADC with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

The amount of ADC administered should be sufficient to deplete cells, e.g., activated T cells, which reject CAR cell therapy. The determination of a therapeutically effective dose is within the capability of practitioners in this art, however, as an example, in embodiments of the method described herein utilizing systemic administration of an ADC for the treatment of an immune disease or cancer, an effective human dose will be in the range of 0.1-150 mg/kg (e.g., 5 mg/kg, 10 mg/kg, 25 mg/kg, 50 mg/kg, 75 mg/kg, 100 mg/kg, 150 mg/kg etc.). The route of administration may affect the recommended dose. Repeated systemic doses are contemplated in order to maintain an effective level, e.g., to reduce the risk of CAR-T cell rejection, depending on the mode of administration adopted.

The anti-CD5 ADCs described herein may be administered by a variety of routes, such as orally, transdermally, subcutaneously, intranasally, intravenously, intramuscularly, intraocularly, or parenterally. The most suitable route for administration in any given case will depend on the particular ADC, the patient, pharmaceutical formulation methods, administration methods (e.g., administration time and administration route), the patient's age, body weight, sex, severity of the diseases being treated, the patient's diet, and the patient's excretion rate.

The effective dose of an anti-CD5 ADC described herein can range, for example from about 0.001 to about 100 mg/kg of body weight per single (e.g., bolus) administration, multiple administrations, or continuous administration, or to achieve an optimal serum concentration (e.g., a serum concentration of 0.0001-5000 µg/mL) of the anti-CD5 ADC. A dose of the anti-CD5 ADC may be administered one or more times (e.g., 2-10 times) per day, week, or month to a human subject who has had, is concomitantly receiving, or will be receiving CAR therapy at a time point following delivery of the antu-CD5 ADC. An anti-CD5 ADC may be administered to the human patient one time or as multiple doses. In one embodiment, the anti-CD5 ADC can be administered in an amount sufficient to reduce the quantity of host-reactive T cells, for example, by 10%, 20%, 30%, 40%, 50%, 60%, 70%, 80%, 90%, 95%, or more prior to CAR therapy.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1: In Vitro Binding Analysis of Anti-CD5 Antibodies

To determine the binding characteristics of anti-CD5 antibody 5D7 hIgG1, antibody binding studies were performed at 25 degrees Celsius in 1×PBS supplemented with 0.1% w/v bovine serum albumin with a Pall ForteBio Octet Red96 using biolayer interferometry (BLI). The purified human anti-CD5 antibody (5D7) was immobilized onto anti-human Fc biosensors (AHC; Pall ForteBio 18-5063) and incubated with 50 nM of purified human CD5 ectodomain). The binding characteristics of anti-CD5 antibody 5D7 are shown in Table 4. Anti-human CD5 antibody 5D7 as used in Examples 1 to 5 is a humanized version of murine antibody 5D7 (see US 2008/0254027). The sequences of antibody 5D7 as used herein are described in SEQ ID Nos: 53 and 54 (heavy and light chain variable region amino acid sequences) and SEQ ID Nos: 47 to 52 (heavy and light chain CDRs).

TABLE 4

Binding kinetics of 5D7 to human CD5 ectodomain

| Antibody | Conc. (nM) | Response (nm) | $K_D$ (M) | $K_{ON}$ (1/Ms) | $K_{DIS}$ (1/s) | Full $R^2$ |
|---|---|---|---|---|---|---|
| 5D7 | 50 | 0.6696 | 1.41E−10 | 2.39E+05 | 3.36E−05 | 0.9996 |

Example 2: In Vitro Cell Line Binding Analysis of Anti-CD5 Antibodies

MOLT-4 cells (i.e., an immortalized human T lymphoblast cell line) were plated at 20,000 cells/well and stained with a titration of the indicated murine anti-CD5 antibodies (i.e., L17F12, UCHT2, 205919, and CRIS-1) for 2 hours at 4° C. Secondary anti-mouse AF488 stain, at a constant amount, was added for 30 minutes at 4° C. After washing, plates were run on a flow cytometer and binding of the indicated antibody (and the negative control, i.e., mIgG1) was determined based on geometric mean fluorescence intensity in the AF488 channel. Results from these assays are provided in FIG. 1.

Figure 1:
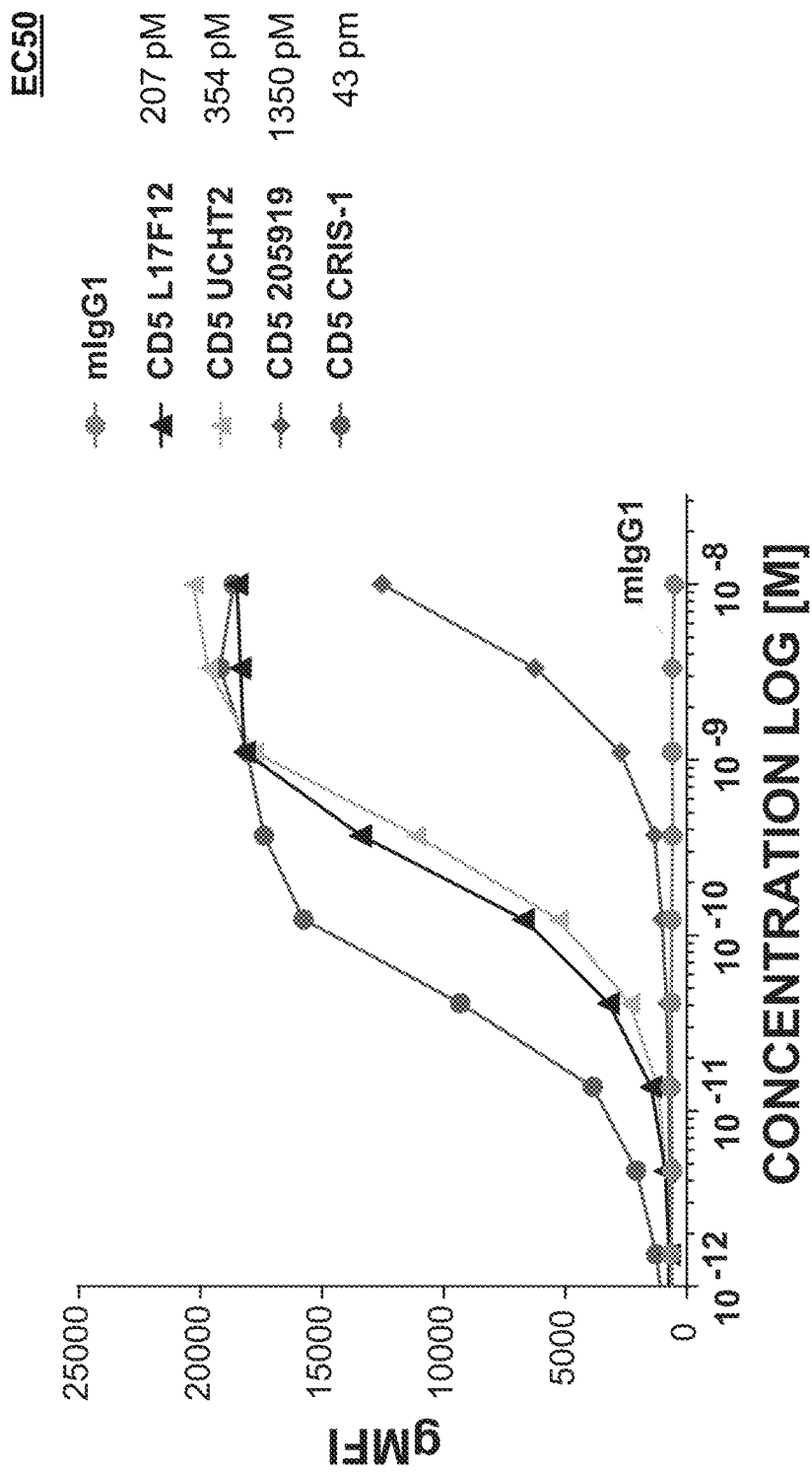
FIG. 1 graphically depicts the results of an in vitro cell line binding assay in which each of the indicated anti-CD5 antibodies or a negative control (i.e., mIgG1) was incubated with MOLT-4 cells (i.e., a human T lymphoblast cell line) followed by incubation of a fluorophore-conjugated anti-IgG antibody. Signal was detected through flow cytometry and is indicated as the geometric mean fluorescence intensity (y-axis) as a function of anti-CD5 antibody concentration (x-axis).

As shown in FIG. 1, the murine anti-CD5 antibodies L17F12 (Thermo Fisher), UCHT2 (BioLegend), 205919 (Novus Biologicals), and CRIS-1 (Novus Biologicals) bound to human T lymphoblast cells (i.e. MOLT-4 cells), with an $EC_{50}$=207 pM (L17), 354 pM (UCH), 1350 pM (205), and 43 pM (CRIS).

Example 3: In Vitro Primary Cell Binding Analysis of Anti-CD5 Antibodies

Primary human T-cells were plated at $8 \times 10^4$ cells/well and stained with a titration of the human anti-CD5 antibody 5D7 for 2 hours at 37° C. Secondary anti-mouse AF488 stain, at a constant amount, was added for 30 minutes at 4° C. After washing, plates were run on a flow cytometer and binding of the anti-CD5 5D7 antibody (and the negative control, i.e., hIgG1) was determined based on geometric mean fluorescence intensity in the AF488 channel. Results from these assays are provided in FIG. 2.

Figure 2:
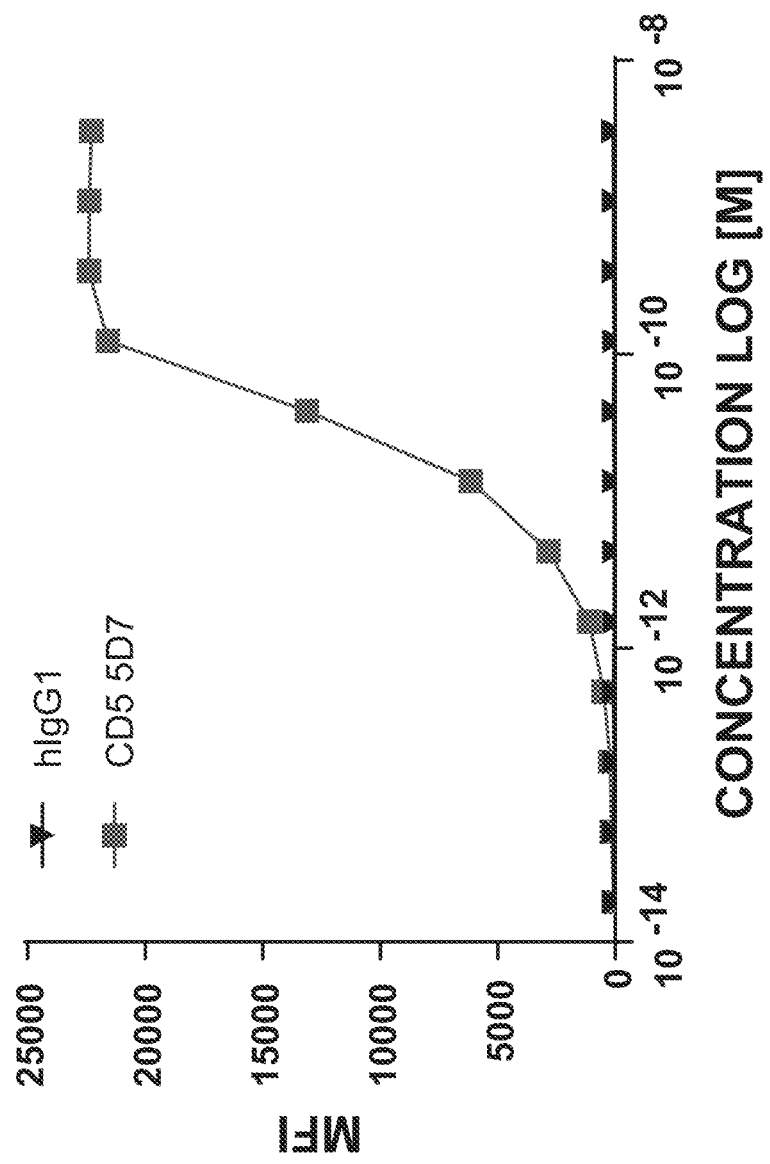
FIG. 2 graphically depicts the results of an in vitro primary cell binding assay in which the indicated anti-CD5 antibody (i.e., "CD5 5D7") or a negative control (i.e., hIgG1) was incubated with primary human T-cells followed by incubation of a fluorophore-conjugated anti-IgG antibody. Signal was detected through flow cytometry and is indicated as the geometric mean fluorescence intensity (y-axis) as a function of anti-CD5 antibody concentration (x-axis).

As shown in FIG. 2, the anti-CD5 antibody 5D7 bound to primary human T-cells with an $EC_{50}$=3.0 pM.

Example 4. In Vitro Analysis of an Anti-CD5-Amatoxin Antibody Drug Conjugate (ADC) Using an In Vitro T-Cell Killing Assay The anti-CD5 antibody 5D7 was conjugated to an amatoxin (amanitin) with a cleavable linker to form an anti-CD5 5D7ADC. Anti-CD5 5D7-ADCs having a drug to antibody ratio (DAR) of about 6 (interchain DAR6) were tested, as well as anti-CD5 5D7-ADCs having a DAR of about 2 (prepared using site-specific conjugation via a D265C mutation). Further, a fast half-life variant of the anti-CD5 5D7-ADC was generated through the introduction of an H435A mutation within the Fc region.

Each anti-CD5 5D7-ADC was assessed using an in vitro human T-cell killing assay.

Cryopreserved negatively-selected primary human T cells were thawed and stimulated with anti-CD3 antibodies and IL-2. At the start of the assay, $2 \times 10^4$ T cells were seeded per well of a 384 well plate and the indicated ADCs or non-conjugated anti-CD5 antibody were added to the wells at various concentrations between 0.003 nm and 30 nm before being placed in an incubator with 37° C. and 5% $CO_2$.

Following five days of culture, cells were analyzed by flow cytometry. Cells were stained with a viability marker 7-AAD and run on a volumetric flow cytometer.

Numbers of viable T-cells (FIGS. 3A and 3B) were determined by FSC vs SSC and 7-AAD. A non-conjugated anti-CD5 5D7 antibody served as a comparator (FIG. 3A).

Figure 3A:
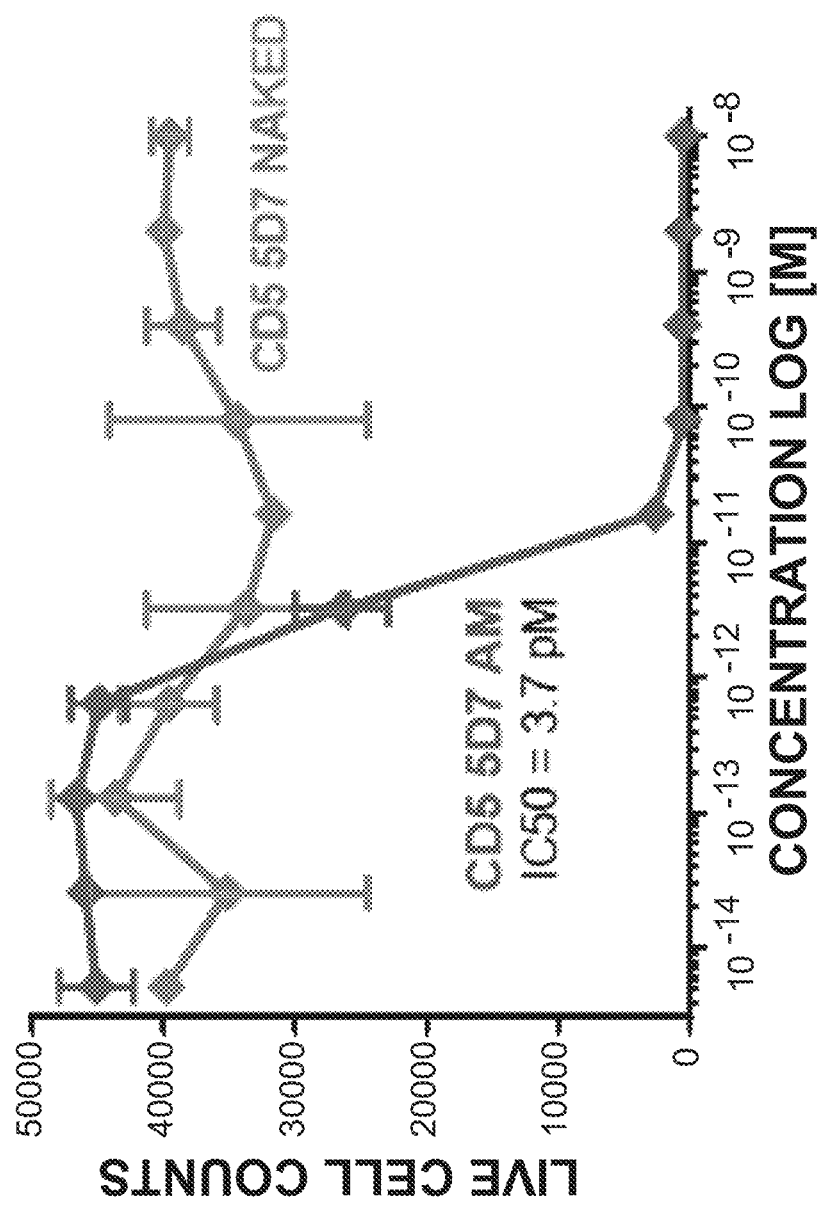
FIGS. 3A and 3B graphically depict results of an in vitro T cell killing assay including an anti-CD5-amanitin ADC (i.e., 5D7-AM or "CD5 5D7 AM") having an interchain conjugated amanitin with an average drug-to-antibody ratio (DAR) of 6 (FIG. 3A) or a site-specific conjugated amanitin with a DAR of 2 (FIG. 3B).
Figure 3B:
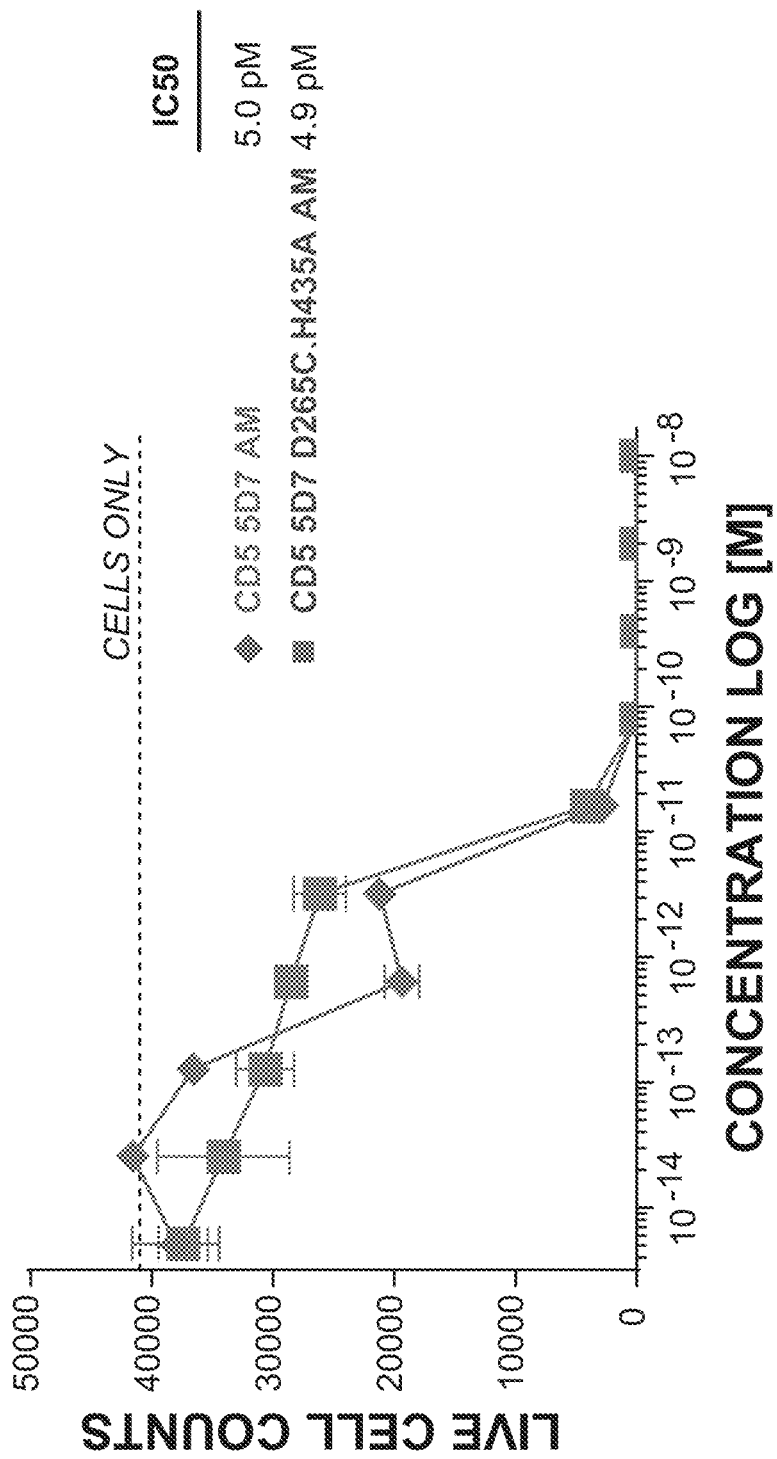

As shown in FIG. 3A, anti-CD5 5D7-ADCs having a DAR of about 6 exhibited potent and specific killing of human T cells (IC50=3.7 pm) whereas T cells remained viable in the presence of non-conjugated ("naked") anti-CD5 5D7 antibodies. As shown in FIG. 3B, ADCs having a site-specific (D265C) DAR of about 2 retained a potent level of T-cell killing (IC50=5.0 pm) similar to that of the DAR 6 ADCs. The fast-half life variant of the anti-CD5 5D7-ADC (H435A) exhibited a similar level of T-cell killing (IC50=4.9 pm; FIG. 3B).

Example 5. Analysis of T-Cell Depletion Using a hNSG Mouse Model

In vivo T-cell depletion assays were conducted using humanized NSG mice (Jackson Laboratories). Anti-CD5 antibody 5D7 was conjugated to amatoxin (amanitin) with a cleavable linker to form an anti-CD5 5D7-ADC. Anti-CD5 5D7-ADCs were prepared either as a DAR of about 6 or aDAR of about 2, as described above. Each anti-CD5 5D7ADC (DAR6 or DAR2) was administered as a single intravenous injection (0.3 mg/kg, 1 mg/kg, or 3 mg/kg for DAR6 ADCs, or 1 mg/kg or 3 mg/kg for DAR2 ADCs) to the humanized mouse. Peripheral blood cells, bone marrow, or thymic samples were collected on Day 7 and the absolute number of CD3+ T-cells was determined by flow cytometry (see FIGS. 4A-4B for DAR2 ADCs, and 5A-5C for DAR6 ADCs).

As shown in, FIGS. 4A-4B, humanized NSG mice treated with 0.3 mg/kg, 1 mg/kg, or 3 mg/kg DAR6 anti-CD5 5D7-ADCs exhibited potent T-cell depletion in peripheral blood or bone morrow while thymic T-cells were depleted following treatment with 1 mg/kg or 3 mg/kg of DAR6 anti-CD5 5D7-ADCs. Negative controls used in this in vivo experiment included a human IgG1 not specific to CD5 (as a naked antibody (huIgG1) and conjugated to an amatoxin (huIgG1-AM). As described in FIGS. 4A to 4B, the huIgG1 naked and conjugated controls had no impact on T cell depletion in peripheral blood (FIG. 4A) and bone marrow (FIG. 4B) as these controls were comparable to the PBS control. An anti-CD5 antibody (antibody YTH34.5) was used as a control as well, and was also able to deplete peripheral and bone marrow T cells at a dose of 25 mg/kg.

As shown in, FIGS. 5A-5C, humanized NSG mice treated with 1 mg/kg site or 3 mg/kg site-specific DAR2 anti-CD5 5D7-ADC exhibited potent T-cell depletion in peripheral blood, bone morrow, and thymic T-cells. In each of FIGS. 5A to 5C, naked antibody 5D7 was also used as a control. Antibody 5D7 was able to deplete peripheral T cells (relative to a non-specific human IgG1 control or PBS) as described in FIG. 5A, but was unable to deplete either marrow T cells or thymic T cells whereas the 5D7-AM ADC was effective at depleting both marrow and thymic as described in FIGS. 5B and 5C.

Example 6. Administration of Allogeneic CAR-T Cells in a Mouse Model

The following study is performed to assess the level of CAR-T cells present in an allogeneic recipient under different conditions.

A murine allogeneic CAR-T model is used for this study.

A first treatment group of mice is treated with a priming dose of allogeneic T cells, by administration of $1 \times 10^7$ to $1 \times 10^9$ cells/kg by intravenous infusion at Day 0. On Day 3, the mice are administered an anti-CD5-α-amanitin ADC at a dose of 3 mg/kg. On Day 10, after the ADC has substantially cleared from the blood of the mice, mice are administered allogeneic CAR-T cells. The CAR-T cells are from the same donor as the allogeneic T cells administered on Day 0.

A second treatment group of mice is treated using the same protocol as the first treatment group, but is administered an unconjugated anti-CD5 antibody on Day 3, in place of the anti-CD5 ADC.

A third treatment group of mice is treated using the same protocol as the first treatment group, but is administered an isotype control antibody conjugated to α-amanitin on Day 3, in place of the anti-CD5 ADC.

A fourth treatment group of mice is treated using the same protocol as the first treatment group, but is administered a priming dose of autologous T cells at Day 0, in place of the allogeneic T cells.

A fifth treatment group of mice is administered allogeneic CAR-T cells at Day 10, without prior treatment.

A sixth treatment group of mice is administered autologous CAR-T cells at Day 10, without prior treatment.

The number of CAR-T cells present in spleen and peripheral blood of mice from each treatment group is determined at Day 14, Day 17, and Day 30. The number of CD5+ activated T cells in the spleen and peripheral blood of mice from each treatment group is determined at Day 9. Mice are monitored for symptoms of rejection throughout the study.

Example 7. Administration of an Anti-CD5 Antibody Drug Conjugate to a Human Patient to Prevent Rejection of an Allogeneic Cell Therapy A human patient is selected to receive an allogeneic cell therapy, such as an allogeneic CAR cell therapy. To inhibit or prevent the rejection of the allogeneic cells, an anti-CD5 antibody drug conjugate (ADC) is administered in accordance with the methods disclosed herein. The physician carries out the following treatment steps.

First, an initial amount of an allogeneic cell is intravenously administered to the patient in an amount sufficient to elicit a priming immune response to the allogeneic cell. In the priming step, allogeneic cells are administered to the patient to elicit an immune response resulting in endogenous activated CD5+ T cells.

Subsequently, the patient is administered an anti-CD5 ADC comprising an anti-CD5 antibody conjugated to a cytotoxin via a linker. The anti-CD5 ADC is administered in an amount effective to deplete endogenous CD5+ activated T cells. The level of CD5+ activated T cells is assessed in the patient following administration of the anti-CD5 ADC to confirm depletion.

Next, the patient is administered a therapeutically effective amount of allogeneic cells expressing a CAR. The allogeneic cells are derived from the same donor as the cells administered to the patient during the priming step. Acceptance of the allogeneic cells in the recipient patient is promoted and the risk of rejection is reduced, relative to patients receiving an allogeneic cell therapy without priming and administration of an anti-CD5 ADC.

TABLE 5

Sequence Summary

| Sequence Identifier | Description | Sequence |
| --- | --- | --- |
| SEQ ID NO: 58 | Light chain variable region | DIQMTQSPSSMSASLGDRVTITCRASQDINSYLSWFQ QKPGKSPKTLIYRANRLVDGVPSRFSGSGSGTDYTLTI SSLQYEDFGIYYCQQYDESPWTFGGGTKLEIK |
| SEQ ID NO: 59 | Heavy chain variable region | QIQLVQSGPGLKKPGGSVRISCAASGYTFTNYGMNWV KQAPGKGLRWMGWINTHTGEPTYADDFKGRFTFSLD TSKSTAYLQINSLRAEDTATYFCTRRGYDWY FDVWGQGTTVTVSS |
| SEQ ID NO: 21 | CDR-H1 | GYTFTNY |
| SEQ ID NO: 22 | CDR-H2 | NTHTGE |
| SEQ ID NO: 23 | CDR-H3 | RGYDWYFDV |
| SEQ ID NO: 24 | CDR-L1 | RASQDINSYLS |
| SEQ ID NO: 25 | CDR-L2 | RANRLVD |
| SEQ ID NO: 26 | CDR-L3 | QQYDESPWT |
| SEQ ID NO: 27 | Light chain variable region | DIQMTQSPSSLSASVGDRVTITCRASQDINSYLSWFQQ KPGKAPKTLIYRANRLESGVPSRFSGSGSGTDYTLTIS SLQYEDFGIYYCQQYDESPWTFGGGTKLEIK |
| SEQ ID NO: 28 | Heavy chain variable region | EIQLVQSGGGLVKPGGSVRISCAASGYTFTNYGMNWV RQAPGKGLEWMGWINTHYGEPTYADSFKGTRTFSLD DSKNTAYLQINSLRAEDTAVYFCTRRGYDWYFDVWGQ GGTTVTVSS |
| SEQ ID NO: 29 | CDR-H1 | GYTFTNY |
| SEQ ID NO: 30 | CDR-H2 | NTHYGE |

TABLE 5-continued

Sequence Summary

| Sequence Identifier | Description | Sequence |
| --- | --- | --- |
| SEQ ID NO: 31 | CDR-H3 | RRGYDWYFDV |
| SEQ ID NO: 32 | CDR-L1 | RASQDINSYLS |
| SEQ ID NO: 33 | CDR-L2 | RANRLES |
| SEQ ID NO: 34 | CDR-L3 | QQYDESPWT |
| SEQ ID NO: 35 | CDR-H1 | GYSITSGYY |
| SEQ ID NO: 36 | CDR-H2 | ISYSGFT |
| SEQ ID NO: 37 | CDR-H3 | AGDRTGSWFAY |
| SEQ ID NO: 38 | CDR-L1 | QDISNY |
| SEQ ID NO: 39 | CDR-L2 | ATS |
| SEQ ID NO: 40 | CDR-L3 | LQYASYPFT |
| SEQ ID NO: 41 | CDR-H1 | GYIFTNYG |
| SEQ ID NO: 42 | CDR-H2 | INTYNGEP |
| SEQ ID NO: 43 | CDR-H3 | ARGDYYGYEDY |
| SEQ ID NO: 44 | CDR-L1 | QGISNY |
| SEQ ID NO: 45 | CDR-L2 | YTS |
| SEQ ID NO: 46 | CDR-L3 | QQYSKLPWT |
| SEQ ID NO: 47 | 5D7 CDR-H1 | FSLSTSGMG |
| SEQ ID NO: 48 | 5D7 CDR-H2 | WWDDD |
| SEQ ID NO: 49 | 5D7 CDR-H3 | RRATGTGFDY |
| SEQ ID NO: 50 | 5D7 CDR-L1 | QDVGTA |
| SEQ ID NO: 51 | 5D7 CDR-L2 | WTSTRHT |
| SEQ ID NO: 52 | 5D7 CDR-L3 | YNSYNT |
| SEQ ID NO: 53 | Humanized 5D7 Heavy chain variable region (CDRs in bold) | QVTLKESGPVLVKPTETLTLTCTFSGFSLSTSGM GVGWIRQAPGKGLEWVAHIWWDDDVYYNPSLKS RLTITKDASKDQVSLKLSSVTAADTAVYYCVRRRA TGTGFDYWGQGTLVTVSS |
| SEQ ID NO: 54 | Humanized 5D7 Light chain variable region (CDRs in bold) | NIVMTQSPSSLSASVGDRVTITCQASQDVGTAVA WYQQKPDQSPKLLIYWTSTRHTGVPDRFTGSGS GTDFTLTISSLQPEDIATYFCHQYNSYNTFGSGTK LEIK |
| SEQ ID NO: 55 | Consensus human Heavy chain variable domain (CDRs in bold) | EVQLVESGGGLVQPGGSLRLSCAASGFTFSDYA MSWVRQAPGKGLEWVAVISENGSDTYYADSVKG RFTISRDDSKNTLYLQMNSLRAEDTAVYYCARDR GGAVSYFDVWGQGTLVTVSS |
| SEQ ID NO: 56 | Consensus human Light chain variable domain (CDRs in bold) | DIQMTQSPSSLSASVGDRVTITCRASQDVSSYLA WYQQKPGKAPKLLIYAASSLESGVPSRFSGSGS GTDFTLTISSLQPEDFATYYCQQYNSLPYTFGQG TKVEIKRT |
| SEQ ID NO: 57 | Human CD5 amino acid sequence | MVCSQSWGRS SKQWEDPSQA SKVCQRLNCG VPLSLGPFLV TYTPQSSIIC YGQLGSFSNCSHSRNDMCHS LGLTCLEPQK TTPPTTRPPP TTTPEPTAPP RLQLVAQSGG QHCAGVVEFYSGSLGGTISY EAQDKTQDLE NFLCNNLQCG SFLKHLPETE AGRAQDPGEP REHQPLPIQWKIQNSSCTSL EHCFRKIKPQ KSGRVLALLC SGFQPKVQSR LVGGSSICEG TVEVRQGAQWAALCDSSSAR SSLRWEEVCR EQQCGSVNSY RVLDAGDPTS RGLFCPHQKL SQCHELWERNSYCKKVFVTC QDPNPAGLAA |

TABLE 5-continued

Sequence Summary

| Sequence Identifier | Description | Sequence |
|---|---|---|
| | | GTVASIILAL VLLVVLLVVC GPLAYKKLVK KFRQKKQRQW IGPTGMNQNM SFHRNHTATV RSHAENPTAS HVDNEYSQPP RNSHLSAYPA LEGALHRSSMQPDNSSDSDY DLHGAQRL |

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

The invention claimed is:

1. A method of promoting acceptance of an immune cell expressing a chimeric antigen receptor (CAR) in a human subject having cancer or an autoimmune disease, the method comprising:
   (a) administering an anti-CD5 antibody drug conjugate (ADC) to a human subject having cancer or an autoimmune disease, wherein the anti-CD5 ADC comprises an anti-CD5 antibody, or antigen-binding fragment thereof, conjugated to a cytotoxin via a linker; and
   (b) after administering said anti-CD5 antibody drug conjugate, administering a therapeutically effective amount of an immune cell expressing a CAR to the human subject, wherein the CAR comprises an extracellular domain that binds to a tumor antigen or an antigen associated with an autoimmune disease, a transmembrane domain, and a cytoplasmic domain.

2. The method of claim 1, wherein the human subject is not administered alemtuzumab and/or a lymphodepleting chemotherapeutic agent prior to, concomitantly with, or following step (b).

3. The method of claim 2, wherein said human subject is not administered a lymphodepleting chemotherapeutic agent, the lymphodepleting chemotherapeutic agent is selected from the group consisting of fludarabine, cyclophosphamide, bendamustine, and pentostatin.

4. The method of claim 1, further comprising administering an anti-CD2 ADC to the human subject prior to step (b).

5. The method of claim 1, wherein the immune cell is an allogeneic cell or an autologous cell.

6. The method of claim 5, wherein said immune cell is an allogeneic cell is selected from the group consisting of an allogeneic T cell and an allogeneic NK cell.

7. A method of treating a patient having a tumor, comprising:
administering to a subject in need thereof:
(i) an anti-CD5 ADC, wherein the anti-CD5 ADC comprises an anti-CD5 antibody, or antigen-binding fragment thereof, conjugated to a cytotoxin via a linker, and
(ii) after administering said anti-CD5 ADC, administering to the patient a therapeutically effective amount of from about $1 \times 10^6$ to about $1 \times 10^8$ engineered CAR T cells/kg.

8. The method of claim 1, wherein the anti-CD5 ADC is administered to the patient as a single dose or as multiple doses.

9. The method of claim 1, wherein the anti-CD5 antibody, or antigen-binding fragment thereof, comprises a heavy chain variable region comprising a CDR1, a CDR2, and a CDR3 having an amino acid sequence as set forth in SEQ ID NOs: 3, 4, and 5, respectively, and comprises a light chain variable region comprising a CDR1, a CDR2, and a CDR3 having an amino acid sequence as set forth in SEQ ID NOs: 6, 7, and 8, respectively.

10. The method of claim 1, wherein the cytotoxin is an antimitotic agent or an RNA polymerase inhibitor.

11. The method of claim 10, wherein said cytotoxin is an RNA polymerase inhibitor which is an amatoxin.

12. The method of claim 11, wherein the anti-CD5 antibody, or antigen-binding fragment thereof conjugated to an amatoxin is represented by the formula Ab-Z-L-Am, wherein Ab is the antibody or antigen—binding fragment thereof, L is a linker, Z is a chemical moiety, and Am is an amatoxin represented by formula (III)

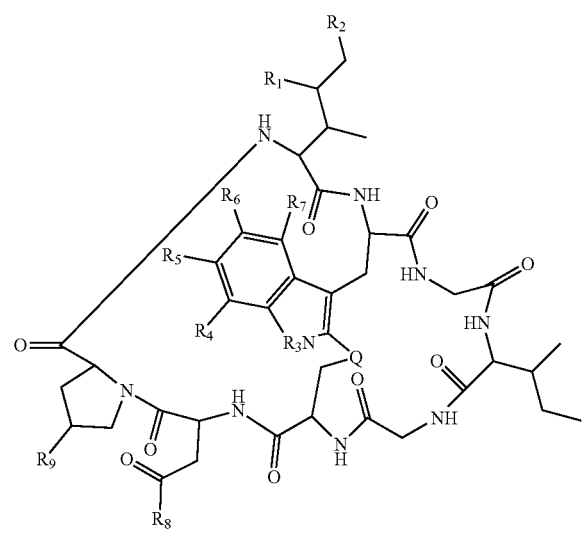

(III)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine
to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;
$R_9$ is H, OH, $OR_C$, or $OR_D$;
Q is —S—, —S(O)—, or —SO$_2$—;
$R_C$ is -L-Z;
$R_D$ is optionally substituted $C_1$-$C_6$ alkyl, optionally substituted $C_1$-$C_6$ heteroalkyl, optionally
substituted $C_2$-$C_6$ alkenyl, optionally substituted $C_2$-$C_6$ heteroalkenyl, optionally substituted $C_2$-$C_6$
alkynyl, optionally substituted $C_2$-$C_6$ heteroalkynyl, optionally substituted cycloalkyl, optionally
substituted heterocycloalkyl, optionally substituted aryl, or optionally substituted heteroaryl;
L is a linker; and
Z is a chemical moiety formed from a coupling reaction between a reactive substituent present on L and a reactive substituent present within the anti-CD5 antibody or antigen-binding fragment thereof, wherein Am comprises exactly one $R_C$ substituent.

13. The method of claim 10, wherein said cytotoxin is at least one antimitotic agent selected from the group consisting of a maytansine, an auristatin, a pyrrolobenzodiazepine (PBD), and a calicheamicin.

14. The method of claim 11, wherein the linker of the ADC is N-beta-maleimidopropionyl-Val-Ala-para-aminobenzyl (BMP-Val-Ala-PAB).

15. The method of claim 1, wherein the extracellular domain of the CAR comprises an scFv antibody or a single chain T cell receptor (scTCR).

16. The method of claim 1, wherein the tumor antigen is an antigen selected from the group consisting of CD19, CD22, CD30, CD7, BCMA, CD137, CD22, CD20, AFP, GPC3, MUC1, mesothelin, CD38, PD1, EGFR, MG7, BCMA, TACI, CEA, PSCA, CEA, HER2, MUC1, CD33, ROR2, NKR-2, PSCA, CD28, TAA, NKG2D, or CD123.

17. The method of claim 1, wherein the cytoplasmic domain of the CAR comprises a CD28 cytoplasmic signaling domain, a CD3 zeta cytoplasmic signaling domain, an OX40 cytoplasmic signaling domain, and/or a CD137 (4-1BB) cytoplasmic signaling domain.

18. The method of claim 1, wherein the cytoplasmic domain of the CAR comprises a CD3 zeta cytoplasmic signaling domain.

19. The method of claim 1, wherein the human subject having cancer has a cancer selected from the group consisting of leukemia, adult advanced cancer, pancreatic cancer, non-resectable pancreatic cancer, colorectal cancer, metastatic colorectal cancer, ovarian cancer, triple-negative breast cancer, hematopoietic/lymphoid cancer, colon cancer liver metastasis, small cell lung cancer, non-small cell lung cancer, B-cell lymphoma, relapsed or refractory B-cell lymphoma, follicular lymphoma, mantle cell lymphoma, diffuse large cell lymphoma, relapsed or refractory diffuse large cell lymphoma, anaplastic large cell lymphoma, primary mediastinal B-cell lymphoma, recurrent mediastinal, refractory mediastinal large B-cell lymphoma, large B-cell lymphoma, Hodgkin lymphoma, non-Hodgkin lymphoma, relapsed or refractory non-Hodgkin lymphoma, refractory aggressive non-Hodgkin lymphoma, B-cell non-Hodgkin lymphoma, refractory non-Hodgkin lymphoma, colorectal carcinoma, gastric carcinoma, pancreatic carcinoma, triple-negative invasive breast carcinoma, renal cell carcinoma, lung squamous cell carcinoma, hepatocellularcarcinoma, urothelial carcinoma, leukemia, B-cell leukemia, B-cell acute lymphocytic leukemia, B-cell acute lymphoblastic leukemia, adult acute lymphoblastic leukemia, B-cell prolymphocytic leukemia, childhood acute lymphoblastic leukemia, refractory childhood acute lymphoblastic leukemia, acute leukemia, acute lymphoblastic leukemia, acute lymphocytic leukemia, prolymphocytic leukemia, chronic lymphocytic leukemia, acute myeloid leukemia, recurrent plasma cell myeloma, refractory plasma cell myeloma, multiple myeloma, relapsed or refractory multiple myeloma, multiple myeloma of bone, malignant glioma of brain, myelodysplastic syndrome, EGFR-positive colorectal cancer, glioblastoma multiforme, neoplasms, blastic plasmacytoid dendritic cell neoplasms, liver metastases, solid tumors, advanced solid tumors, mesothelin positive tumors, and hematological malignancies.

20. The method of claim 7, wherein the anti-CD5 ADC is administered to the patient as multiple doses.

21. The method of claim 7, wherein the anti-CD5 antibody, or antigen-binding fragment thereof, comprises a heavy chain variable region comprising a CDR1, a CDR2, and a CDR3 having an amino acid sequence as set forth in SEQ ID NOs: 1, 2, and 3, respectively, and comprises a light chain variable region comprising a CDR1, a CDR2, and a CDR3 having an amino acid sequence as set forth in SEQ ID NOs: 4, 5, and 6, respectively.

22. The method of claim 7, wherein the cytotoxin is an antimitotic agent or an RNA polymerase inhibitor.

23. The method of claim 22, wherein the cytotoxin is an RNA polymerase inhibitor which is an amatoxin.

24. The method of claim 22, wherein the cytotoxin is an antimitotic agent which is selected from the group consisting of a maytansine, an auristatin, a pyrrolobenzodiazepine (PBD), and a calicheamicin.

25. The method of claim 7, wherein an extracellular domain of the CAR comprises an scFv antibody or a single chain T cell receptor (scTCR).

26. The method of claim 7, wherein said tumor has a tumor antigen which is selected from the group consisting of CD19, CD22, CD30, CD7, BCMA, CD137, CD22, CD20, AFP, GPC3, MUC1, mesothelin, CD38, PD1, EG, MG7, BCMA, TAC1, CEA, PSCA, CEA, HER2, MUC1, CD33, ROR2, NKR-2, PSCA, CD28, TAA, NKG2D, and CD123.

27. The method of claim 7, wherein a cytoplasmic domain of the CAR comprises a CD28 cytoplasmic signaling domain, a CD3 zeta cytoplasmic signaling domain, an OX40 cytoplasmic signaling domain, and/or a CD137 (4-1BB) cytoplasmic signaling domain.

28. The method of claim 7, wherein the human subject having cancer has a cancer selected from the group consisting of leukemia, adult advanced cancer, pancreatic cancer, non-resectable pancreatic cancer, colorectal cancer, metastatic colorectal cancer, ovarian cancer, triple-negative breast cancer, hematopoietic/lymphoid cancer, colon cancer liver metastasis, small cell lung cancer, non-small cell lung cancer, B-cell lymphoma, relapsed or refractory B-cell lymphoma, follicular lymphoma, mantle cell lymphoma, diffuse large cell lymphoma, relapsed or refractory diffuse large cell lymphoma, anaplastic large cell lymphoma, primary mediastinal B-cell lymphoma, recurrent mediastinal, refractory mediastinal large B-cell lymphoma, large B-cell lymphoma, Hodgkin lymphoma, non-Hodgkin lymphoma, relapsed or refractory non-Hodgkin lymphoma, refractory aggressive non-Hodgkin lymphoma, B-cell non-Hodgkin lymphoma, refractory non-Hodgkin lymphoma, colorectal carcinoma, gastric carcinoma, pancreatic carcinoma, triple-negative invasive breast carcinoma, renal cell carcinoma, lung squamous cell carcinoma, hepatocellularcarcinoma, urothelial carcinoma, leukemia, B-cell leukemia, B-cell acute lymphocytic leukemia, B-cell acute lymphoblastic leukemia, adult acute lymphoblastic leukemia, B-cell prolymphocytic leukemia, childhood acute lymphoblastic leukemia, refractory childhood acute lymphoblastic leukemia, acute leukemia, acute lymphoblastic leukemia, acute lymphocytic leukemia, prolymphocytic leukemia, chronic lymphocytic leukemia, acute myeloid leukemia, recurrent plasma cell myeloma, refractory plasma cell myeloma, multiple myeloma, relapsed or refractory multiple myeloma, multiple myeloma of bone, malignant glioma of brain, myelodysplastic syndrome, EGFR-positive colorectal cancer, glioblastoma multiforme, neoplasms, blastic plasmacytoid dendritic cell neoplasms, liver metastases, solid tumors, advanced solid tumors, mesothelin positive tumors, and hematological malignancies.

29. The method of claim 1, wherein administering the immune cell expressing a CAR to said human subject occurs about 12 hours to about 21 days after step (a).

30. The method of claim 1, wherein administering the anti-CD5 ADC to the human subject in step (a) reduces endogenous lymphocytes.

* * * * *

SEQUENCE LISTING

```
<160> NUMBER OF SEQ ID NOS: 282

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Ala Pro Gly Lys Gly Leu Glu
        35                  40                  45

Trp Val Ala His Ile Trp Trp Asp Asp Val Tyr Tyr Asn Pro Ser
    50                  55                  60

Leu Lys Ser Arg Leu Thr Ile Thr Lys Asp Ala Ser Lys Asp Gln Val
65                  70                  75                  80

Ser Leu Lys Leu Ser Ser Val Thr Ala Ala Asp Thr Ala Val Tyr Tyr
                85                  90                  95

Cys Val Arg Arg Arg Ala Thr Gly Thr Gly Phe Asp Tyr Trp Gly Gln
            100                 105                 110

Gly Thr Leu Val Thr Val Ser Ser
        115                 120

<210> SEQ ID NO 2
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30
```

```
Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys
            100                 105

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Ser Leu Ser Thr Ser Gly Met Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Trp Asp Asp Asp
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg Ala Thr Gly Thr Gly Phe Asp Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Asp Val Gly Thr Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 7

Trp Thr Ser Thr Arg His Thr
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Asn Ser Tyr Asn Thr
1               5

<210> SEQ ID NO 9
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala
        35                  40                  45

<210> SEQ ID NO 10
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Pro Arg
        35                  40                  45

Lys Ile Glu Val Met Tyr Pro Pro Tyr Leu Asp Asn Glu Lys Ser
    50                  55                  60

Asn Gly Thr Ile Ile His Val Lys Gly Lys His Leu Cys Pro Ser Pro
65                  70                  75                  80

Leu Phe Pro Gly Pro Ser Lys Pro
                85

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 11

Leu Asp Pro Lys Leu Cys Tyr Leu Leu Asp Gly Ile Leu Phe Ile Tyr
 1               5                  10                  15

Gly Val Ile Leu Thr Ala Leu Phe Leu Arg Val Lys
            20                  25

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Cys Tyr Leu Leu Asp Gly Ile Leu Phe Ile Tyr Gly Val Ile Leu
 1               5                  10                  15

Thr Ala Leu Phe Leu
            20

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Trp Val Leu Val Val Val Gly Gly Val Leu Ala Cys Tyr Ser Leu
 1               5                  10                  15

Leu Val Thr Val Ala Phe Ile Ile Phe Trp Val
            20                  25

<210> SEQ ID NO 14

<400> SEQUENCE: 14

000

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Arg Val Lys Phe Ser Arg Ser Ala Asp Ala Pro Ala Tyr Gln Gln Gly
 1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
```

<210> SEQ ID NO 16
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 17
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser
1               5

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 495

<212> TYPE: PRT
<213> ORGANISM: Homo sapiens

<400> SEQUENCE: 20

```
Met Pro Met Gly Ser Leu Gln Pro Leu Ala Thr Leu Tyr Leu Leu Gly
1               5                   10                  15

Met Leu Val Ala Ser Cys Leu Gly Arg Leu Ser Trp Tyr Asp Pro Asp
            20                  25                  30

Phe Gln Ala Arg Leu Thr Arg Ser Asn Ser Lys Cys Gln Gly Gln Leu
        35                  40                  45

Glu Val Tyr Leu Lys Asp Gly Trp His Met Val Cys Ser Gln Ser Trp
    50                  55                  60

Gly Arg Ser Ser Lys Gln Trp Glu Asp Pro Ser Gln Ala Ser Lys Val
65                  70                  75                  80

Cys Gln Arg Leu Asn Cys Gly Val Pro Leu Ser Leu Gly Pro Phe Leu
                85                  90                  95

Val Thr Tyr Thr Pro Gln Ser Ser Ile Ile Cys Tyr Gly Gln Leu Gly
            100                 105                 110

Ser Phe Ser Asn Cys Ser His Ser Arg Asn Asp Met Cys His Ser Leu
        115                 120                 125

Gly Leu Thr Cys Leu Glu Pro Gln Lys Thr Thr Pro Thr Thr Arg
130                 135                 140

Pro Pro Pro Thr Thr Thr Pro Glu Pro Thr Ala Pro Pro Arg Leu Gln
145                 150                 155                 160

Leu Val Ala Gln Ser Gly Gly Gln His Cys Ala Gly Val Val Glu Phe
                165                 170                 175

Tyr Ser Gly Ser Leu Gly Gly Thr Ile Ser Tyr Glu Ala Gln Asp Lys
            180                 185                 190

Thr Gln Asp Leu Glu Asn Phe Leu Cys Asn Asn Leu Gln Cys Gly Ser
        195                 200                 205

Phe Leu Lys His Leu Pro Glu Thr Glu Ala Gly Arg Ala Gln Asp Pro
210                 215                 220

Gly Glu Pro Arg Glu His Gln Pro Leu Pro Ile Gln Trp Lys Ile Gln
225                 230                 235                 240

Asn Ser Ser Cys Thr Ser Leu Glu His Cys Phe Arg Lys Ile Lys Pro
                245                 250                 255

Gln Lys Ser Gly Arg Val Leu Ala Leu Leu Cys Ser Gly Phe Gln Pro
            260                 265                 270

Lys Val Gln Ser Arg Leu Val Gly Gly Ser Ser Ile Cys Glu Gly Thr
        275                 280                 285

Val Glu Val Arg Gln Gly Ala Gln Trp Ala Ala Leu Cys Asp Ser Ser
290                 295                 300

Ser Ala Arg Ser Ser Leu Arg Trp Glu Glu Val Cys Arg Glu Gln Gln
305                 310                 315                 320

Cys Gly Ser Val Asn Ser Tyr Arg Val Leu Asp Ala Gly Asp Pro Thr
                325                 330                 335

Ser Arg Gly Leu Phe Cys Pro His Gln Lys Leu Ser Gln Cys His Glu
            340                 345                 350

Leu Trp Glu Arg Asn Ser Tyr Cys Lys Lys Val Phe Val Thr Cys Gln
        355                 360                 365

Asp Pro Asn Pro Ala Gly Leu Ala Ala Gly Thr Val Ala Ser Ile Ile
370                 375                 380

Leu Ala Leu Val Leu Leu Val Val Leu Leu Val Val Cys Gly Pro Leu
385                 390                 395                 400
```

-continued

```
Ala Tyr Lys Lys Leu Val Lys Phe Arg Gln Lys Lys Gln Arg Gln
            405                 410                 415

Trp Ile Gly Pro Thr Gly Met Asn Gln Asn Met Ser Phe His Arg Asn
            420                 425                 430

His Thr Ala Thr Val Arg Ser His Ala Glu Asn Pro Thr Ala Ser His
            435                 440                 445

Val Asp Asn Glu Tyr Ser Gln Pro Pro Arg Asn Ser His Leu Ser Ala
    450                 455                 460

Tyr Pro Ala Leu Glu Gly Ala Leu His Arg Ser Ser Met Gln Pro Asp
465                 470                 475                 480

Asn Ser Ser Asp Ser Asp Tyr Asp Leu His Gly Ala Gln Arg Leu
                485                 490                 495

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Thr Phe Thr Asn Tyr
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asn Thr His Thr Gly Glu
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Gly Tyr Asp Trp Tyr Phe Asp Val
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ala Ser Gln Asp Ile Asn Ser Tyr Leu Ser
1               5                   10

<210> SEQ ID NO 25
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 25

Arg Ala Asn Arg Leu Val Asp
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Tyr Asp Glu Ser Pro Trp Thr
1               5

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95

Thr Phe Gly Gly Gly Thr Lys Leu Glu Ile Lys
            100                 105

<210> SEQ ID NO 28
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Tyr Gly Glu Pro Thr Tyr Ala Asp Ser Phe
    50                  55                  60
```

```
Lys Gly Thr Arg Thr Phe Ser Leu Asp Asp Ser Lys Asn Thr Ala Tyr
 65                  70                  75                  80

Leu Gln Ile Asn Ser Leu Arg Ala Glu Asp Thr Ala Val Tyr Phe Cys
                 85                  90                  95

Thr Arg Arg Gly Tyr Asp Trp Tyr Phe Asp Val Trp Gly Gln Gly Gly
            100                 105                 110

Thr Thr Val Thr Val Ser Ser
        115

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Tyr Thr Phe Thr Asn Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Thr His Tyr Gly Glu
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Gly Tyr Asp Trp Tyr Phe Asp Val
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ala Ser Gln Asp Ile Asn Ser Tyr Leu Ser
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

Arg Ala Asn Arg Leu Glu Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Tyr Asp Glu Ser Pro Trp Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Tyr Ser Ile Thr Ser Gly Tyr Tyr
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Ser Tyr Ser Gly Phe Thr
1               5

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Gly Asp Arg Thr Gly Ser Trp Phe Ala Tyr
1               5                   10

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Asp Ile Ser Asn Tyr
1               5

<210> SEQ ID NO 39
<211> LENGTH: 3
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 39

Ala Thr Ser
1

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Gln Tyr Ala Ser Tyr Pro Phe Thr
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Tyr Ile Phe Thr Asn Tyr Gly
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Asn Thr Tyr Asn Gly Glu Pro
1               5

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Arg Gly Asp Tyr Tyr Gly Tyr Glu Asp Tyr
1               5                   10

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gly Ile Ser Asn Tyr
1               5

```
<210> SEQ ID NO 45
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Thr Ser
1

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Tyr Ser Lys Leu Pro Trp Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Phe Ser Leu Ser Thr Ser Gly Met Gly
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Trp Asp Asp Asp
1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Arg Ala Thr Gly Thr Gly Phe Asp Tyr
1               5                   10

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50
```

Gln Asp Val Gly Thr Ala
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Thr Ser Thr Arg His Thr
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Tyr Asn Ser Tyr Asn Thr
1               5

<210> SEQ ID NO 53
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Ala Pro Gly Lys Gly Leu Glu
        35                  40                  45

Trp Val Ala His Ile Trp Trp Asp Asp Val Tyr Tyr Asn Pro Ser
    50                  55                  60

Leu Lys Ser Arg Leu Thr Ile Thr Lys Asp Ala Ser Lys Asp Gln Val
65                  70                  75                  80

Ser Leu Lys Leu Ser Ser Val Thr Ala Ala Asp Thr Ala Val Tyr Tyr
                85                  90                  95

Cys Val Arg Arg Arg Ala Thr Gly Thr Gly Phe Asp Tyr Trp Gly Gln
            100                 105                 110

Gly Thr Leu Val Thr Val Ser Ser
        115                 120

<210> SEQ ID NO 54
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asn Ile Val Met Thr Gln Ser Pro Ser Ser Leu Ser Ala Ser Val Gly

```
                1               5                   10                  15
Asp Arg Val Thr Ile Thr Cys Gln Ala Ser Gln Asp Val Gly Thr Ala
                20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys
            100                 105
```

<210> SEQ ID NO 55
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Ala Met Ser Trp Val Arg Gln Ala Pro Gly Lys Gly Leu Glu Trp Val
            35                  40                  45

Ala Val Ile Ser Glu Asn Gly Ser Asp Thr Tyr Tyr Ala Asp Ser Val
        50                  55                  60

Lys Gly Arg Phe Thr Ile Ser Arg Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ser Tyr Phe Asp Val Trp Gly Gln
            100                 105                 110

Gly Thr Leu Val Thr Val Ser Ser
        115                 120
```

<210> SEQ ID NO 56
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Asn Ser Leu Pro Tyr
                    85                  90                  95

Thr Phe Gly Gln Gly Thr Lys Val Glu Ile Lys Arg Thr
                100                 105

<210> SEQ ID NO 57
<211> LENGTH: 438
<212> TYPE: PRT
<213> ORGANISM: Homo sapiens

<400> SEQUENCE: 57

Met Val Cys Ser Gln Ser Trp Gly Arg Ser Ser Lys Gln Trp Glu Asp
1               5                   10                  15

Pro Ser Gln Ala Ser Lys Val Cys Gln Arg Leu Asn Cys Gly Val Pro
                20                  25                  30

Leu Ser Leu Gly Pro Phe Leu Val Thr Tyr Thr Pro Gln Ser Ser Ile
                35                  40                  45

Ile Cys Tyr Gly Gln Leu Gly Ser Phe Ser Asn Cys Ser His Ser Arg
        50                  55                  60

Asn Asp Met Cys His Ser Leu Gly Leu Thr Cys Leu Glu Pro Gln Lys
65                  70                  75                  80

Thr Thr Pro Pro Thr Thr Arg Pro Pro Thr Thr Pro Glu Pro
                    85                  90                  95

Thr Ala Pro Pro Arg Leu Gln Leu Val Ala Gln Ser Gly Gly Gln His
                100                 105                 110

Cys Ala Gly Val Val Glu Phe Tyr Ser Gly Ser Leu Gly Gly Thr Ile
                115                 120                 125

Ser Tyr Glu Ala Gln Asp Lys Thr Gln Asp Leu Glu Asn Phe Leu Cys
        130                 135                 140

Asn Asn Leu Gln Cys Gly Ser Phe Leu Lys His Leu Pro Glu Thr Glu
145                 150                 155                 160

Ala Gly Arg Ala Gln Asp Pro Gly Glu Pro Arg Glu His Gln Pro Leu
                165                 170                 175

Pro Ile Gln Trp Lys Ile Gln Asn Ser Ser Cys Thr Ser Leu Glu His
                180                 185                 190

Cys Phe Arg Lys Ile Lys Pro Gln Lys Ser Gly Arg Val Leu Ala Leu
                195                 200                 205

Leu Cys Ser Gly Phe Gln Pro Lys Val Gln Ser Arg Leu Val Gly Gly
        210                 215                 220

Ser Ser Ile Cys Glu Gly Thr Val Glu Val Arg Gln Gly Ala Gln Trp
225                 230                 235                 240

Ala Ala Leu Cys Asp Ser Ser Ser Ala Arg Ser Ser Leu Arg Trp Glu
                245                 250                 255

Glu Val Cys Arg Glu Gln Gln Cys Gly Ser Val Asn Ser Tyr Arg Val
                260                 265                 270

Leu Asp Ala Gly Asp Pro Thr Ser Arg Gly Leu Phe Cys Pro His Gln
        275                 280                 285

Lys Leu Ser Gln Cys His Glu Leu Trp Glu Arg Asn Ser Tyr Cys Lys
290                 295                 300

Lys Val Phe Val Thr Cys Gln Asp Pro Asn Pro Ala Gly Leu Ala Ala
                305                 310                 315                 320

Gly Thr Val Ala Ser Ile Ile Leu Ala Leu Val Leu Leu Val Val Leu
                325                 330                 335
```

```
Leu Val Val Cys Gly Pro Leu Ala Tyr Lys Lys Leu Val Lys Lys Phe
            340                 345                 350

Arg Gln Lys Lys Gln Arg Gln Trp Ile Gly Pro Thr Gly Met Asn Gln
        355                 360                 365

Asn Met Ser Phe His Arg Asn His Thr Ala Thr Val Arg Ser His Ala
        370                 375                 380

Glu Asn Pro Thr Ala Ser His Val Asp Asn Glu Tyr Ser Gln Pro Pro
385                 390                 395                 400

Arg Asn Ser His Leu Ser Ala Tyr Pro Ala Leu Glu Gly Ala Leu His
                405                 410                 415

Arg Ser Ser Met Gln Pro Asp Asn Ser Ser Asp Ser Asp Tyr Asp Leu
                420                 425                 430

His Gly Ala Gln Arg Leu
            435

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Met Ser Ala Ser Leu Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95

Thr Phe Gly Gly Gly Thr Lys Leu Glu Ile Lys
            100                 105

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Ile Gln Leu Val Gln Ser Gly Pro Gly Leu Lys Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Arg Trp Met
        35                  40                  45

Gly Trp Ile Asn Thr His Thr Gly Glu Pro Thr Tyr Ala Asp Asp Phe
    50                  55                  60

Lys Gly Arg Phe Thr Phe Ser Leu Asp Thr Ser Lys Ser Thr Ala Tyr
65                  70                  75                  80
```

-continued

```
Leu Gln Ile Asn Ser Leu Arg Ala Glu Asp Thr Ala Thr Tyr Phe Cys
                85                  90                  95

Thr Arg Arg Gly Tyr Asp Trp Tyr Phe Asp Val Trp Gly Gln Gly Thr
            100                 105                 110

Thr Val Thr Val Ser Ser
        115
```

<210> SEQ ID NO 60
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Ser Gly Tyr Ser Phe Thr Gly Tyr Thr Met
1               5                   10
```

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Ser Gly Tyr Ser Phe Thr Asp Tyr Thr Met
1               5                   10
```

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Ser Gly Tyr Ser Phe Thr Gly Tyr Thr Met
1               5                   10
```

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 64

Ser Gly Tyr Ser Phe Thr Gly Tyr Thr Met
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Gly Tyr Ser Phe Thr Gly Tyr Thr Met
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Gly Phe Thr Phe Ser Asn Tyr Ala Met
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Gly Phe Thr Phe Ser Ser Tyr Ala Met
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Gly Tyr Ser Phe Thr Ala Tyr Asn Ile
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Gly Tyr Ser Phe Thr Ala Tyr Ser Met
1               5                   10

<210> SEQ ID NO 70
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Gly Tyr Thr Phe Thr Asn Phe Ala Ile
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Gly Tyr Thr Phe Thr Asn Phe Ala Ile
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ser Gly Tyr Thr Phe Thr Asn Phe Ala Ile
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Gly Tyr Thr Phe Thr Asn Phe Ala Ile
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Gly Phe Asn Ile Lys Asp Thr Tyr Met
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ser Gly Tyr Ser Phe Thr Ser Tyr Trp Met
```

```
1               5                  10
```

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

```
Ser Gly Phe Ser Leu Thr Asn Tyr Asp Val
1               5                  10
```

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

```
Ser Gly Phe Ser Leu Thr Asn Tyr Asp Val
1               5                  10
```

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

```
Ser Gly Phe Thr Phe Ser Asn Tyr Gly Met
1               5                  10
```

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Ser Gly Tyr Ser Phe Thr Gly Tyr Thr Met
1               5                  10
```

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

```
Ser Gly Tyr Ile Phe Ala Asn Tyr Gly Met
1               5                  10
```

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 81

Ser Gly Tyr Asn Phe Thr Asn Tyr Gly Met
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Gly Tyr Thr Phe Thr Asn Tyr Gly Met
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Gly Tyr Thr Phe Thr Asp Tyr Tyr Ile
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Gly Tyr Thr Phe Thr Asp Tyr Tyr Ile
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Gly Asn Thr Phe Thr Asn Phe Tyr Leu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Gly Tyr Thr Phe Thr Asn Tyr Gly Met
1               5                   10

<210> SEQ ID NO 87
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Glu Phe Thr Phe Ser Asn Tyr Ala Met
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Gly Tyr Thr Phe Thr Ser Tyr Arg Met
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Gly Phe Asn Ile Lys Asp Thr Tyr Met
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ser Gly Tyr Ser Phe Thr Asp Tyr Thr Met
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Gly Tyr Met Phe Thr Asn His Gly Met
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92
```

Ser Gly Tyr Met Phe Thr Asn Tyr Gly Met
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Gly Tyr Ile Phe Thr Asn Tyr Gly Met
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Gly Phe Asn Ile Lys Asp Tyr Tyr Ile
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Gly Tyr Thr Phe Ile Asn Tyr Gly Met
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Gly Tyr Thr Phe Thr Asp Tyr Phe Ile
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Gly Tyr Ile Phe Thr Gly Tyr Asn Ile
1               5                   10

<210> SEQ ID NO 98
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 98

Leu Ile Asn Pro Tyr Asn Gly Gly Thr Thr
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Leu Ile Asn Pro Tyr Asn Gly Gly Thr Met
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Leu Ile Asn Pro Tyr Asn Gly Gly Thr Met
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Ile Asn Pro Tyr Asn Gly Gly Thr Met
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Leu Ile Asn Pro Tyr Asn Gly Gly Thr Thr
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Ile Ser Ser Gly Gly Asn Thr Phe
1               5
```

-continued

```
<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ile Ser Ser Gly Gly Ser Thr Tyr
1               5

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Ile Asp Pro Tyr Tyr Gly Asp Thr Lys
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Ile Asp Pro Tyr Tyr Gly Asp Thr Lys
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Leu Ile Ser Ser Asn Ser Gly Asp Val Ser
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Leu Ile Ser Thr Ser Ser Gly Asp Val Ser
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109
```

```
Leu Ile Ser Ser Asn Ser Gly Asp Val Ser
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Leu Ile Ser Ser Asn Ser Gly Asp Val Ser
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ile Asp Pro Ala Asn Gly Asn Thr Lys
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Met Ile His Pro Ser Asp Ser Glu Thr Arg
1               5                   10

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Val Ile Trp Ser Gly Gly Asn Thr Asp
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Val Ile Trp Ser Gly Gly Asn Thr Asp
1               5

<210> SEQ ID NO 115
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 115

Ala Ile Asn Ser Asn Gly Asp Ile Thr Tyr
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Leu Ile Asn Pro Tyr Asn Gly Gly Thr Arg
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Trp Ile Asn Thr Tyr Thr Gly Glu Pro Thr
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Ile Asn Thr Tyr Thr Gly Glu Pro Thr
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Trp Ile Asn Thr Tyr Thr Gly Glu Pro Thr
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Trp Ile Tyr Pro Gly Gly Gly Asn Thr Arg
1               5                   10
```

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Trp Ile Tyr Pro Gly Gly Gly Asn Thr Arg
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Cys Ile Tyr Pro Gly Asn Val Lys Thr Lys
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Trp Ile Asn Thr Tyr Thr Gly Glu Pro Thr
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Ile Ser Ser Gly Gly Ser Tyr Thr Tyr
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Ile Asp Pro Tyr Asp Ser Gly Thr His
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 126

Arg Ile Asp Pro Ala Asn Gly Asn Thr Lys
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Leu Ile Asn Pro Tyr Asn Gly Gly Thr Arg
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Trp Ile Asn Thr Tyr Thr Gly Glu Pro Thr
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Trp Ile Asn Thr Tyr Thr Gly Glu Pro Thr
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Trp Ile Asn Thr Tyr Thr Gly Glu Pro Thr
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Trp Ile Asp Pro Glu Asn Gly Arg Thr Glu
1               5                   10

<210> SEQ ID NO 132
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 132

Trp Ile Asn Thr Tyr Thr Gly Glu Pro Thr
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Glu Ile Tyr Pro Gly Ser Ser Asn Thr Tyr
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Val Tyr Pro Gly Asn Gly Asp Thr Ser
1               5                   10

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Cys Ala Arg Asp Tyr Tyr Gly Ser Ser Pro Asp Phe Asp Tyr Trp
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Ala Arg Asp Asn Tyr Gly Ser Ser Pro Asp Phe Asp Tyr Trp
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Cys Ala Arg Asp Asn Tyr Gly Ser Ser Pro Tyr Phe Asp Tyr Trp
1               5                   10                  15
```

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Cys Ala Arg Asp Asn Tyr Gly Ser Ser Pro Tyr Phe Asp Tyr Trp
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Cys Ala Arg Asp Tyr Tyr Gly Ser Ser Pro Asp Phe Asp Tyr Trp
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Cys Val Arg Tyr Tyr Tyr Gly Val Thr Tyr Trp Tyr Phe Asp Val Trp
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Cys Val Arg Tyr Tyr Tyr Gly Ile Arg Tyr Trp Tyr Phe Asp Val Trp
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Cys Ala Arg Arg Met Ile Thr Met Gly Asp Trp Tyr Phe Asp Val Trp
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Cys Ala Arg Arg Met Ile Thr Thr Gly Asp Trp Tyr Phe Asp Val Trp
1               5                   10                  15

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Cys Ala Arg His Tyr Gly Ala His Asn Tyr Phe Asp Tyr Trp
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Cys Ala Arg His Tyr Gly Ala Asn Asn Tyr Phe Asp Tyr Trp
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Cys Ala Arg His Tyr Gly Ala His Asn Tyr Phe Asp Tyr Trp
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Cys Ala Arg His Tyr Gly Ala His Asn Tyr Phe Asp Tyr Trp
1               5                   10

<210> SEQ ID NO 148
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Cys Ala Arg Glu Glu Asn Tyr Tyr Gly Thr Tyr Tyr Phe Asp Tyr Trp
1               5                   10                  15

<210> SEQ ID NO 149
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Cys Ala Arg Trp Gly Asp His Asp Asp Ala Met Asp Phe Trp
1               5                   10

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Cys Ala Arg Asn His Gly Asp Gly Tyr Phe Asn Trp Tyr Phe Asp Val
1               5                   10                  15

Trp

<210> SEQ ID NO 151
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Cys Ala Arg Asn His Gly Asp Gly Tyr Tyr Asn Trp Tyr Phe Asp Val
1               5                   10                  15

Trp

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Cys Ala Arg Gly Thr Ala Trp Phe Thr Tyr Trp
1               5                   10

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Cys Ala Arg Asp Gly Asp Asp Gly Trp Asp Ile Asp Val Trp
1               5                   10

<210> SEQ ID NO 154
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 154

Cys Ala Arg Arg Gly Thr Tyr Trp His Phe Asp Val Trp
1               5                   10

<210> SEQ ID NO 155
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Cys Ala Arg Arg Gly Ser Tyr Trp His Phe Asp Val Trp
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Cys Ala Arg Arg Ser Thr Leu Val Phe Asp Tyr Trp
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Cys Ala Arg Asn Gly Tyr Trp Tyr Phe Asp Val Trp
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Cys Ala Arg Asn Gly Tyr Trp Tyr Phe Asp Val Trp
1               5                   10

<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Cys Ala Lys Glu Gly Asp Tyr Asp Gly Thr Ala Tyr Phe Asp Tyr Trp
1               5                   10                  15

<210> SEQ ID NO 160
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Cys Ala Arg Arg Arg Asp Gly Asn Phe Asp Tyr Trp
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Cys Val Arg His Gly Tyr Phe Asp Val Trp
1               5                   10

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Cys Ala Phe Tyr Asp Gly Ala Tyr Trp
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Cys Ala Ser Tyr Asp Pro Asp Tyr Trp
1               5

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Ala Arg Asp Thr Thr Ala Thr Tyr Tyr Phe Asp Tyr Trp
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Cys Ala Arg Arg Val Ala Thr Tyr Phe Asp Val Trp
```

```
1               5                   10
```

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

```
Cys Thr Arg Arg Ser His Ile Thr Leu Asp Tyr Trp
1               5                   10
```

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

```
Cys Ala Arg Arg Arg Thr Thr Ala Phe Asp Tyr Trp
1               5                   10
```

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

```
Cys Asn Asn Gly Asn Tyr Val Arg His Tyr Tyr Phe Asp Tyr Trp
1               5                   10                  15
```

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

```
Cys Thr Arg Arg Arg Glu Ile Thr Phe Asp Tyr Trp
1               5                   10
```

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

```
Cys Ala Arg Ser Gly Ile Ser Pro Phe Thr Tyr Trp
1               5                   10
```

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic

```
                       peptide

<400> SEQUENCE: 171

Cys Ala Lys Tyr Asp Arg Phe Phe Ala Ser Trp
1               5                   10

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Gln Gly Ile Ser Asn His Leu
1               5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Gln Gly Ile Arg Asn Tyr Leu
1               5

<210> SEQ ID NO 174
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Gln Gly Ile Ser Asn His Leu
1               5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Gln Gly Ile Asn Asn Tyr Leu
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Gln Gly Ile Ser Asn His Leu
1               5

<210> SEQ ID NO 177
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Gln Ser Val Asp His Asp Gly Asp Ser Tyr Met
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Gln Ser Val Asp Tyr Asp Gly Asp Ser Tyr Met
1               5                   10

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Gln Asp Ile Ser Asn Tyr Leu
1               5

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ser Gln Asp Ile Ser Thr Tyr Leu
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Thr Ser Ser Ile Ser Ser Ser Tyr Leu
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182
```

```
Asn Ser Ser Val Ser Ser Ser Tyr Leu
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Thr Ser Ser Ile Ser Ser Ser Tyr Leu
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Thr Ser Ser Ile Ser Ser Ser Tyr Leu
1               5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Glu Asn Ile Tyr Tyr Asn Leu
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Glu Asn Ile Tyr Gly Tyr Phe
1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Gln Asp Ile Asn Asn Tyr Ile
1               5

<210> SEQ ID NO 188
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 188

Ser Gln Asp Ile Asn Lys Tyr Ile
1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ser Glu Asn Ile Tyr Ser Tyr Leu
1               5

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Gln Gly Ile Arg Asn Tyr Leu
1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Gln Asp Val Arg Thr Asp Val
1               5

<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Gln Asp Val Ile Thr Ala Val
1               5

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Gln Ser Ile Gly Thr Ser Ile
1               5
```

```
<210> SEQ ID NO 194
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Ser Gln Ser Leu Leu Asn Gln Lys Asn Tyr Leu
1               5                   10

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ser Ser Ser Val Ser Ser Ser Tyr Leu
1               5

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ser Glu Asn Ile Tyr Tyr Asn Leu
1               5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Gln Thr Ile Gly Thr Ser Ile
1               5

<210> SEQ ID NO 198
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Gln Ser Leu Leu Tyr Ser Ser Asp Gln Lys Asn Tyr Leu
1               5                   10

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199
```

Asn Ser Ser Val Ser Tyr Met
1               5

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ser Glu Asn Ile Tyr Tyr Asn Leu
1               5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Ser Ser Leu Ser Tyr Met
1               5

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ser Gln Arg Ile Gly Thr Ser Met
1               5

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Gln Ser Ile Gly Thr Ser Ile
1               5

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Gln Asn Ile Gly Thr Ser Ile
1               5

<210> SEQ ID NO 205
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 205

Ile Ser Ser Val Ser Tyr Met
1               5

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Gln Thr Ile Ala Thr Ser Ile
1               5

<210> SEQ ID NO 207
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Gln Ser Leu Val His Ser Asn Gly Asn Thr Tyr Leu
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asn Glu Ser Val Glu Tyr Ser Gly Thr Ser Leu Met
1               5                   10

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Tyr Phe Thr Ser Ser
1               5

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Tyr Phe Thr Ser Ser
1               5
```

<210> SEQ ID NO 211
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Tyr Phe Thr Ser Ser
1               5

<210> SEQ ID NO 212
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Tyr Tyr Thr Ser Ser
1               5

<210> SEQ ID NO 213
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Tyr Phe Thr Ser Ser
1               5

<210> SEQ ID NO 214
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Tyr Ala Ala Ser Asn
1               5

<210> SEQ ID NO 215
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Tyr Ala Ala Ser Asn
1               5

<210> SEQ ID NO 216
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 216

Tyr Tyr Thr Ser Arg
1               5

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Phe Tyr Thr Ser Arg
1               5

<210> SEQ ID NO 218
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Tyr Gly Thr Ser Asn
1               5

<210> SEQ ID NO 219
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Tyr Gly Thr Ser Asn
1               5

<210> SEQ ID NO 220
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Tyr Gly Thr Ser Asn
1               5

<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Tyr Gly Thr Ser Asn
1               5

<210> SEQ ID NO 222
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 222

Tyr Asn Ala Asn Ser
1               5

<210> SEQ ID NO 223
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Tyr Asn Ala Lys Thr
1               5

<210> SEQ ID NO 224
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

His Tyr Thr Ser Thr
1               5

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

His Tyr Thr Ser Thr
1               5

<210> SEQ ID NO 226
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Tyr Asn Ala Lys Thr
1               5

<210> SEQ ID NO 227
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Tyr His Thr Ser Thr
1               5
```

```
<210> SEQ ID NO 228
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Tyr Ser Ala Ser Phe
1               5

<210> SEQ ID NO 229
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Tyr Ser Ala Ser Tyr
1               5

<210> SEQ ID NO 230
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Lys Ser Ala Ser Glu
1               5

<210> SEQ ID NO 231
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Tyr Trp Ala Ser Thr
1               5

<210> SEQ ID NO 232
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Tyr Ser Thr Ser Asn
1               5

<210> SEQ ID NO 233
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 233

Tyr Asn Ala Asn Ser
1               5

<210> SEQ ID NO 234
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Lys Asn Ala Ser Glu
1               5

<210> SEQ ID NO 235
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Tyr Trp Ala Ser Thr
1               5

<210> SEQ ID NO 236
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Tyr Asp Thr Ser Lys
1               5

<210> SEQ ID NO 237
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Tyr Asn Ala Asn Ser
1               5

<210> SEQ ID NO 238
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Tyr Asp Thr Ser Asn
1               5

<210> SEQ ID NO 239
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Lys Ser Ala Ser Glu
1               5

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Lys Ser Ala Ser Glu
1               5

<210> SEQ ID NO 241
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Lys Asp Ala Ser Glu
1               5

<210> SEQ ID NO 242
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Tyr Ala Thr Ser Asn
1               5

<210> SEQ ID NO 243
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Lys Asn Ala Ser Glu
1               5

<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Tyr Lys Val Ser Asn
```

```
1               5

<210> SEQ ID NO 245
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Ser Ala Ala Ser Asn
1               5

<210> SEQ ID NO 246
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Cys Gln Gln Tyr Ser Asn Leu Pro Tyr Thr Phe
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Cys Gln Gln Tyr Ser Asn Leu Pro Tyr Thr Phe
1               5                   10

<210> SEQ ID NO 248
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Cys Gln Gln Tyr Ser Asn Leu Pro Tyr Thr Phe
1               5                   10

<210> SEQ ID NO 249
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Cys Gln Gln Tyr Ser Lys Ile Pro Tyr Thr Cys
1               5                   10

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 250

Cys Gln Gln Tyr Ser Asn Leu Pro Tyr Thr Phe
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Cys Gln Gln Asn Tyr Glu Asp Pro Thr Phe
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Cys Gln Gln Ser Asn Glu Asp Pro Thr Phe
1               5                   10

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Cys Gln Gln Gly Asp Ala Leu Pro Trp Thr Phe
1               5                   10

<210> SEQ ID NO 254
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Cys Gln Gln Gly Asn Ser Leu Pro Phe Thr Phe
1               5                   10

<210> SEQ ID NO 255
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Cys Gln Gln Trp Ser Ser Arg Pro Pro Thr Phe
1               5                   10

<210> SEQ ID NO 256

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Cys Gln Gln Tyr Ser Gly Tyr Pro Leu Thr Phe
1               5                   10

<210> SEQ ID NO 257
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Cys Gln Gln Tyr Ser Asp Tyr Pro Leu Thr Phe
1               5                   10

<210> SEQ ID NO 258
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Cys Gln Gln Arg Ser Tyr Phe Pro Phe Thr Phe
1               5                   10

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Cys Lys Gln Val Tyr Asp Val Pro Phe Thr Phe
1               5                   10

<210> SEQ ID NO 260
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Cys Gln His His Tyr Gly Thr Pro Phe Thr Phe
1               5                   10

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261
```

```
Cys Leu Gln Tyr Asp Asn Leu Trp Thr Phe
1               5                   10

<210> SEQ ID NO 262
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Cys Leu Gln Tyr Asp Asn Leu Trp Thr Phe
1               5                   10

<210> SEQ ID NO 263
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Cys Gln His His Tyr Gly Tyr Pro Tyr Thr Phe
1               5                   10

<210> SEQ ID NO 264
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Cys Gln Gln Tyr Ser Asn Leu Pro Leu Thr Phe
1               5                   10

<210> SEQ ID NO 265
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Cys Gln Gln His Tyr Thr Ser Pro Trp Thr Phe
1               5                   10

<210> SEQ ID NO 266
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Cys Gln Gln His Tyr Ser Thr Pro Trp Thr Phe
1               5                   10

<210> SEQ ID NO 267
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 267

Cys Gln Gln Ser Asn Arg Trp Pro Leu Thr Phe
1               5                   10

<210> SEQ ID NO 268
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Cys Gln Asn Asp Tyr Asp Tyr Pro Tyr Thr Phe
1               5                   10

<210> SEQ ID NO 269
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Cys His Gln Tyr His Arg Ser Pro Leu Thr Phe
1               5                   10

<210> SEQ ID NO 270
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Cys Gln Gln Thr Phe Asp Val Pro Trp Thr Phe
1               5                   10

<210> SEQ ID NO 271
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Cys Gln Gln Ser Asn Ser Trp Pro Leu Thr Tyr
1               5                   10

<210> SEQ ID NO 272
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Cys Gln Gln Tyr Tyr Asn Tyr Pro Leu Thr Phe
1               5                   10

```
<210> SEQ ID NO 273
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Cys Gln Gln Trp Ser Ser Asn Pro Phe Thr Phe
1               5                   10

<210> SEQ ID NO 274
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Cys Lys Gln Ala Tyr Asp Val Pro Trp Thr Phe
1               5                   10

<210> SEQ ID NO 275
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Cys Gln Gln Trp Ser Ser Phe Pro Pro Thr Phe
1               5                   10

<210> SEQ ID NO 276
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Cys Gln Gln Ser Asn Ser Trp Pro Leu Thr Phe
1               5                   10

<210> SEQ ID NO 277
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Cys Gln Gln Ser Asn Ser Trp Pro Leu Thr Phe
1               5                   10

<210> SEQ ID NO 278
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278
```

```
Cys Gln Gln Ser Asp Ser Trp Pro Leu Thr Phe
1               5                   10

<210> SEQ ID NO 279
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Cys Gln Gln Trp Ser Ser Asn Pro Arg Thr Phe
1               5                   10

<210> SEQ ID NO 280
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Cys Gln Gln Ser Asn Ser Trp Pro Leu Thr Phe
1               5                   10

<210> SEQ ID NO 281
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Cys Trp Gln Asn Thr His Phe Pro Gln Thr Phe
1               5                   10

<210> SEQ ID NO 282
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Cys Gln Gln Ser Arg Gln Val Pro Leu Thr Phe
1               5                   10
```